(12) United States Patent
Lee et al.

(10) Patent No.: US 6,352,993 B1
(45) Date of Patent: Mar. 5, 2002

(54) PYRIMIDINE DERIVATIVES AND PROCESSES FOR THE PREPARATION THEREOF

(75) Inventors: Jong Wook Lee; Bong Yong Lee; Chang Seop Kim; Seung Kyu Lee; Keun Seog Song; Song Jin Lee, all of Kyunggi-do; Woo Jeon Shim, Daejeon; Man Soon Hwang, Kyunggi-do, all of (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 09/381,814

(22) PCT Filed: Mar. 24, 1998

(86) PCT No.: PCT/KR98/00058
§ 371 Date: Sep. 24, 1999
§ 102(e) Date: Sep. 24, 1999

(87) PCT Pub. No.: WO98/43968
PCT Pub. Date: Oct. 8, 1998

(30) Foreign Application Priority Data

Mar. 27, 1997 (KR) ............................................. 97/10862
Mar. 27, 1997 (KR) ............................................. 97/10863

(51) Int. Cl.$^7$ ..................... C07D 401/04; A61K 31/506
(52) U.S. Cl. ....................... 514/275; 514/272; 544/298; 544/320; 544/321; 544/330; 544/331; 544/332
(58) Field of Search ............................... 544/332, 298, 544/330; 514/275, 269, 272

(56) References Cited

U.S. PATENT DOCUMENTS

| | | | |
|---|---|---|---|
| 3,956,495 A | 5/1976 | Lacefield | 424/251 |
| 3,960,861 A | 6/1976 | Danilewicz et al. | 260/256.4 Q |
| 3,980,781 A | 9/1976 | Snell et al. | 260/256.4 C |
| 4,000,138 A | 12/1976 | Snell et al. | 260/256.4 C |
| 4,044,136 A | 8/1977 | Danilewicz et al. | 424/251 |
| 5,064,833 A | 11/1991 | Ife et al. | 514/260 |
| 5,075,316 A | 12/1991 | Hubele | 514/275 |
| 5,276,186 A | 1/1994 | Waditschatka | 564/238 |
| 5,525,604 A | 6/1996 | Lee et al. | 514/256 |

FOREIGN PATENT DOCUMENTS

| | | |
|---|---|---|
| EP | 0 230 871 | 8/1987 |
| EP | 0 337 943 | 10/1989 |
| EP | 0 388 838 | 9/1990 |
| EP | 0 560 726 | 9/1993 |
| EP | 0 640 599 | 3/1995 |
| EP | 0 379 086 | 4/1996 |
| GB | 1182584 | 2/1970 |
| WO | 91/18887 | 12/1991 |
| WO | 92/07844 | 5/1992 |
| WO | WO 92/18498 | 10/1992 |
| WO | WO 94/14795 | 7/1994 |
| WO | 95/10506 | 4/1995 |
| WO | WO 96/05177 | 2/1996 |
| WO | WO 97/42186 | 11/1997 |

OTHER PUBLICATIONS

Chemical Abstracts, "Preparation of substituted pyrimidine derivatives as analgesics and antiinflammatory agents", vol. 122, Abstract No. 290883s, p. 1041, col. 1, Jun. 5, 1995.
Chemical Abstracts, "Pyrimidine derivative for treatment of ulcerative colitis", vol. 120, Abstract No. 86447g, p. 654, col. 2, Feb. 21, 1994.
Chemical Abstracts, "Oral preparations containing anti-allergy pyrimidine derivative", vol. 118, Abstract No. 87674z, p. 457, col. 1, Mar. 8, 1993.
Chemical Abstracts, "Herbicides. I. 2–(4–Nitroanilino)pyrimidines", vol. 96, Abstract No. 122741v, p. 697, col. 1, Apr. 12, 1982.
Chemical Abstracts, "Biosynthesis of 1–methyl–1,2,3,4–tetrahydroisoquinoline (1MeTIQ), a posible anti–Parkinsonism agent", vol. 118, Abstract No. 249869w, p. 347, col. 2, Jun. 21, 1993.
Chemical Abstracts, "Carbon dioxide: a reagent for the protection of nucleophilic centers and the simultaneous activation of electrophilic attack. Part II. A new synthetic method for the 1–substitution of 1,2,3,4–tetrahydroisoquinolines", vol. 106, Abstract No. 32801k, p. 526, col. 1, Feb. 2, 1987.

(List continued on next page.)

Primary Examiner—John M. Ford
(74) Attorney, Agent, or Firm—Burns, Doane, Swecker & Mathis, L.L.P.

(57) ABSTRACT

The present invention relates to novel pyrimidine derivatives of formula (I) or pharmaceutically acceptable salts thereof which possess an excellent anti-secretory activity, pharmaceutical compositions containing the same as an active ingredient, their novel intermediates, and processes for the preparation thereof wherein: when A is piperidin-1-yl or —NH—B, wherein B is $C_3$–$C_4$ alkyl, $C_3$–$C_4$ alkenyl, $C_3$–$C_7$ cycloalkyl, $C_1$–$C_3$ alkoxyethyl, phenylethl which may be substituted or unsubstituted, 3-trifluoromethylphenylmethyl, 1-naphthylmethyl, 4-methylthiazol-2-yl or 4-phenylthiazol-2-yl, $R_1$ is hydrogen or methyl; and $R_2$, $R_3$, $R_4$ and $R_5$ are hydrogen; or when A is a group of formula (II); when $R_1$ is hydroxymethyl or $C_1$–$C_3$ alkoxymethyl, $R_2$, $R_3$, $R_4$, $R_5$ and $R_6$ are hydrogen; and $R_7$ is hydrogen or halogen; or when $R_1$ is hydrogen or methyl, $R_7$ is hydrogen or halogen; and one or two of $R_2$, $R_3$, $R_4$, $R_5$ and $R_6$ is hydroxy, methoxy, or a group of formula (III) wherein Z is $C_1$–$C_4$ alkyl, substituted or unsubstituted $C_1$–$C_4$ alkenyl, cyloalkyl, benzyloxyalkyl, alkoxycarbonylalkyl, morpholinomethyl, piperidinomethyl, 4-substituted-piperazinomethyl, substituted or unsubstituted phenyl, naphthyl, substituted or unsubstituted benzyl, thiophen-2-yl-methyl, 1-substituted-pyrrolidin-2-yl or —$CHR_8NHR_9$, wherein $R_8$ is hydrogen, methyl, isopropyl, benzyl, benzyloxymethyl, methylthioethyl, benzyloxycarbonylmethyl, carbamolymethyl, carbamoylethyl, or 1-benzylimidazol-4-ylmethyl and $R_9$ is hydrogen or t-butoxycarbonyl; and the others are hydrogen or methyl.

24 Claims, No Drawings

OTHER PUBLICATIONS

Chemical Abstracts, "Synthesis of dihydroisoquinolines and 1–substituted tetrahydroisoquinolines", vol. 96, Abstract No. 217665n, p. 726, col. 1, Jun. 21, 1982.

Chemical Abstracts, "An evaluation of the ortho effect in iso–cytosine derivatives: 2–aralkylamino–and 2–arylamino–3,4–dihydro–pyrimidin–4–(3H)–ones", vol. 121, Abstract No. 256215v, p. 1218, col. 2, Nov. 21, 1994.

Chemical Abstracts, "Interaction of GTP derivatives with cellular and oncogenic ras–p21 proteins", vol. 114, Abstract No. 185899p, p. 833, col. 1, May 13, 1991.

Chemical Abstracts, "Alkylation of isoquinoline skeleton in the 1–position. Lithiated 2–pivaloyl–and 2–bis(dimethylamino)phosphinoyl–1,2,3,4–tetrahydroisoquinolines", vol. 99, Abstract No. 158207b, pp. 597–598, col. 2, Nov. 7, 1983.

PYRIMIDINE DERIVATIVES AND PROCESSES FOR THE PREPARATION THEREOF

This is a 371 of PCT/KR98/00058 filed Feb. 25, 1999.

FIELD OF THE INVENTION

The present invention relates to novel pyrimidine derivatives or pharmaceutically acceptable salts thereof which possess an excellent anti-secretory activity, pharmaceutical compositions containing same as an active ingredient, their novel intermediates, and processes for the preparation thereof.

BACKGROUND OF THE INVENTION

For the treatment of peptic ulcer disease, various drugs such as antacid, anticholinergic agent, $H_2$-receptor antagonist and proton pump inhibitor have been used. The advent of omeprazole useful as a proton pump inhibitor has rekindled research activities in this field.

However, it has been pointed out that the proton pump inhibition by omeprazole is irreversible, which may induce side effects. Accordingly, various attempts to develop a reversible proton pump inhibitor are being actively made. For example, European Patent Nos. 322133 and 404322 disclose quinazoline derivatives, European Patent No. 259174 describes quinoline derivatives, and WO 91/18887 offers pyrimidine derivatives, as a reversible proton pump inhibitor. Further, the present inventors have also reported quinazoline derivatives in WO 94/14795 and pyrimidine derivatives in WO 96/05177.

SUMMARY OF THE INVENTION

The present inventors have carried out extensive research to develop a reversible proton pump inhibitor with improved efficacy, and as a result have discovered that pyrimidine derivatives having a substituted tetrahydroisoquinoline group at 4-position of the pyrimidine nucleus or substituents at the 2-, 5-, or 6-positioni of the pyrirnidine nucleus exhibit excellent proton pump inhibition effects and possess the ability to attain a reversible proton pump inhibition.

Accordingly, it is a primary object of the present invention to provide novel pyrimidine derivatives having a substituted tetraydroisoquinoline group at 4-position of the pyrimidine nucleus or substituents at the 2-, 5-, or 6-position of the pyrirnidine nucleus, or pharmaceutically acceptable salts thereof.

It is another object of the present invention to provide processes for preparing said compounds.

It is a further object of the present invention to provide pharmaceutical compositions for treating peptic ulcer containing the same as active ingredients. it is still another object of the, invention to provide novel intermediate compounds useful for the preparation of the novel pyrimidine derivatives.

In accordance with on aspect of the present invention, there are provided novel pyrimidine derivatives of formula (I) or pharmaceutically acceptable salts thereof:

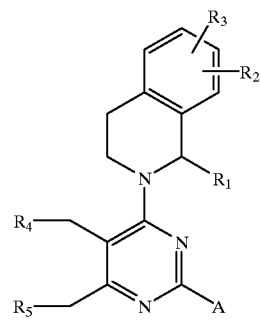

(I)

wherein:
when A is piperidin-1-yl or —NH—B, wherein B is $C_3$–$C_4$ alkenyl, $C_3$–$C_7$ cycloalkyl, $C_1$–$C_3$ alkoxyethyl, phenylethyl which may be substituted or unsubstituted, 3-trifluoromethylphenylmethyl, 1-naphthyl-methyl, 4-methylthiazol-2-yl or 4-phenylthiazol-2-yl, $R_1$ is hydrogen or methyl; and $R_2$, $R_3$, $R_4$ and $R_5$ are hydrogen; or when A is a group of formula (II):

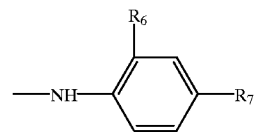

(II)

when $R_1$ is hydroxymethyl or $C_1$–$C_3$ alkoxymethyl, $R_2$, $R_3$, $R_4$, $R_5$ and $R_6$ are hydrogen; and $R_7$ is hydrogen or halogen; or when $R_1$ is hydrogen or methyl, $R_7$ is hydrogen or halogen; and one or two of $R_2$, $R_3$, $R_4$, $R_5$ and $R_6$ is hydroxy, methoxy, or a group of formula (III):

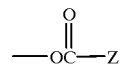

(III)

wherein Z is $C_1$–$C_4$ alkyl, substituted or unsubstituted $C_2$–$C_4$ alkenyl, cycloalkyl, benzyloxyalkyl, alkoxycarbonylalkyl, morpholinomethyl, piperidinomethyl, 4-substituted-piperazine-methyl, substituted or unsubstituted phenyl, naphthyl, substituted or unsubstituted benzyl, thiopen-2-yl-methyl, 1-substituted-pyrrolidin-2-yl or —$CHR_8NHR_9$, wherein $R_8$ is hydrogen, methyl, isopropyl, benzyl, benzyloxymethyl, methylthioethyl, benzyloxycarbonylmethyl, carbamoylmethyl, carbamoylethyl, or 1-benzyl imdazol-4-ylmethyl and $R_9$ is hydrogen or t-butoxycarbonyl; and the others are hydrogen or methyl.

DETAILED DESCRIPTION OF THE INVENTION

Among the compounds of formula (I), preferred are the compounds of the following formula (I-1):

(I-1)

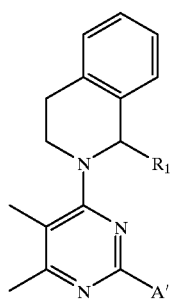

wherein R₁ is hydrogen or methyl; and A' is piperidin-1-yl or —NH—B, wherein B is $C_3$–$C_4$ alkyl, $C_3$–$C_4$ alkenyl, $C_3$–$C_7$ cycloalkyl, $C_1$–$C_3$ alkoxyethyl, phenylethyl which may be substituted or unsubstituted, 3-trifluoromethyl phenylmethyl, 1-naphthylmethyl, 4-methylthiazol-2-yl or 4-phenylthiazol-2-yl.

Among the compounds of the formula (I), also preferred compounds are the compounds of the following formula (I-2):

(I-2)

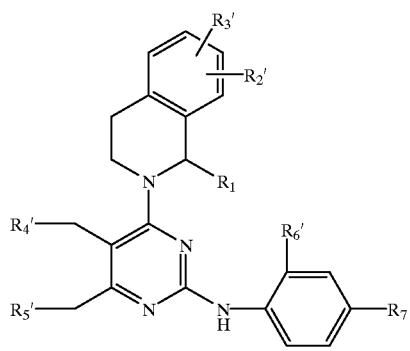

wherein $R_1$ is hydrogen or methyl; $R_7$ is hydrogen or halogen; one or two of $R_2'$, $R_3'$, $R_4'$, $R_5'$ and $R_6'$ is hydroxy or methoxy and the others are hydrogen or methyl.

Similarly preferred compounds are those of the following formula (I-3)

(I-3)

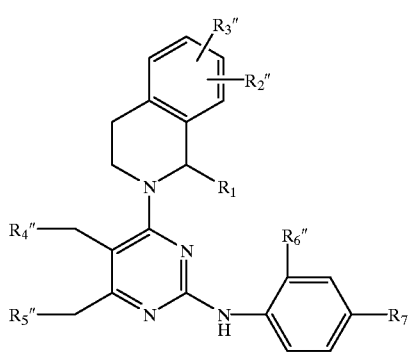

wherein $R_1$ is hydrogen or methyl; $R_7$ is hydrogen or halogen; one or two of $R_2''$, $R_3''$, $R_4''$, $R_5''$ and $R_6''$ is a group of formula (III):

(III)

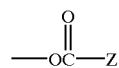

wherein Z is $C_1$–$C_4$ alkyl, substituted or unsbstituted $C_1$–$C_4$ alkenyl, $C_3$–$C_6$ cycloalkyl, benzyloxyalkyl, alkoxycarbonylalkyl, morpholinomethyl, piperidinomethyl, 4-substituted-piperazinomethyl, substituted or unsubstituted phenyl, naphthyl, substituted or unsubstituted benzyl, thiophen-2-yl-methyl, 1-substituted-pyrrolidin-2-yl or —CHR₈NHR₉, wherein $R_8$ is hydrogen, methyl, isopropyl, benzyl, benzyloxymethyl, methylthioethyl, benzyloxycarbonylmethyl, carbamoylmethyl, carbamoylethyl, or 1-benzyl imdazol-4-ylmethyl and $R_9$ is hydrogen or t-butoxycarbonyl; and the others are hydrogen or methyl.

Similarly preferred compounds are those of the following formula (I-4)

(I-4)

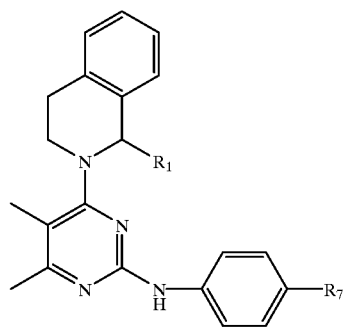

wherein $R_1$ is hydroxymethyl or $C_1$–$C_3$ alkoxymethyl; and $R_7$ is hydrogen or halogen.

The pyrimidine derivatives of formula (I) in the present invention may exist in the form of an optical isomer, (R) or (S), or a mixture thereof. Both types of the isomeric compounds are found to exhibit excellent anti-secretory activity.

The compounds of the formula (I-1), (I-2), (I-3), and (I-4) may be prepared in accordance with the following methods.

Method for Preparation of the Formula (I-1)

The compound of formula (I-1a) may be prepared by reacting the compound (IV) with A"H in accordance with Scheme 1 described below.

Scheme 1

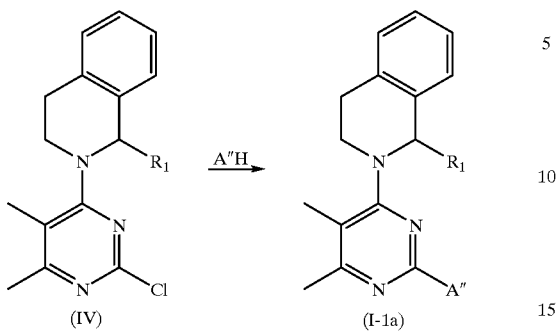

wherein $R_1$ is hydrogen or methyl; and A" is piperidin-1-yl or —NH—B, wherein B is $C_3$–$C_4$ alkyl, $C_3$–$C_4$ alkenyl, $C_3$–$C_7$ cycloalkyl, $C_1$–$C_3$ alkoxyethyl, phenylethyl which may be substituted or unsubstituted, 3-trifluoromethylphenylmethyl, or 1-naphthylmethyl.

In the process of Scheme 1, the compound of formula (IV) may be prepared by the same method as described in WO96/05177. The compound of A"H is commercially available (for example, from Aldrich Co. in U.S.A.).

As shown in Scheme 1, the pyrimidine compounds (IV) are reacted with A"H in the presence of an appropriate solvent and a base for 2 to 5 hours to give the compounds of formula (I-1a). Suitable solvents for this reaction may include dimethylformamide, p-dioxane, dimethylsulfoxide, and propyleneglycol. Suitable base for this reaction may include triethylamine, N,N-dimethylaniline, and pyridine. The reaction temperature preferably ranges from 80° C. to 140° C.

The compound of formula (I-1b) may be prepared by a process which comprises: chlorinating the compound of formula (V) to give a compound of formula (VI); and reacting the compound of formula (VI) with 1-$R_1$-1,2,3,4-tetrahydroisoquinoline in accordance with Scheme 2 described below.

Scheme 2

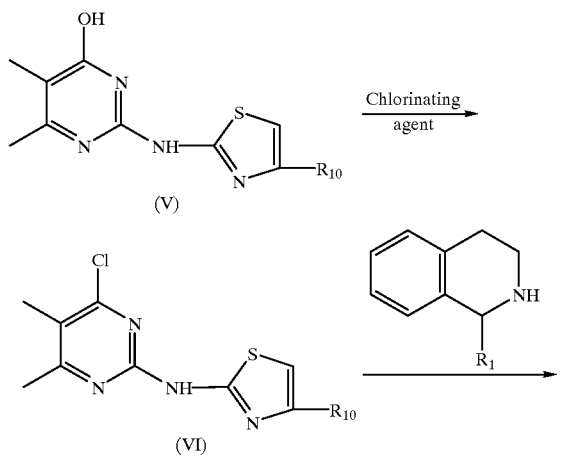

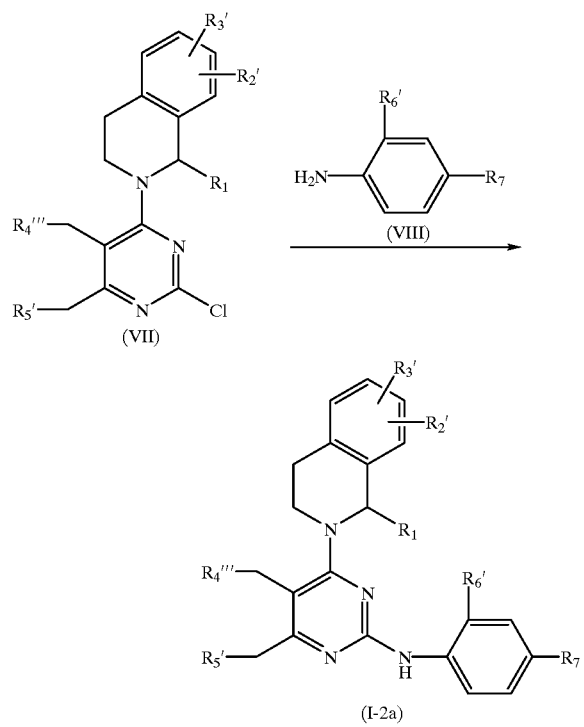

wherein $R_1$ is hydrogen or methyl; and $R_{10}$ is methyl or phenyl.

In the process of Scheme 2, the compound of formula (V) may be prepared by using a known process [see, e.g., *J. Med. Chem.*, 33, 543, (1990); and *J. Heterocyclic. Chem.*, 28, 231 (1991)].

The compound of formula (V) is chlorinated with chlorinating agent, e.g. phosphorous oxychloride, to give a compound of formula (VI). And then the compound of formula (VI) is reacted with 1-$R_1$-1,2,3,4-tetrahydroisoquinoline to give compounds of formula (I-1b).

Method for Preparation of the Formula (I-2)

The compound of formula (I-2a) may be prepared by reacting the compound (VII) with a compound of formula (VIII) in accordance with Scheme 3 described below.

Scheme 3 wherein $R_1$, $R_2'$, $R_3'$, $R_5'$, $R_6'$ and $R_7$ are the same as defined in formula (I-2); and $R_4'''$ is hydrogen or methyl.

In Scheme 3, the reaction may be accomplished under same conditions, e.g., solvent, base, reaction time, and temperature, as those of Scheme 1. And also, a compound of formula (I-2a) wherein $R_5'$ is hydroxy may be prepared by the demethylation of the corresponding compound of formula (I-2a) wherein $R_5'$ is methoxy.

In the process of Scheme 3, the compound of formula (VII) may be prepared in accordance with Scheme 4.

Scheme 4

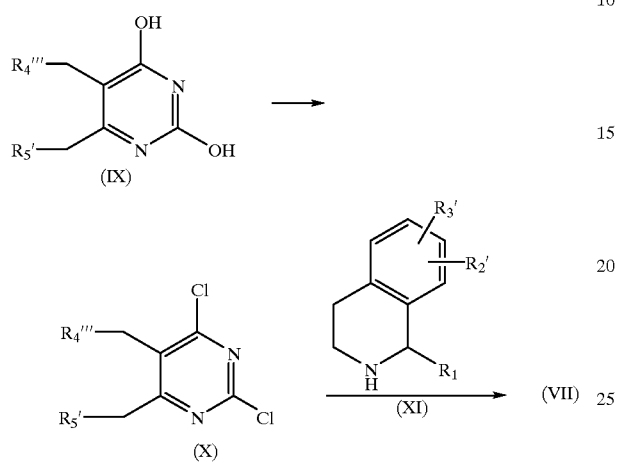

wherein $R_1$, $R_2'$, $R_3'$, $R_4'''$ and $R_5'$ are the same as defined in the above.

In the process of Scheme 4, the compounds of formula (IX) and (XI) may be prepared by using a known process [see, e.g., *J. Heterocyclic. Chem.*, 28, 231 (1991); *Org. Synth., Coll. Vol., IV*, 638, (1990); and European Patent No. 230,871].

The compound of formula (IX) is chlorinated with chlorinating agent, e.g. phosphorous oxychloride, to give a compound of formula (X). And then the compound of formula (X) is reacted with a compound of formula (XI) to give compounds of formula (VII). In the process of Scheme 4, the compound of formula (VII) wherein $R_5'$ is hydroxy is prepared by the demethylation of the corresponding compound of formula (VII) wherein $R_5'$ is methoxy.

As shown in Scheme 4, the pyrimidine compounds (X) are reacted with a compound of formula (XI) in the presence of an appropriate solvent and a base for 1 to 24 hours to give the compounds of formula (VII). Suitable solvents for this reaction may include dichloromethane, acetone, acetonitrile, and dimethylformarnmide. Suitable base for this reaction may include triethylamine, N,N-dimethylaniline, and pyridine. The reaction temperature preferably ranges from room temperature to 100° C.

The compounds of formula (VII) prepared as above are novel and useful as intermidiates for the preparation of the pyrimidine compounds of formula (I-2a). Therefore, the present invention encompasses, within its scope, the novel compounds of formula (VII) and process for the preparation thereof.

The compound of formula (I-2b) may be prepared from the compound of formula (XII) in accordance with Scheme 5-1 and 5-2 described below.

Scheme 5-1

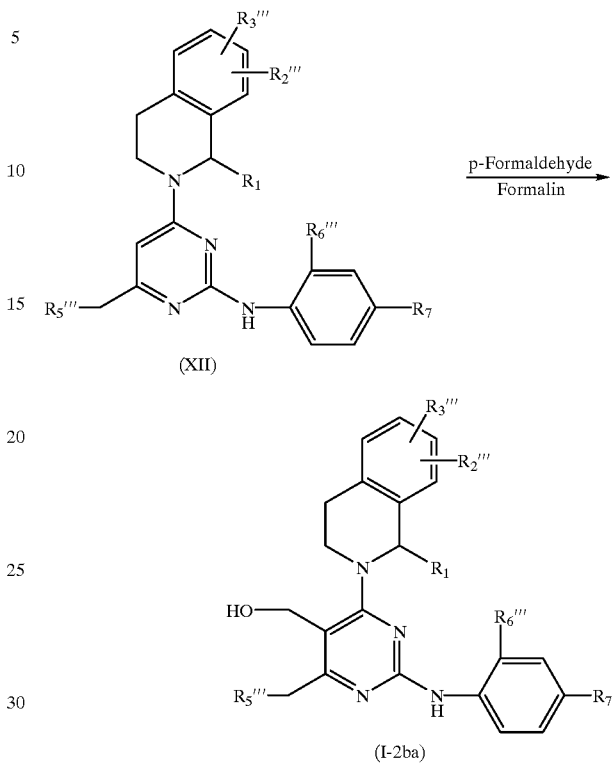

Scheme 5-2

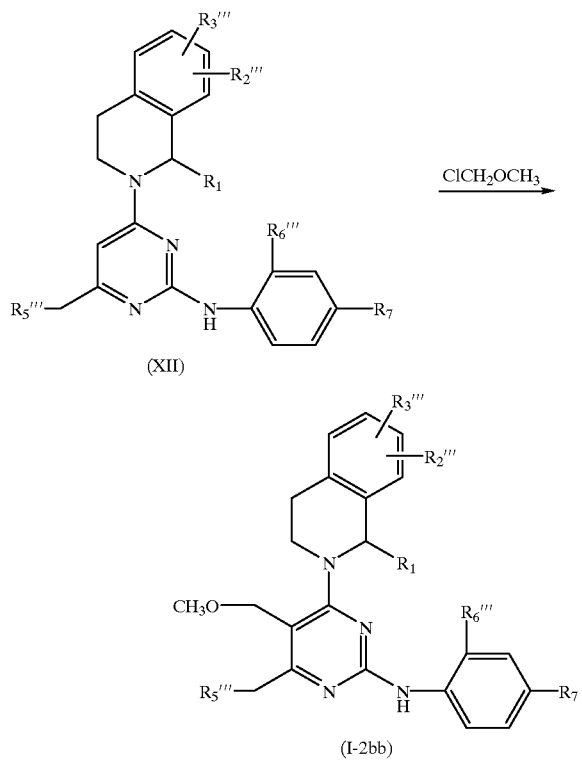

wherein $R_1$ and $R_7$ are the same as defined in formula (I-2); $R_2'''$, $R_3'''$, $R_5'''$ and $R_6'''$ are hydrogen or methyl, or one of $R_2'''$, $R_3'''$, $R_5'''$ and $R_6'''$ is hydroxy or methoxy.

The compound of formula (XII) may be prepared by the same method as described in WO96/05177 or WO97/42186.

As shown in Scheme 5-1, the pyrimidine compound (XII) is reacted with p-formaldehyde in formalin solution for 24 hours to give the compounds of formula (I-2ba). The reaction temperature preferably ranges from 20° C. to 150° C. And also, in Scheme 5-2, the pyrimidine compound (XII) is reacted with chloromethyl methyl ether in a sealed tube to give the compounds of formula (I-2bb).

Method for Preparation of the Formula (I-3)

The compound of formula (I-3) may be prepared by reacting the compound (XIII) with a compound of formula (XIV) in accordance with Scheme 6

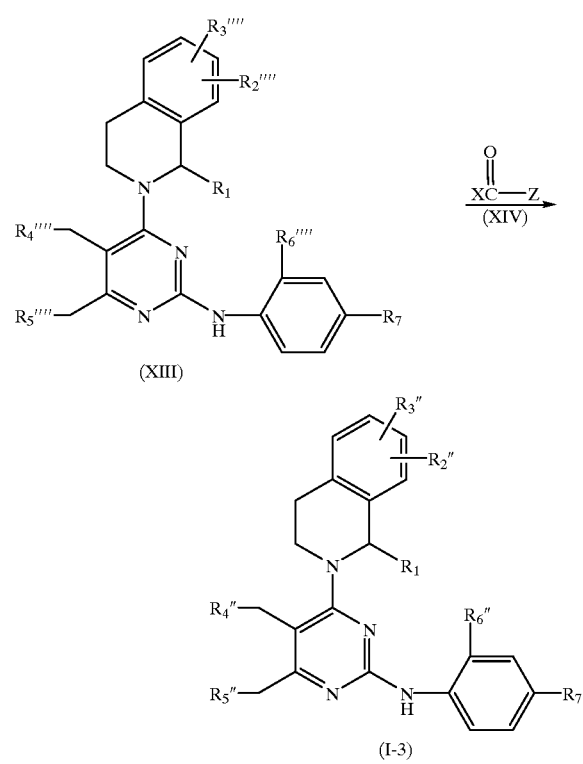

(XIII)

(I-3)

wherein $R_1$, $R_2''$, $R_3''$, $R_4''$, $R_5''$, $R_6''$, $R_7$ and Z are the same as defined in formula (I-3); one or two of $R_2''''$, $R_3''''$, $R_4''''$, $R_5''''$ and $R_6''''$ is hydroxy and the others are hydrogen ; and X is halogen or hydroxy.

When X is halogen in Scheme 6, the pyrimidine compounds (XIII) are reacted with a compound of formula (XIV) in the presence of an appropriate solvent and a base for 3 to 24 hours to give the compounds of formula (I-3). Suitable solvents for this reaction may include dimethylformamide and dichloromethane. Suitable base for this reaction may include triethylamine and pyridine. The reaction temperature preferably ranges from 0° C. to 50° C.

When X is hydroxy in Scheme 6, the pyrimidine compounds (XIII) are reacted with a compound of formula (XIV) in the presence of an appropriate solvent and a coupling agent for 3 to 24 hours to give the compounds of formula (I-3). Suitable solvents for this reaction may include dimethylformamide and dichloromethane. Suitable coupling agents for this reaction may include 1-hydroxybenzotriazole, 1-ethyl-3-(3-dimethylaminopropyl)carbodiimide and triethylamine. The reaction temperature preferably ranges from 0° C. to 50° C.

Method for Preparation of the Formula (I-4)

The compound of formula (I-4) may be prepared by reacting the compound (XV) with a compound of formula (XVI) in accordance with Scheme 7 described below.

Scheme 7

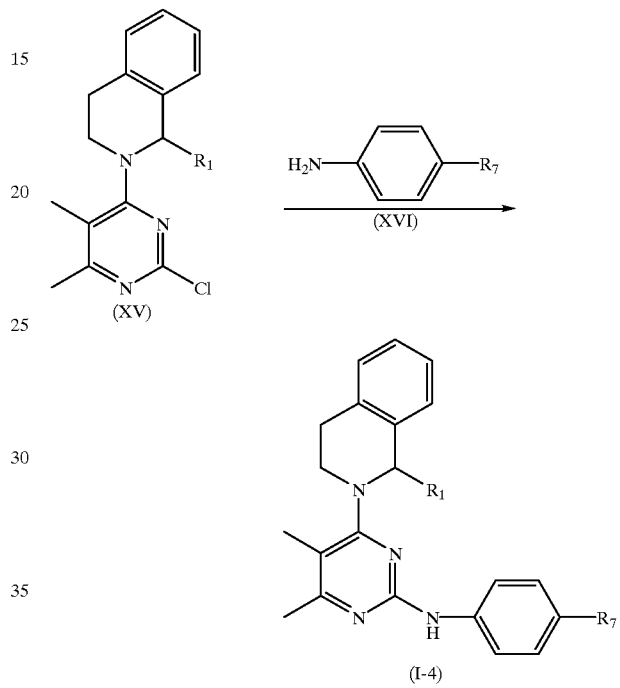

(XV)

(I-4)

wherein $R_1$ is hydroxymethyl or $C_1$–$C_3$ alkoxymethyl; and $R_7$ is hydrogen or halogen.

In Scheme 7, the reaction may be accomplished under same conditions, e.g., solvent, base, reaction time, and temperature, as those of Scheme 1.

The compounds of the present invention may be administered, either orally or intraperitoneally, in an effective amount ranging from 0.1 to 500 mg/kg, preferably from 1.0 to 100 mg/kg, into a subject patient per day.

The present invention further includes, within its scope, pharmaceutically acceptable salts of the compounds of formula (I). The non-toxic salts which fall within the scope of the present invention may include inorganic acid salts such as hydrochloride, sulfate, phosphate and nitrate, and organic acid salts such as tartrate, fumarate, citrate, mesylate and acetate.

The pharmaceutically acceptable salts may be prepared in accordance with a known method, e.g., by reacting the compounds of formula (I) with the acids mentioned above in the presence of a solvent, e.g., ethyl alcohol, dichloromethane, ethyl acetate and diethyl ether.

The present invention also includes within its scope pharmaceutical compositions comprising one or more of the inventive compounds as an active ingredient, in association with a pharmaceutically acceptable carrier, excipient and/or other additives, if necessary. The active ingredient present in the composition may range from 0.1% to 99.9% by weight thereof.

The following Examples are given for the purpose of illustration only, and are not intended to limit the scope of the invention. 2-Chloro-5,6-dimethyl-4-(1,2,3,4-tetrahydroisoquinolin-2-yl)pyrimidine and 2-chloro-5,6-dimethyl-4-(1-methyl-1,2,3,4-tetrahydroisoquinolin-2-yl) pyrimidine were prepared by the same method as described in WO96/05177.

Preparation 1: Substituted 1,2,3,4-tetrahydroisoquinoline

Preparation 1-1: 1-methyl-6-methoxy-1,2,3,4-tetrahydroisoquinoline

Step 1: N-(3-methoxyphenylethyl)acetamide 3-methoxyphenethylamine(50 g, 0.33 mol) was dissolved in a soultion of water(130 ml), dichloromethane(210 ml) and sodium hydroxide(17.6 g). Acetyl chloride(25.9 ml, 0.36 mol) was added dropwise at a room temperature to the mixture solution, which was then stirred for 1 hour. The separated dichloromethane layer was dried over anhydrous magnesium sulfate and then concentrated under a reduced pressure to give 63.6 g of the titled compound.

Step 2: 6-methoxy-1-methyl-3,4-dihydroisoquinoline

A mixture soultion of polyphosphoric acid (61.4 ml, 0.66 mol) and phosphorouspentoxide(28.0 g, 0.2 mol) was heated to 90° C. N-(3-methoxyphenylethyl) acetamide (63.6 g, 0.33 mol) was added to the mixture solution and then stirred for 2 hours at 110° C. The reaction mixture was poured into ice water, adjusted to alkali with potassium hydroxide, and then extracted with ethyl ether. The extract was dried over anhydrous magnesium sulfate and concentrated under a reduces pressure. The resulting residue was purified by a silica gel column chromatography, using a solution of methanol and dichloromethane (1:20) as a eluent, to give 54.0 g of the titled compound.

Step 3: 6-methoxy-1-methyl-1,2,3,4-tetrahydroisoquinoline 6-methoxy-1-methyl-3,4-dihydroisoquinoline (54.0 g, 0.31 mmol) was added to a suspension of sodium borohydride(5.8 g, 138 mmol) in ethanol. The mixture solution was stirred for 1 hour at a room temperature, cooled to below 5° C., acidified with diluted hydrochloric acid, adjusted to alkali with sodium hydroxide solution, and then extracted with ethyl acetate. The ethyl acetate layer was dried over anhydrous sodium sulfate and concentrated under a reduced pressure to give 45.4 g of the titled compound.

Preparation 1-2: 7-methoxy-1-methyl-1,2,3,4-tetrahydroisoquinoline

Step 1: N-(4-acetoxyphenylethyl)acetamide

The mixture solution of 4-hydroxyphenethylamine(6.86 g, 50 mmol), triethylamine(13.9 ml, 0.1 mol) and dichloromethane(50 ml) was cooled to 0° C. Acetylchloride (7.1 ml, 0.1 mol) was added dropwise to the mixture solution, which was then stirred for 2 hours at a room temperature, washed with 4N-hydrochloric acid, dried over anhydrous magnesium sulfate, and then concentrated to give 8.6 g of the titled compound.

Step 2: N-(4-hydroxyphenylethyl)acetamide

A solution of sodium hydroxide(2.3 g, 58 mmol) in water(20 ml) was cooled to 0° C. A solution of N-(4-acetoxyphenylethyl)acetamide(6.4 g, 29 mmol) in methanol (40 ml) was added dropwise to the soultion, stirred for 10 minutes, adjusted to pH 1 with hydrochloric acid, and then extracted 3 times with ethyl acetate. The extract was washed with water, dried over anhydrous magnesium sulfate and concentrated. The resulting oily residue was solidified with ethyl ether, filtered, and dried to give 4.4 g of the titled compound.

Step 3: N-(4-methoxyphenylethyl)acetamide

Potassium carbonate (3.5 g, 25.5 mol) and iodomethane (2.0 ml, 31.9 mmol) was added to a solution of N-(4-hydroxyphenylethyl)acetamide (4.4 g, 24.6 mmol) in ethanol(2.4 ml), which was then refluxed for 12 hours. The resulting solid was filtered and washed with ethanol. The filtrate was concentrated to give oily residue, which was diluted with ethyl acetate and washed with water. The separated organic layer was concentrated and the resulting solid was suspended in ethylether, filtered, and dried to give 2.9 g of the titled compound.

Step 4: 7-methoxy-1-methyl-1,2,3,4-tetrahydroisoquinoline

The same procedures as in Step 2 and 3 of Preparation 1-1 were repeated using N-(4-methoxyphenylethyl)acetamide (2.9 g, 14.9 mmol) to afford 0.96 g of the titled compound.

Preparation 1-3: 5-methoxy-1-methyl-1,2,3,4-tetrahydroisoquinoline

The same procedures as in Preparation 1-1 were repeated using 2-methoxyphenethylamine(5 ml, 34.16 mmol) to afford 6.45 g of the titled compound.

Preparation 1-4. 5,8-dimethoxy-1-methyl-1,2,3,4-tetrahydroisoquinoline

The same procedures as in Preparation 1-1 were repeated using 4,5-dimethoxyphenethylamine(5.0 g, 27.6 mmol) to afford 2.65 g of the titled compound.

Preparation 1-5. 1-methoxymethyl-1,2,3,4-tetrahydroisoquinoline

Step 1: Preparation of methoxyacetic acid

A mixture solution of methoxyacetonitrile(10 g, 0.14 mole) and conc. hydrochloric acid was stirred for 30 minutes, then refluxed for another 30 minutes, cooled to room temperature, diluted with water, extracted with diethyl ether. The ether solution was separated, dried over anhydrous sodium sulfate, concentrated under reduced pressure to afford 8.3 g of titled compound.

Step 2: Preparation of N-phenylethylmethoxyacetamide

Phenethylamine(11.6 ml, 92.1 mmol) was added dropwise to a solution of dicyclohexylcarbodiimide(19 g, 92.1 mmol), methoxyacetic acid(8.3 g, 92.1 mmol) in dichloromethane(50 ml) at room temperature. After addition was completed, the reaction mixture was stirred for 1 hour at room temperature and the resulting solid was filtered. The filtrate was washed with aqueous hydrochloric acid solution, and the organic layer was dried over anhydrous sodium sulfate, concentrated under reduced pressure to afford 8.15 g of the titled compound.

Step 3: Preparation of 1-methoxymethyl-1,2,3,4-tetrahydroisoquinoline

The same procedures as in Step 2 and 3 of Preparation 1-1 were repeated using N-phenylethylmethoxyacetamide(8.1 g, 41.9 mmol) to afford 2.6 g of the titled compound.

Preparation 2: 2,4-dichloro-6-methoxymethyl-5-methylpyrimidine

Step 1: Ethyl 2-methyl-3-oxo-4-methoxybutyrate

Zinc(18.1 ml, 275 mmol), methoxyacetonitrile(13.7 ml, 185 mmol), benzene (180 ml) and a catalytic amount of mercuric chloride were heated to reflux. A solution of ethyl 2-bromopropionate(35.9 ml, 275 mmol) in benzene(30 ml) was added dropwise, then reflux continued for further a hour, and cooled to a room temperature. 10% Aqueous sulfuric acid solution (325 ml) was added, and the organic layer was separated. The aqueous layer was further extracted with ethyl ether and the combined organic layers washed with water and aqueous sodium bicarbonate solution, then dried over anhydrous magnesium sulfate and concentrated under reduced pressure to give 29.3 g of the titled compound.

Step 2: 2-amino-4-hydroxy-6-methoxymethyl-5-methylpyrimidine

Ethyl 2-methyl-3-oxo4-methoxybutyrate(10.5 g, 60 mmol) was added slowly to a suspension of sodium methoxide (6.5 g, 120 mmol) in dimethylformamide(10 ml) while maintaining the reaction temperature under 20° C. A solution of guanidine(5.7 g, 60 mmol) in ethanol was added to a reaction mixture, which was then refluxed for 5 hours, cooled to a room temperature, and neutralized with conc. sulfuric acid. The resulting solid was filtered and dried to give 2.7 g of the titled compound.

Step 3: 2,4-dihydroxy-6-methoxymethyl-5-methylpyrimidine 2-amino-4-hydroxy-6-methoxymethyl-5-methylpyrimidine (2.7 g, 16 mmol) was added to 20% aqueous hydrochloric acid solution (7 ml), and heated to 70° C. A solution of sodium nitrite (2.3 g, 33.3 mmol) in water was added dropwise to a reaction mixture while maintaining the reaction temperature under 70° C. The reaction mixture was cooled to a room temperature. The resulting solid was filtered and dried to give 1.5 g of the titled compound.

Step 4: 2,4-dichloro-6-methoxymethyl-5-methylpyrimidine

A mixture solution of 2,4-dihydroxy-6-methoxymethyl-5-methyl pyrimidine (1.5 g, 8.8 mmol), phosphorous oxychloride(7ml) and N,N-dimethylaniline (0.9 ml) was refluxed for 3 hours, cooled to a room temperature, and then poured into ice water. The aqueous layer was extracted with dichloromethane. The resulting organic layer was dried, concentrated, and purified by a silica gel column chromatography to give 1.3 g of the titled compound.

Preparation 3. 4-morpholineacetic acid hydrochloride

Step 1: ethyl 4-morpholineacetate

Morpholine(1.65 ml, 18.9 mmol) was added dropwise to a soultion of ethyl bromoacetate(1 ml, 9.0 mmol) in benzene (9 ml). The reaction mixture was stirred for 2 hours at a room temperature, diluted with ethyl ether, and washed with saturated NaCl solution. The separated organic layer was dried over anhydrous sodium sulfate and concentrated under a reduced pressure to give 1.11 g of the titled compound as an oil. (Yield 71.2%)

NMR(CDCl$_3$): 1.3(t, 3H), 2.6(t, 4H), 3.2(s, 2H), 3.8(t, 4H), 4.2(q, 2H).

Step 2: 4-Morpholineacetic acid hydrochloride

Ethyl 4-morpholinoacetate (1.1 g, 6.3 mmol) was added to 3M hydrochloric acid solution (35 ml), refluxed for 2 hours, stirred for 1 day at a room temperature, and then concentrated under a reduced pressure. The resulting residue was dissolved in methanol and reconcentrated. The resulting solid was suspended in ethylether, filtered and dried under a reduced pressure to give 1.05 g of the titled compound. (Yield 91.7%)

NMR (DMSO-d6): 3.3(s, 4H), 3.9(s, 4H), 4.2(s, 2H).

Preparation 4. 4-benzylpiperazineacetic acid dihydrochloride

Step 1: ethyl 4-benzylpiperazineacetate

4-Benzylpiperazine(3.3 ml, 18.9 mmol) was added to a solution of ethyl bromoacetate(1 ml, 9.0 mmol) in benzene(9 ml), which was then stirred for 2 hours at a room temperature, diluted with ethyl ether, and washed with saturated NaCl solution. The separated organic layer was dried over anhydrous sodium sulfate and concentrated under reduced pressure to give 2.38 g of the titled compound. (Yield 100%).

NMR(CDCl$_3$): 1.3(t, 3H), 2.6(t, 8H), 3.2(s, 2H), 3.6(s, 2H), 4.2(q, 2H), 7.3(m, 5H).

Step 2: 4-benzylpiperazineacetic acid dihydrochloride

Ethyl 4-benzylpiperazineacetate (2.38 g, 9.0 mmol) was added to 3M hydrochloric acid solution(12 ml), refluxed for 2 hours, stirred for 1 day at a room temperature, and then concentrated under reduced pressure. The resulting residue was dissolved in methanol and reconcentrated. The resulting solid was suspended in ethyl ether, filtered and dried under a reduced pressure to give 2.14 g of the titled compound. (Yield 77.4%)

NMR(D2O): 3.3(s, 8H), 3.7(s, 2H), 4.0(s, 2H), 7.1(s, 5H).

Preparation 5. 1-piperidineacetic acid hydrochloride

Step 1:ethyl 1-piperidineacetate

Piperidine(1.87 ml, 18.9 mmol) was added dropwise to a solution of ethyl bromoacetate(1 ml, 9.0 mmol) in benzene(9 ml), stirred for 2 hours at a room temperature, diluted with ethyl ether, washed with saturated NaCl solution. The separated organic layer was dried over anhydrous sodium sulfate and concentrated under a reduced pressure to give 1.26 g of the titled compound. (Yield 81.8%)

NMR(CDCl$_3$): 1.3(t, 3H), 1.5(m, 2H), 1.7(m, 4H), 2.5(t, 4H), 3.2(s, 2H), 4.2(q, 2H).

Step 2: 1-piperidineacetic acid hydrochloride

Ethyl 1-piperidineacetate (1.26 g, 7.4 mmol) was added to 3M hydrochloric acid solution (12 ml), which was then refluxed for 2 hours, stirred for 1 day at a room temperature, then concentrated under a reduced pressure. The resulting residue was dissolved in methanol and reconcentrated. The resulting solid was suspended in ethyl ether, filtered and dried under a reduced pressure to give 0.87 g of the titled compound. (Yield 65.3%). NMR(D2O): 1.0(m, 2H), 1.4(m, 4H), 2.5(m, 2H), 3.1(m, 2H), 3.5(s, 2H).

EXAMPLE 1

5,6-dimethyl-2-(propylamino)-4-(1,2,3,4-tetrahydroisoquinolin-2-yl)pyrimidine hydrochloride Propylamine(0.44 g, 5.4 mmol) and triethylamine(0.38 ml, 2.7 mmol) were added to a mixture solution of 2-chloro-5,6-dimethyl-4-(1,2,3,4-tetrahydroisoquinolin-2-yl)pyrimidine(0.5 g, 1.8 mmol) in dimethylformamide(10 ml). The reaction mixture was stirred for 5 hours at 130° C., cooled to a room temperature, diluted with dichloromethane, and then washed with aqueous sodium hydroxide and water. The separated organic layer was dried over anhydrous magnesium sulfate, concentrated under a reduced pressure, and then purified by column chromatography to give free base form of the titled compound. Ethyl ether saturated with hydrochloric acid was added to a mixture solution of the free base form of the titled compound in ethyl ether. The resulting solid was filtered and dried to obtain 490 mg of the titled compound.

Yield: 81.8%; M.P.: 157–160° C.; $^1$H-NMR(CDCl3): δ 1.0(t, 3H), 1.7(m, 2H), 2.1(s, 3H), 2.4(s, 3H), 3.1(t, 2H), 3.4(q, 2H), 3.9(t, 2H), 4.8(s, 2H), 7.2(m, 4H), 7.9(s, 1H), 13.8(s, 1H).

EXAMPLE 2

5,6-dimethyl-2-(3-allylamino)-4-(1,2,3,4-tetrahydroisoquinolin-2-yl)pyrimidine hydrochloride After allylamine(0.20 ml, 2.7 mmol) and triethylamine (0.38 ml, 2.7 mmol) were added to a solution of 2-chloro-5,6-dimethyl-4-(1,2,3,4-tetrahydroisoquinolin-2-yl)pyrimidine(0.5 g, 1.8 mmol) in dimethylformamide, 170 mg of the titled compound was obtained in accordance with the same procedure as in Example 1.

Yield: 28.5%; M.P.: 192–194° C.; $^1$H-NMR(CDCl3): δ 2.2(s, 3H), 2.4(s, 3H), 3.1(t, 2H), 3.9(t, 2H), 4.1(t, 2H), 4.8(s, 2H), 5.3(q, 2H), 5.9(m, 1H), 7.2(m, 4H), 8.0(s, 1H), 14.0(s, 1H).

EXAMPLE 3

5,6-dimethyl-2-butylamino4-(1,2,3,4-tetrahydroisoquinolin-2-yl)pyrimidine hydrochloride After butylamine(0.53 ml, 5.4 mmol) and triethylamine (0.38 ml, 2.7 mmol) were added to a solution of 2-chloro-5,6-dimethyl-4-(1,2,3,4-tetrahydroisoquinolin-2-yl)pyrimidine(0.5 g, 1.8 mmol) in dimethylformamide, 300 mg of the titled compound was obtained in accordance with the same procedure as in Example 1.

Yield: 48.0%; M.P.: 110–113° C.; $^1$H-NMR(CDCl3): δ 1.0(t, 3H), 1.4(m, 2H), 1.6(m, 2H), 2.1(s, 3H), 2.4(s, 3H), 3.1(t, 2H), 3.5(q, 2H), 3.9(t, 2H), 4.8(s, 2H), 7.2(m, 4H), 7.9(s, 1H), 13.8(s, 1H).

EXAMPLE 4

5,6-dimethyl-2-isobutylamino-4-(1,2,3,4-tetrahydroisoquinolin-2-yl)pyrimidine hydrochloride After isobutylamine(0.27 ml, 2.7 mmol) and triethylamine(0.38 ml, 2.7 mmol) were added to a solution of 2-chloro-5,6-dimethyl-4-(1,2,3,4-tetrahydroisoquinolin-2-yl) pyrimidine(0.5 g, 1.8 mmol) in dimethylformamide, 180 mg of the titled compound was obtained in accordance with the same procedure as in Example 1.

Yield: 28.8%; M.P.: 169–172° C.; $^1$H-NMR(CDCl3): δ 1.0(d, 6H), 1.9(m, 1H), 2.1(s, 3H), 2.4(s, 3H), 3.1(t, 2H), 3.3(d, 2H), 3.9(t, 2H), 4.8(s, 2H), 7.2(m, 4H), 8.0(s, 1H), 13.9(s, 1H).

EXAMPLE 5

5,6-dimethyl-2-(2-methoxyethylamino)-4-(1,2,3,4-tetrahydroisoquinolin-2-yl)pyrimidine hydrochloride After methoxyethylamine(0.23 ml, 2.7 mmol) and triethylamine(0.38 ml, 2.7 mmol) were added to a solution of 2-chloro-5,6-dimethyl-4-(1,2,3,4-tetrahydroisoquinolin-2-yl)pyrimidine (0.5 g, 1.8 mmol) in dimethylformamide, 470 mg of the titled compound was obtained in accordance with the same procedure as in Example 1.

Yield: 74.8%; M.P.: 145–150° C.; $^1$H-NMR(CDCl3): δ 2.1(s, 3H), 2.4(s, 3H), 3.1(t, 2H), 3.4(s, 3H), 3.6(m, 4H), 3.9(t, 2H), 4.8(s, 2H), 7.2(m, 4H), 7.9(s, 1H), 14.0(s, 1H).

EXAMPLE 6

5,6-dimethyl-2-phenylethylamino4-(1,2,3,4-tetrahydroisoquinolin-2-yl)pyrimidine hydrochloride After phenethylamine(0.34 ml, 2.7 mmol) and triethylamine(0.38 ml, 2.7 mmol) were added to a solution of 2-chloro-5,6-dimethyl-4-(1,2,3,4-tetrahydroisoquinolin-2-yl) pyrimidine(0.5 g, 1.8 mmol) in dimethylformamide, 600 mg of the titled compound was obtained in accordance with the same procedure as in Example 1.

Yield: 84.4%; M.P.: 150–154° C.; $^1$H-NMR(CDCl3): δ 2.1(s, 3H), 2.4(s, 3H), 2.9(t, 2H), 3.1(t, 2H), 3.7(q, 2H), 3.9(t, 2H), 4.8(s, 2H), 7.2(m, 9H), 8.1(s, 1H).

EXAMPLE 7

5,6-dimethyl-2-(1-naphthylmethyl)amino-4-(1,2,3,4-tetrahydroisoquinolin-2-yl)pyrimidine hydrochloride After 1-naphthylmethylamine(0.40 ml, 2.7 mmol) and triethylamine (0.38 ml, 2.7 mmol) were added to a solution of 2-chloro-5,6-dimethyl-4-(1,2,3,4-tetrahydroisoquinolin-2-yl)pyrimidine(0.5 g, 1.8 mmol) in dimethylformamide, 680 mg of the titled compound was obtained in accordance with the same procedure as in Example 1.

Yield 87.7%; M.P.: 194–197° C.; $^1$H-NMR(CDCl3): δ 2.1(s, 3H), 2.4(s, 3H), 2.9(t, 2H), 3.8(t, 2H), 4.6(s, 2H), 5.1 (d, 2H), 7.0(m, 1H), 7.2(m, 3H), 7.5(m, 4H), 7.8(d, 1H), 7.9(d, 1H), 8.2(d, 1H), 8.5(s, 1H), 14.1(s, 1H).

EXAMPLE 8

5,6-dimethyl-2-(cyclohexylamino)-4-(1,2,3,4-tetrahydroisoquinolin-2-yl)pyrimidine hydrochloride After cyclohexylamine(0.31 ml, 2.7 mmol) and triethylamine(0.38 ml, 2.7 mmol) were added to a solution of 2-chloro-5,6-dimethyl-4-(1,2,3,4-tetrahydroisoquinolin-2-yl) pyrimidine(0.5 g, 1.8 mmol) in dimethylformamide, 340 mg of the titled compound was obtained in accordance with the same procedure as in Example 1.

Yield: 70.0%; M.P.: 173–177° C.; $^1$H-NMR(CDCl3): δ 1.4(m, 6H), 1.8(m, 2H), 1.9(m, 2H), 2.2(s, 3H), 2.4(s, 3H), 3.1(t, 2H), 3.9(t, 3H), 4.8(s, 2H), 7.2(m, 4H), 7.9(d, 1H), 13.7(s, 1H).

EXAMPLE 9

5,6-dimethyl-2-(cyclopentylamino)-4-(1,2,3,4-tetrahydroisoquinolin-2-yl)pyrimidine hydrochloride After cyclopentylamine(0.27 ml, 2.7 mmol) and triethylamine(0.38 ml, 2.7 mmol) were added to a solution of 2-chloro-5,6-dimethyl-4-(1,2,3,4-tetrahydroisoquinolin-2-yl) pyrimidine(0.5 g, 1.8 mmol) in dimethylformamide, 270 mg of the titled compound was obtained in accordance with the same procedure as in Example 1.

Yield: 41.8%; M.P.: 148–153° C.; $^1$H-NMR(CDCl3): δ 1.6(m, 4H), 1.8(m, 2H), 2.0(m, 2H), 2.1(s, 3H), 2.4(s, 3H), 3.1(t, 2H), 3.9(t, 2H), 4.2(q, 1H), 4.8(s, 2H), 7.2(m, 4H), 8.0(d, 1H), 13.7(s, 1H).

EXAMPLE 10

5,6-dimethyl-2-(piperidin-1-yl)-4-(1,2,3,4-tetrahydroisoquinolin-2-yl)pyrimidine hydrochloride After piperidine(0.27 ml, 2.7 mmol) and triethylamine (0.38 ml, 2.7 mmol) were added to a solution of 2-chloro-5,6-dimethyl-4-(1,2,3,4-tetrahydroisoquinolin-2-yl) pyrimidine(0.5 g, 1.8 mmol) in dimethylformamide, 260 mg of the titled compound was obtained in accordance with the same procedure as in Example 1.

Yield: 40.2%; M.P.: 77–82° C.; $^1$H-NMR(CDCl3): δ 1.7(s, 6H), 2.2(s, 3H), 2.7(s, 3H), 3.1(t, 2H), 3.9(t, 2H), 4.1(s, 4H), 4.8(s, 2H), 7.2(m, 4H), 12.9(bs, 1H).

EXAMPLE 11

5,6-dimethyl-2-propylamino-4-(1-methyl-1,2,3,4-tetrahydroisoquinolin-2-yl)pyrimidine hydrochloride After propylamine(0.43 ml, 5.22 mmol) and triethylamine (0.36 ml, 2.59 mmol) were added to a solution of 5,6-dimethyl-4-(1-methyl-1,2,3,4-tetrahydroisoquinolin-2-yl)-2-chloropyrimidine (0.5 g, 1.74 mmol) in dimethylformamide, 530 mg of the titled compound was obtained in accordance with the same procedure as in Example 1.

Yield: 63.0%; M.P.: 162–164° C.; $^1$H-NMR(CDCl3): δ 1.0(t, 3H), 1.7(q, 5H), 2.2(s, 3H), 2.4(s, 311), 2.9(m, 1H), 3.1–3.7(m, 5H), 4.3(m, 1H), 5.4(q, 1H), 7.2(m, 4H), 7.9(s, 1H), 13.8(s, 1H).

EXAMPLE 12

5,6-dimethyl-2-(3-allylamino)-4-(1-methyl-1,2,3,4-tetrahydroisoquinolin-2-yl)pyrimidine hydrochloride After allylamine(0.40 ml, 5.22 mmol) and triethylamine (0.36 ml, 2.59 mmol) were added to a solution of 2-chloro-5,6-dimethyl-4-(1-methyl-1,2,3,4-tetrahydroisoquinolin-2-yl) pyrimidine(0.5 g, 1.74 mmol) in dimethylformamide, 510 mg of the titled compound was obtained in accordance with the same procedure as in Example 1.

Yield: 85.0%; M.P.: 192–194° C.; $^1$H-NMR(CDCl3): δ 1.7(d, 3H), 2.2(s, 3H), 2.4(s, 3H), 4.6(s, 2H), 4.3(m, 1H), 5.1–5.5(m, 3H), 4.8(s, 2H), 5.9(m, 1H), 7.2(m, 4H), 8.0(s, 1H), 13.9(s, 1H).

EXAMPLE 13

5,6-dimethyl-2-butylamino-4-(1-methyl-1,2,3,4-tetrahydroisoquinolin-2-yl)pyrimidine hydrochloride After butylamine(0.52 ml, 5.22 mmol) and triethylamine (0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 430 mg of the titled compound was obtained in accordance with the same procedure as in Example 1.

Yield: 68.5%; M.P.: 105–107° C.; $^1$H-NMR(CDCl3): δ 1.0(t, 3H), 1.4–1.7(m, 4H), 1.7(d, 3H), 2.1(s, 3H), 2.4(s, 3H), 2.9(m, 1H), 3.2–3.7(m, 4H), 4.3(m, 1H), 5.4(q, qH), 7.3(m, 4H), 7.8(s, 1H), 13.8(s, 1H).

EXAMPLE 14

5,6-dimethyl-2-isobutylamino-4-(1-methyl-1,2,3,4-tetrahydroisoquinolin-2-yl)pyrimidine After isobutylamine(0.26 ml, 2.58 mmol) and triethylamine(0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 133 mg of the titled compound was obtained in accordance with the same procedure as in Example 1.

Yield 2 0.0%; M.P.: 93–95° C.; $^1$H-NMR(CDCl3): δ 0.9(d, 6H), 1.5(d, 3H), 1.9(m, 1H), 2.1(s, 3H), 2.3(s, 3H), 2.8(m, 1H), 3.1(t, 2H), 3.2(m, 1H), 3.5(m, 2H), 4.0(m, 1H), 5.1(q, 1H), 7.2(m, 4H).

EXAMPLE 15

5,6-dimethyl-2-(2-methoxyethylamino)-4-(1-methyl-1,2,3,4-tetrahydroisoquinolin-2-yl) pyrimidine hiydrochloride After 2-methoxyethylamine(0.23 ml, 2.7 mmol) and triethylamine(0.38 ml, 2.7 mmol) were added to a solution of 2-chloro-5,6-dimethyl-4-(1-methyl-1,2,3,4-tetrahydroisoquinolin-2-yl)pyrimidine (0.5 g, 1.74 mmol) in dimethylformamide, 320 mg of the titled compound was obtained in accordance with the same procedure as in Example 1.

Yield: 50.7%; M.P.: 64–67° C.; $^1$H-NMR(CDCl3): δ 1.6(d, 3H), 2.1(s, 3H), 2.4(s, 3H), 2.9(m, 1H), 3.3(m, 1H), 3.4(s, 3H), 3.6(m, 5H), 4.3(m, 1H), 5.4(q, 1H), 7.2(m, 4H), 7.8(s, 1H), 13.8(s, 1H).

EXAMPLE 16

5,6-dimethyl-2-phenylethylamino-4-(1-methyl-1,2,3,4-tetrahydroisoquinolin-2-yl)pyrimidine hydrochloride After 2-phenethylamine(0.33 ml, 2.61 mmol) and triethylamine(0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 500 mg of the titled compound was obtained in accordance with the same procedure as in Example 1.

Yield: 70.2%; M.P.: 124–127° C.; $^1$H-NMR(CDCl3): δ 1.7(d, 3H), 2.1(s, 3H), 2.4(s, 3H), 3.0(m, 3H), 3.3(m, 1H), 3.7(m, 3H), 4.3(m, 1H), 5.4(q, 1H), 7.2(m, 9H), 8.0(s, 1H), 13.8(s 1H).

EXAMPLE 17

5,6-dimethyl-2-(1-naphthylmethyl)amino-4-(1-methyl-1,2,3,4-tetrahydroisoquinolin-2-yl) pyrimidine hydrochloride After 1-naphthylmethylamine(0.38 ml, 2.61 mmol) and triethylamine (0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 630 mg of the titled compound was obtained in accordance with the same procedure as in Example 1.

Yield: 81.4%; M.P.: 179–182° C.; $^1$H-NMR(CDCl3): δ 1.4(d, 3H), 2.1(s, 3H), 2.4(s, 3H), 2.7(m, 1H), 3.0(m, 1H), 3.4(m, 1H), 4.1(m, 1H), 5.1(m, 3H), 6.8(d, 1H), 7.1(m, 3H), 7.5(m, 4H), 7.8(d, 1H), 7.9(d, 1H), 8.1(d, 1H), 8.5(s, 1H), 14.0(s, 1H).

EXAMPLE 18

5,6-dimethyl-2-(3-trifluoromethylphenylmethyl)amino-4-(1-methyl-1,2,3,4-tetrahydroisoquinolin-2-yl)pyrimidine hydrochloride After 3-trifluoromethylbenzylamine(0.30 ml, 2.61 mmol) and triethylamine(0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 630 mg of the titled compound was obtained in accordance with the same procedure as in Example 1.

Yield: 78.2%; M.P.: 190–192° C.; $^1$H-NMR(CDCl3): δ 1.5(d, 3H), 2.1(s, 3H), 2.4(s, 3H), 2.8(m, 1H), 3.1(m, 1H), 3.5(m, 1H), 4.2(m, 1H), 4.6(d, 2H), 5.2(q, 1H), 7.1(m, 4H), 7.6(m, 4H), 8.6(s, 1H), 14.0(s, 1H).

EXAMPLE 19

5,6dimethyl-2-(cyclopentylamino)-4-(1-methyl-1,2,3,4tetrahydroisoquinolin-2-yl)pyrirnidine hydrochloride After cyclopentylamine(0.26 ml, 2.61 mmol) and triethylamine(0.36 ml, 2.59 mmol) were added to a solution of 2-chloro-5,6-dimethyl-4-(1-methyl-1,2,3,4-tetrahydroisoquinolin-2-yl)pyrimidine (0.5 g, 1.74 mmol) in dimethylformamide, 550 mg of the titled compound was obtained in accordance with the same procedure as in Example 1.

Yield 84.8%; M.P.: 150–153° C.; $^1$H-NMR(CDCl3): δ 1.6(d, 6H), 1.7–2.0(m, 5H), 2.1(s, 3H), 2.4(s, 3H), 2.9(m, 1H), 3.1(m, 1H), 3.2(m, 1H), 3.6(m, 1H), 4.2(m, 2H), 5.4(q, 1H), 7.2(m, 4H), 8.0(d, 1H), 13.6(s, 1H).

EXAMPLE 20

5,6-dimethyl-2-(cyclohexylamino)-4-(1-methyl-1,2,3,4-tetrahydroisoquinolin-2-yl)pyrimidine hydrochloride After cyclohexylamine(0.30 ml, 2.61 mmol) and triethylamine(0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 550 mg of the titled compound was obtained in accordance with the same procedure as in Example 1.

Yield 81.7%; M.P.: 140–144° C.; $^1$H-NMR(CDCl3): δ 1.4(m, 5H), 1.6(d, 3H), 2.0(m, 5H), 2.2(s, 3H), 2.4(s, 3H), 2.9(m, 1H), 3.2(m, 1H), 3.6(m, 1H), 3.9(bs, 1H), 4.3(m, 1H), 5.4(q, 1H), 7.2(m, 4H), 7.8(d, 1H), 13.6(s, 1H).

EXAMPLE 21

5,6-dimethyl-2-(piperidin-1-yl)-4-(1methyl-1,2,3,4-tetrahydroisoquinolin-2-yl)pyrimidine hydrochloride After piperidine(0.26 ml, 2.61 mmol) and triethylamine (0.36 ml, 2.59 mmol) were added to a solution of 2-chloro-5,6-dimethyl-4-(1-methyl-1,2,3,4-tetrahydroisoquinolin-2-yl)pyrimidine(0.5 g, 1.74 mmol) in dimethylformamide, 490 mg of the titled compound was obtained in accordance with the same procedure as in Example 1.

Yield 75.5%; M.P.: 103–107° C.; $^1$H-NMR(CDCl3): δ 1.6(d, 3H), 1.7(s, 6H), 2.1(s, 3H), 2.7(s, 3H), 2.9(m, 1H), 3.2(m, 1H), 3.5(m, 1H), 4.0(s, 4H), 4.3(m, 1H), 5.4(q, 1H), 7.2(m, 4H), 13.2(s, 1H).

EXAMPLE 22

5,6-dimethyl-2-(4-methylthiazol-2-yl)amino-4-(1-methyl-1,2,3,4-tetrahydroisoquinolin-2-yl) pyrimidine hydrochloride Step 1: 2-guanyl-4-methylthiazole hydrochloride After refluxing a solution of 2-aminothiourea(11.08 g, 93.77 mmol) in ethanol(85 ml), chloroacetone(8.2 ml, 103.15 mmol) was added dropwise to the solution. The reaction mixture was stirred for 4 hours, and then stand for 1 day, while maintaining the temperature under 10° C. The resulting solid was filtered, washed with ethyl ether, and then dried under a reduced pressure to give 11.7 g of the titled compound. (Yield: 64.7%)

Step 2: 5,6-dimethyl-2-(4-methylthiazol-2-yl)amino-4-hydroxypyrimidine

A mixture solution of ethyl 2- methylacetoacetate(0.7 ml, 5.19 mmol), sodium methoxide (0.56 g, 10.38 mmol), 2-guanyl4-methylthiazole (1.0 g, 5.19 mmol), and methanol (13 ml) was refluxed and then stirred for 3 hours. The reaction mixture was cooled to a room temperature and then adjusted to pH 7 with hydrochloric acid. The resulting solid wag filtered, washed with water and methanol, and then dried under a reduced pressure to give 0.98 g of the titled compound. (Yield: 32%)

Step 3: 5,6-dimethyl-2-(4-methylthiazol-2-yl)amino-4-chloropyrimidine

The mixture solution of 5,6-dimethyl-2-(4-methylthiazol-2-yl)amino-4-hydroxypyrimidine (1.15 g, 4–78 mmol), phosphorus oxychloride(7 ml), and dimethylformamide(5 ml) was heated to 70° C. for 30 minutes, cooled to a room temperature and then poured into ice water. The aqueous layer was extracted with dichloromethane, washed with 1N sodium hydroxide solution, and then washed with water. The separated organic layer was concentrated and the residual oil was suspended in a mixture solution of ethyl ether and hexane. The resulting solid was filtered and dried to give 0.42 g of the titled compound. (Yield: 33.9%)

Step 4: 5,6-dimethyl-2-(4-methylthiazol-2-yl)amino-4-(1-methyl-1,2,3,4-tetrahydroisoquinolin-2-yl)pyrimidine hydrochloride A soultion of 5,6-dimethyl-2-(4-methylthiazol-2-yl)amino-4-chloropyrimidine (0.41 g, 1.6 mmol) 1-methyl-1,2,3,4-tetrahydioiasoquinoline(0.47 ml, 3.2 mmol) and dimethylformamide(2ml) was he a ted to 120° C. for 6 hours. diluted with dichiloromethane, and then washed with water. The separated organic layer was dried over anhydrous magnesium sulfate and concentrated. The resulting residue was purified by slica gel column chromatography, using a solution of ethylacetate and hexane (1:2) as a eluent. After evaporating of the solvent, the residual oil was dissolved in a solution of ethyl ether and ethyl acetate and treated with ethylether saturated with hydrochloric acid. The resulting solid was filtered and dried to give 0.5 g of the titled compound.

Yield :78%; M.P.: 183–185° C.; $^1$H-NMR(DMSO-d6): δ 1.6(d, 3H), 2.2(s, 3H), 2.3(s, 3H), 2.4(s, 3H), 2.9(m, 1H), 3.2(m, 1H), 3.7(m, 1H), 4.4(m, 1H), 5.6(m, 1H), 6.7(s, 1H), 7.2(m, 4H), 7.4(m, 1H), 8.0(bs, 1H), 12.8(bs, 1H).

EXAMPLE 23

5,6-dimethyl-2-(4-methylthiazol-2-yl)amino-4-(1,2,3,4-tetrahydroisoquinolin-2-yl)pyrimidine hydrochloride The same procedures as in Step 4 of Example 22 were repeated using 5,6-dimethyl-2-(4-methylthiazol-2-yl)amino-4-chloropyrimidine(0.85 g, 3.34 mmol), 1,2,3,4-tetrahydroisoquinoline(0.42 ml, 3.34 mmol) and dimethylformamide (5 ml) to afford 140 mg of the titled compound.

Yield: 10.8%; M.P.: 257–262° C.; $^1$H-NMR(DMSO-d6): δ 2.2(s, 3H), 2.3(s, 3H), 2.4(s, 3H), 3.1(s, 2H), 4.0(s, 2H), 6.7(s, 1H), 5.6(m, 1H), 7.2(d, 4H).

EXAMPLE 24

5,6-dimethyl-2-(4-phenylthiazol-2-yl)amino-4-(1,2,3,4-tetrahydroisoquinolin-2-yl)pyrimidine hydrochloride Step 1: 2-guanyl-4-phenylthiazole hydrobromide The same procedures as in Step 1 of Example 22 were repeated using 2-aminothiourea(20 g, 169.26 mmol), 2-bromoacetophenone(35.38 g, 1.05 eq.) and ethanol (170 mol) to afford 49.9 g of the titled compound. (Yield: 98.5%)

Step 2: 5,6-dimethyl-2-(4-phenylthiazol-2-yl)amino-4-hydroxypyrimidine

The same procedures as in Step 2 of Example 22 were repeated using 2-guanyl-4-phenylthiazole hydrobromide (30.5 g, 101.94 mmol) and ethyl 2-nmethylacetoaetate(14.4 ml, 101.94 mmol) to afford 5.6 g of the titled compound. (Yield: 18.4%)

Step 3: 5,6-dimethyl-2-(4-phenylthiazol-2-yl)amino-4-chloropyrimidine

The same procedures as in Step 3 of Example 22 were repeated using 5,6-dimethyl-2-(4-phenylthiazol-2-yl)amino-4-hydroxypyrimidine (5.6 g, 18.77 mmol) and phosphorus oxychloride(7 ml) to afford 3.0 g of the titled compound. (Yield: 50%)

Step 4: 5,6-dimethyl-2-(4-phenylthiazol-2-yl)amino-4-(1,2,3,4-tetrahydroisoquinolin-2-yl)pyrimidine hydrochloride A mixture solution of 5,6-dimethyl-2-(4-methylthiazol-2-yl)amino-4-chloropyrimidine (0.36 g, 1.14 mmol), 1,2,3,4-tetrahydroisoquinoline(0.16 ml, 1.25 mmol), triethylamine (0.16 ml, 1.25 mmol) and propyleneglycol(1.1 ml) was heated to 140° C., stirred for 5 hours, diluted with dichloromethane, and then washed with water. The separated organic layer was dried over anhydrous magnesium sulfate and concentrated. The resulting residue was purified by a silica gel column chromatography using, a soluton of ethyl acetate and hexane (1:3) as a eluent. After evaporating of the solvent, the residual oil was dissolved in a solution of ethyl ether and ethyl acetate and treated with ethylether saturated with hydrochloric acid. The resulting solid was filtered and dried to give 0.18 g of the titled compound.

Yield: 35%; M.P.: 283–285° C.; $^1$H-NMR(DMSO-d6): δ 2.2(s, 3H), 2.4(s, 3H), 3.1(t, 2H), 3.7(t, 2H), 4.7(s, 2H), 7.0(s, 1H), 7.3(m, 7H), 7.9(d, 2H).

EXAMPLE 25

6-methoxymethyl-5-methyl-2-(2-methylethylamino)-4-(1,2,3,4-tetrahydroisoquinolin-2-yl)pyrimidine hydrochloride Step 1: 6-methoxymethyl-5-methyl-chloro-4-(1,2,3,4-tetrahydroisoquinolin-2-yl) pyrimidine 1,2,3,4-tetrahydroisoquinoline(0.9 ml, 6.9 mmol) was added dropwise to a solution of 2,4-dichloro-6-methoxymethyl-5-methylpyrimidine(1.3 g, 6.3 mmol) and triethylamine(0.96 ml, 6.9 mmol) in dimethylformamide and stirred for 5 hours at a room temperature. The reaction mixture was diluted with dichloromethane and washed with water and aqueous sodium hydroxide solution. The organic layer was dried over anhydrous sodium sulfate and concentrated under a reduced pressure. The resulting residue was purified by a silica gel column chromatography to give 1.8 g of the titled compound. (Yield: 94.0%)

Step 2: 6-methoxymethyl-5-methyl-2-(2-methylphenylamino)-4-(1,2,3,4-tetrahydro isoquinolin-2-yl)pyrimidine hydrochloride o-Toluidine(0.48 ml, 4.5 mmol) and triethylamine were added to a solution of 6-methoxymethyl-5-methyl-2-chloro-4-(1,2,3,4-tetrahydroisoquinolin-2-yl)pyrimidine (0.9 g, 3 mmol) in dimethylformamide(5 ml) and stirred for 5 hours at 130° C. The reaction mixture was cooled to a room temperature, diluted with dichloromethane, and washed with aqueous sodium hydroxide and water. The organic layer was dried over anhydrous magnesium sulfate, concentrated, and the residual oil was purified by column chromatography. The purified compound was dissolved in ethyl ether. Ethyl ether saturated with hydrochloric acid was added to a mixture solution. The resulting solid was filtered and dried to give 400 mg of the titled compound.

Yield: 32.5%; M.P.: 178–183° C.; $^1$H-NMR(CDCl3): δ 2.2(s, 3H), 2.4(s, 3H), 2.9(m, 2H), 3.6(s, 3H), 3.9(m, 2H), 4.5(s, 2H), 4.8(s, 2H), 7.0–7.1(m, 7H), 7.6(m, 1H), 10.2(s, 1H) 14(s, 1H).

EXAMPLE 26

6-methoxymethyl-5-methyl-2-(4-fluorophenylamino)-4-(1,2,3,4-tetrahydroisoquinolin-2-yl)pyrimidine hydrochloride After 4-fluoroaniline(0.43 ml, 4.5 mmol) and triethylamine(0.63 ml, 4.5 mmol) were added to a solution of 6-methoxymethyl-5-methyl-2-chloro-4-(1,2,3,4-tetrahydroisoquinolin-2-yl)pyrimidine (0.9 g, 3 mmol) in dimethylformamide (5 ml), 190 mg of the titled compound was obtained in accordance with the same procedure as in Step 2 of Example 25.

Yield: 15%; M.P.: 226–237° C.; $^1$H-NMR(CDCl3): δ 2.2(s, 3H), 3.1(m, 2H), 3.6(s, 3H), 3.9(m, 2H), 4.5(s, 2H), 4.8(s, 2H), 7.0–7.3(m, 6H), 7.6(m, 2H), 11.2(s, 1H), 13.5(s, 1H).

EXAMPLE 27

6-methoxymethyl-5-methyl-2-(4-fluoro-2-methylphenylamino)-4-(1,2,3,4-tetrahydroisoquinolin-2-yl)pyrimidine hydrochloride After 2-methyl-4-fluoroaniline(0.51 g, 4.5 mmol) and triethylamine (0.63 ml, 4.5 mmol) were added to a solution of 6-methoxymethyl-5-methyl-2-chloro-4-(1,2,3,4-tetrahydroisoquinolin-2-yl) pyrimidine(0.9 g, 3 mmol) in dimethylformamide (5 ml), 750 mg of the titled compound was obtained in accordance with the same procedure as in Step 2 of Example 25.

Yield : 60%; M.P.: 157–159° C.; $^1$H-NMR(CDCl3): δ 2.2(s, 3H), 2.4(s, 3H), 2.9(m, 2H), 3.6(s, 3H), 3.8(m, 2H), 4.5(s, 2H), 4.8(s, 2H), 6.8–7.3(m, 6H), 7.5(m, 1H), 10.2(s, 1H), 14.0(s, 1H).

EXAMPLE 28

6-methoxymethyl-5-methyl-2-(4-fluorophenylamino)-4-(1-methyl-1,2,3,4-tetrahydroisoquinolin-2-yl)pyrimidine hydrochloride Step 1: 6-methoxymethyl-5-methyl-2-chloro-4-(1-methyl-1,2,3,4tetrahydroisoquinolin-2-yl)pyrimidine The same procedures as in Step 1 of Example 25 were repeated using 2,4-dichloro-6-methoxymethyl-5-methylpyrimidine(1.3 g, 6.3 mmol) and 1-methyl-1,2,3,4-tetrahydroisoquinoline(1.02 g, 6.93 mmol) to afford 1.2 g of the titled compound. (Yield: 60%)

Step 2: 6-methoxymethyl-5-methyl-2-(4-fluorophenylamino)-4-(1-methyl-1,2,3,4-tetrahydroisoquinolin-2-yl)pyrimidine hydrochloride After 4-fluoroaniline(0.43 ml, 4.5 mmol) and triethylamine(0.63 ml, 4.5 mmol) were added to a solution of 6-methoxymethyl-5-methyl-2-chloro-4-(1-methyl-1,2,3,4-tetrahydroisoquinolin-2-yl)pyrimidine (0.96 g, 3 mmol) in dimethylformamide(5 ml), 600 mg of the titled compound was obtained in accordance with the same procedure as in Step 2 of Example 25.

Yield 47%; M.P.: 228–233° C.; $^1$H-NMR(CDCl3): δ 1.6(d 3H), 2.2(s, 3H), 2.9(d, 1H), 3.1(m, 1H), 3.5–3.7(s+m, 4H), 4.3(bd, 2H), 4.5(dd, 2H), 5.4(q, 1H), 6.9–7.3(m, 6H), 7.6(m, 2H), 11.2(s, 1H), 13.3(bs, 1H).

EXAMPLE 29

6-methoxymethyl-5-methyl-2-(2-methyl-4-fluorophenylamino)-4-(1-methyl-1,2,3,4-tetrahydroisoquinolin-2-yl)pyrimidine hydrochloride After 2-methyl-4-fluoroaniline(0.62 ml, 4.5 mmol) and triethylamine (0.63 ml, 4.5 mmol) were added to a solution of 6-methoxymethyl-5-methyl-2-chloro4-(1-methyl-1,2,3,4-tetrahydroisoquinolin-2-yl)pyrimidine(0.96 g, 3 mmol) in dimethylformamide(5 ml), 600 mg of the titled compound was obtained in accordance with the same procedure as in Step 2 of Example 25.

Yield: 47%; M.P.: 175–177° C.; $^1$H-NMR(CDCl3): δ 1.5(d 3H), 2.2(s, 3H), 2.4(s, 3H), 2.8(d, 1H), 3.1(m, 1H), 3.4–3.7(s+m, 4H), 4.3(m, 1H), 4.5(s, 2H), 5.4(qq, 1H), 6.8–7.6(m, 7H), 10.0(ss, 1H), 13.9(ss, 1H).

EXAMPLE 30

6-methoxymethyl-5-methyl-2-(2-methylphenylamino)-4-(1-methyl-1,2,3,4-tetrahydroisoquinolin-2-yl)pyrimidine hydrochloride After o-toluidine(0.32 ml, 3.0 mmol) and triethylamine (0.63 ml, 4.5 mmol) were added to a solution of 6-methoxymethyl-5-methyl-2-chloro-4-(1-methyl-1,2,3,4-tetrahydroisoquinolin-2-yl)pyrimidine(0.96 g, 3 mmol) in dimethylformamide(5 ml), 250 mg of the titled compound was obtained in accordance with the same procedure as in Step 2 of Example 25.

Yield: 20%; M.P.: 247–250° C.; $^1$H-NMR(CDCl3): δ 1.5(d 3H), 2.2(s, 3H), 2.4(s, 3H), 2.8(d, 1H), 3.1(m, 1H), 3.5–3.7(s+m, 4H), 4.3(bd, 1H), 4.5(s, 2H), 5.3(q, 1H), 7.0–7.3(m, 7H), 7.6(d, 1H), 10.2(s, 1H), 13.9(bs, 1H).

EXAMPLE 31

6-methoxymethyl-5-methyl-2-phenylamino-4-(1-methyl-1,2,3,4-tetrahydroisoquinolin-2-yl) pyrimidine hydrochloride After aniline (2.41 ml, 26.4 mmol) and triethylamine(3.68 ml, 26.4 mmol) were added to a solution of 6-methoxymethyl-5-methyl-2-chloro-4-(1-methyl-1,2,3,4-tetrahydroisoquinolin-2-yl)pyrimidine(7 g, 22 mmol) in dimethylformamide (20 ml), 4.1 g of the titled compound was obtained in accordance with the same procedure as in Step 2 of Example 25.

Yield: 45%; M.P.: 208–212° C.; $^1$H-NMR(CDCl3): δ 1.6(d, 3H), 2.2(s, 3H), 2.8(d, 1H), 3.1–3.3(m, 1H), 3.4–3.7 (s+m, 4H), 4.35(bd, 1H), 4.50(dd, 2H), 5.45(q, 1H), 6.80–7.50(m, 7H), 7.65(d, 2H), 11.10(s, 1H), 13.50(bs, 1H).

EXAMPLE 32

6-hydroxymethyl-5-methyl-2-phenylamino-4-(1-methyl-1,2,3,4-tetrahydroisoquinolin-2-yl) pyrimidine hydrochloride A solution of 6-methoxymethyl-5-methyl-2-phenylamino-4-(1-methyl-1,2,3,4-tetrahydroisoquinolin-2-yl)pyrimidine(4.0 g, 9.7 mmol) in dichloromethane (50 ml) was cooled under 0° C. Boron tribromide (1M-dichloromethane solution, 38.8 ml, 38.8 mmol) was added dropwise to the solution. The reaction mixture was stirred for 30 minutes at 0° C. and poured into ice water. The separated dichloromethane layer was washed with aqueous sodium bicarbonate solution, dried over anhydrous sodium sulfate, concentrated under a reduced pressure. Ethyl ether was added to the resulting residue to give a solid, which was then dissolved in ethanol and treated with ethyl ether saturated with hydrochloric acid to give 2.3 g of the titled compound.

Yield: 59.5%; M.P.: 193–198° C.; $^1$H-NMR(DMSO-d6): δ 1.6(d 3H), 2.2(s, 3H), 2.9(d, 1H), 3.1(m, 1H), 3.0–3.2(m, 1H), 4.3(bd, 1H), 4.6(q, 2H), 5.5(q, 1H), 7.0–7.4(m, 5H), 7.4(t, 2H), 7.6(d, 2H).

EXAMPLE 33

6-hydroxymethyl-5-methyl-2-(4-fluorophenylamino)-4-(1-methyl-1,2,3,4-tetrahydroisoquinolin-2-yl)pyrimidine hydrochloride The same procedures as in Example 32 were repeated using 6-methoxymethyl-5-methyl-2-(4-fluorophenylamino)-4-(1-methyl-1,2,3,4-tetrahydroisoquinolin-2-yl)pyrimidine(0.25 g, 0.58 mmol) and borone tribromide(1M-dichloromethane solution, 2.5 ml, 2.5 mmol) to afford 0.1 g of the titled compound.

Yield: 29%; M.P.: 223–226° C.; $^1$H-NMR(DMSO-d6): δ 1.6(d, 3H), 2.2(s, 3H), 2.9(d, 1H), 3.0–3.2(m, 1H), 3.6–3.8(t, 1H), 4.3(bd, 1H), 4.7(q, 2H), 5.5(q, 1H), 7.0–7.4(m, 6H), 7.5–7.7(m, 2H).

EXAMPLE 34

6-hydroxymethyl-5-methyl-2-(2-methylphenylamino)-4-(1-methyl-1,2,3,4-tetrahydroisoquinolin-2-yl)pyrimidine hydrochloride The same procedures as in Example 32 were repeated using 6-methoxymethyl-5-methyl-2-(2-methylphenylamino)-4-(1-methyl-1,2,3,4-tetrahydroisoquinolin-2-yl)pyrimidine(9.7 g, 22.1 mmol) and borone tribromide(1M-dichloromethane solution, 88.4 ml, 88.4 mmol) to afford 4.7 g of the titled compound.

Yield: 54.7%; M.P.: 225–227° C.; $^1$H-NMR(DMSO-d6): δ 1.5(d, 3H), 2.1(s, 3H), 2.3(s, 3H), 2.8(bd, 1H), 3.0(m, 1H), 3.5(m, 1H), 4.2(m, 1H), 4.6(q, 2H), 5.3(q, 1H), 7.1(s, 5H), 7.3(d, 2H), 7.7(d, 1H), 10.0(s, 1H), 12.3(s, 1H).

EXAMPLE 35

5,6dimethyl-2-(4-fluorophenylamino)-4-(6-methoxy-1-methyl-1,2,3,4-tetrahydroisoquinolin-2-yl) pyrimidine hydrochloride Step 1: 5,6-dimethyl-2-chloro-4-(6-methoxy-1-methyl-1,2,3,4-tetrahydroisoquinolin-2-yl)pyrimidine After 1-methyl-6-methoxy-1,2,3,4-tetrahydroisoquinoline(1.3 g, 7.3 mmol) and triethylamine (1.0 ml, 7.3 mmol) were added to a suspension of 5,6-dimethyl-2,4-dichloropyrimidine(1.2 g, 6.64 mmol) in dimethylformamide, the reaction mixture was stirred for 3 hours at 85° C. The reaction mixture was cooled to a room temperature and diluted with ethyl acetate. The organic layer was washed with water and aqueous sodium hydroxide, dried over anhydrous magnesium sulfate, concentrated under a reduced pressure, and then purified by a silica gel column chromatography to give 1.7 g of the titled compound. (Yield: 78.5%)

Step 2: 5,6-dimethyl-2-(4-fluorophenylamino)-4-(6-methoxy-1-methyl-1, 2,3,4-tetrahydroisoquinolin-2-yl)pyrimidine hydrochloride After 4-fluoroaniline(0.72 ml, 7.5 mmol) and triethylamine(1.0 ml, 7.3 mmol) were added to a solution of 5,6-dimethyl-2-chloro4-(6-methoxy-1-methyl-1,2,3,4-tetrahydroisoquinolin-2-yl)pyrimidine(1.6 g, 5.0 mmol) in dimethylformamide(10 ml), 1.26 g of the titled compound was obtained in accordance with the same procedure as in Step 2 of Example 25.

Yield: 2260%; M.P.: 190–192° C.; $^1$H-NMR(DMSO-d6): δ 1.6(d, 3H), 2.2(s, 3H), 2.4(s, 3H), 2.6(s, 3H), 2.9(bd, 1H), 3.1(m, 1H), 3.6(m, 1H), 4.2(dd, 1H), 5.4(q, 1H), 7.2–7.3(m, 6H), 7.5–7.7(dd, 2H), 10.2(s, 1H), 12.9(s, 1H).

EXAMPLE 36

5,6-dimethyl-2-(4-fluorophenylamino)-4-(1-methyl-6-hydroxy-1,2,3,4-tetrahydroisoquinolin-2-yl) pyrimidine hydrochloride The same procedures as in Example 32 were repeated using 5,6dimethyl-2-(4-fluorophenylamino)-4-(6-methoxy- 1-methyl-1,2,3,4-tetrahydroisoquinolin-2-yl)pyrimidine hydrochloride(1.2 g, 2.8 mmol) and borone tribromide (1M-dichloromethane solution, 11.2 ml, 11.2 mmol) to afford 179 mg of the titled compound.

Yield: 15.4%; M.P.: 147–150° C.; $^1$H-NMR(CDCl3): δ 1.5(d, 3H), 2.2(s, 3H), 2.4(s, 3H), 2.8(m, 1H), 3.0(m,1H), 3.5(m, 1H), 4.2(m, 1H), 5.2(q, 1H), 6.8(m, 5H), 7.4(m, 2H), 10.0(s 1H), 13.8(s, 1H).

EXAMPLE 37

5,6-dimethyl-2-(4-fluorophenylamino)-4-(7-methoxy-1-methyl-1,2,3,4-tetrahydroisoq uinolin-2-yl)pyrimidine hydrochloride Step 1: 5,6-dimethyl-2-chloro-4-(7-methoxy-1-methyl-1,2,3,4-tetrahydroisoquinolin-2-yl)pyrimidine After 1-methyl-7-methoxy-1,2,3,4-tetrahydroisoquinoline (0.9 g, 5.1 mmol) and triethylamine (0.7 ml, 5.1 mmol) were added to a suspension of 5,6-dimethyl-2,4-dichloropyrimidine (0.8 g, 4.64 mmol) in dimethylformamide, 1.0 g of the titled compound was obtained in accordance with the same procedure as in Step 1 of Example 35. (Yield: 70.3%)

Step 2: 5,6-dimethyl-2-(4-fluorophenylamino)-4-(7-methoxy- 1-methyl-1,2, 3,4-tetrahydroisoquinolin-2-yl)pyrimidine hydrochloride After 4-fluoroaniline(0.32 ml, 3.3 mmol) and triethylamine(0.46 ml, 3.3 mmol) were added to a solution of 5,6-dimethyl-2-chloro-4-(7-methoxy-1-methyl-1,2,3,4-tetrahydroisoquinolin-2-yl)pyrimidine(0.7 g, 2.2 mmol) in dimethylformamide(5 ml), 0.55 g of the titled compound was obtained in accordance with the same procedure as in Step 2 of Example 25.

Yield: 58.6%; M.P.: 122–125° C.; $^1$H-NMR(CDCl3): δ 1.6(d, 3H), 2.2(s, 3H), 2.4(s, 3H), 2.8(m, 1H), 3.1(m,1H), 3.5(m, 1H), 3.8(s, 3H), 4.2(m, 1H), 5.4(q, 1H), 6.6(s, 1H), 6.8(d, 1H), 7.0(m, 3H), 7.5(m, 2H), 10.2(s, 1H), 14.0(s, 1H).

EXAMPLE 38

5,6-dimethyl-2-(4-fluorophenylamino)-4-(1-methyl-7-hydroxy-1,2,3,4-tetrahydroisoquinolin-2-yl) pyrimidine hydrochloride The same procedures as in Example 32 were repeated using 5,6-dimethyl-2-(4-fluorophenylamino)-4-(7-methoxy-1-methyl-1,2,3,4-tetrahydroisoquinolin-2-yl)pyrimidine hydrochloride(0.55 g, 1.3 mmol) and borone tribromide (1M-dichloromethane solution, 5.2 ml, 5.2 mmol) to afford 166 mg of the titled compound.

Yield: 30.8%; M.P.: 157–160° C.; $^1$H-NMR(DMSO-d6): δ 1.6(d, 3H), 2.2(s, 3H), 2.4(s, 3H), 2.8(m, 1H), 3.0(m,1H), 3.5(m, 1H), 4.2(m, 1H), 5.4(q, 1H), 6.6(s, 1H), 6.7(d, 1H), 7.0(d, 1H), 7.1(t, 2H) 7.5(m, 2H), 9.0(s, 1H), 10.2(s, 1H), 14.0(s, 1H).

EXAMPLE 39

5,6-dimethyl-2-(4-fluorophenylamino)-4-(5-methoxy-1-methyl-1,2,3,4-tetrahydroisoquinolin-2-yl)pyrimidine hydrochloride Step 1: 5,6-dimethyl-2-chloro4-(5-methoxy-1-methyl-1,2,3,4-tetrahydroisoquinolin-2-yl)pyrimidine After 1-methyl-5-methoxy-1,2,3,4-tetrahydroisoquinoline(0.9 g, 5.1 mmol) and triethylamine (0.7 ml, 5.1 mmol) were added to a suspension of 5,6-dimethyl-2,4-dichloropyrimidine(0.8 g, 4.64 mmol) in dimethylformamide, 1.0 g of the titled compound was obtained in accordance with the same procedure as in Step 1 of Example 35. (Yield: 70.3%)

Step 2: 5,6-dimethyl-2-(4-fluorophenylarnino)-4-(5-methoxy-1-methyl-1,2,3,4-tetrahydroisoquinolin-2-yl) pyrimidine hydrochloride After 4-fluoroaniline(0.32 ml, 3.3 mmol) and triethylamine(0.46 ml, 3.3 mmol) were added to a solution of 5,6-dimethyl-2-chloro-4-(5-methoxy-1-methyl-1,2,3,4-tetrahydroisoquinolin-2-yl)pyrimidine(0.7 g, 2.2 mmol) in dimethylformamide (5 ml), 0.55 g of the titled compound was obtained in accordance with the same procedure as in Step 2 of Example 25.

Yield: 58.6%; M.P.: 122–125° C.; $^1$H-NMR(CDCl3): δ 1.6(d, 3H), 2.2(s, 3H), 2.4(s, 3H), 2.8(m, 1H), 3.1(m,1H), 3.5(m, 1H), 3.8(s, 3H), 4.2(m, 1H), 5.4(q, 1H), 6.6(s, 1H), 6.8(d, 1H), 7.0(m, 3H), 7.5(m, 2H), 10.2(s, 11H), 14.0(s, 1H).

EXAMPLE 40

5,6-dimethyl-2-(4-fluorophenylamino)-4-(1-methyl-5-hydroxy-1,2,3,4-tetrahydroisoq uinolin-2-yl) pyrimidine hydrochloride The same procedures as in Example 32 were repeated using 5,6-dimethyl-2-(4-fluorophenylarnino)-4-(5-methoxy-1-methyl-1,2,3,4-tetrahydroisoquinolin-2-yl)pyriridine hydrochloride(0.55 g, 1.3 mmol) and borone tribromide (1M-dichloromethane solution, 5.2 ml, 5.2 mmol) to afford 166 mg of the titled compound.

Yield: 30.8%; M.P.: 157–160° C.; $^1$H-NMR(DMSO-d6): δ 1.6(d, 3H), 2.2(s, 3H), 2.4(s, 3H), 2.8(m, 1H), 3.0(m,1H), 3.5(m, 1H), 4.2(m, 1H), 5.4(q, 1H), 6.6(s, 1H), 6.7(d, 1H), 7.0(d, 1H), 7.1(t, 2H), 7.5(m, 2H), 9.0(s, 1H), 10.2(s, 1H), 14.0(s, 1H).

EXAMPLE 41

5,6-dimethyl-2-(4-fluorophenylamino)-4-(1-methyl-6,7-dihydroxy-1,2,3,4-tetrahydroisoquinolin-2-yl) pyrimidine hydrochloride Step 1: 5,6-dimethyl-2-chloro-4-(1-methyl-6,7-dihydroxy-1,2,3,4-tetrahydroisoquinolin-2-yl)pyrimidine After 1-methyl-6,7-dihydroxy-1,2,3,4-tetrahydroisoquinoline(1.6 g, 4.98 mmol) and triethylamine (0.7 ml, 4.98 mmol) were added to a suspension of 5,6-dimethyl-2,4-dichloropyrimidine(0.8 g, 4.53 mmol) in dimethylformamide, 1.1 g of the titled compound was obtained in accordance with the same procedure as in Step 1 of Example 35. (Yield: 76%)

Step 2: 5,6-dimethyl-2-(4-fluorophenylamino)-4-(1-methyl-6,7-dihydroxy-1,2,3,4-tetrahydroisoquinolin-2-yl) pyrimidine hydrochloride 4-fluoroaniline(0.46 ml, 4.70 mmol) and triethylamine (0.66 ml, 4.70 mmol) were added to a solution of 5,6-dimethyl-2-chloro-4-(1-methyl-6,7-dihydroxy-1,2,3,4-tetrahydroisoquinolin-2-yl)pyrimidine(1.0 g, 3.13 mmol) in dimethyifomiamide(5 ml) and then stirred for 3 hours at 120° C. The reaction mixture was cooled to a room temperature and diluted with dichloromethane. Aqueous sodium hydroxide solution was added to the reaction mixture, which was then stirred. The dichloromethane layer was dried over anhydrous magnesium sulfate, concentrated under a reduced pressure. The resulting residue was purified by a silica gel column chromatography and dissolved in ethanol. Ethyl ether saturated with hydrochloric acid was added to the solution. The resulting solid was filtered and dried to give 530 mg of the titled compound.

Yield: 39.3%; M.P.: 198–201° C.; $^1$H-NMR(DMSO-d6): δ 1.1(d, 2H), 1.3(d, 1H), 2.0(d, 3H), 2.4(s, 3H), 3.8(d, 1H), 4.0(m, 1H), 4.2(d, 2H), 5.2(q, 1H), 7.3(t, 3H), 7.6(q, 3H), 10.5(s, 1H).

EXAMPLE 42

5,6-dimethyl-2-(4-fluorophenylamino)-4-(5,8-dimethoxy-1-methyl-1,2,3,4-tetrahydroisoquinolin-2-yl)pyrimidine hydrochloride Step 1: 5,6-dimethyl-2-chloro-4-(5,8-dimethoxy-1-methyl-1,2,3,4-tetrahydroisoquinolin-2-yl)pyrimidine After 5,8-dimethoxy-1-methyl-1,2,3,4-tetrahydroisoquinoline(10 g, 4.82 mmol) and triethylamine (0.67 ml, 4.82 mmol) were added to a suspension of 5,6-dimethyl-2,4-dichloropyrimidine(0.71 g, 4.02 mmol) in dimethylformamide, 1.02 g of the titled compound was obtained in accordance with the same procedure as in Step 1 of Example 35. (Yield: 72.8%)

Step 2: 5,6-dimethyl-2-(4-fluorophenylamino)-4-(5,8-dimethoxy-1-methyl-1,2,3,4-tetrahydroisoquinolin-2-yl)pyrimidine hydrochloride After 4-fluoroaniline(0.40 ml, 4.13 mmol) and triethylamine(0.58 ml, 4.13 mmol) were added to a solution of 5,6-dimethyl-2-chloro-4-(5,8-dimethoxy-1-methyl-1,2,3,4tetrahydroisoquinolin-2-yl)pyrimidine (1.0 g, 2.87 mmol) in dimethylformamide(5 ml), 0.67 g of the titled compound was obtained in accordance with the same procedure as in Step 2 of Example 25. (Yield: 51.2%)

M.P.: 251–253° C.; NMR(CDCl$_3$): 1.5(d, 3H), 2.1(s, 3H), 2.3(s, 3H), 2.8(m, 2H), 3.5(m, 2H), 3.8(d, 6H), 4.0(m, 1H), 5.2(q, 1H), 6.6(s, 2H), 7.0(t, 2H), 7.5(q, 2H)

EXAMPLE 43

5,6-dimethyl-2-(4-fluorophenylamino)-4-(5,8-dihydroxy-1-methyl-1,2,3,4-tetrahydroisoquinolin-2-yl)pyrimidine hydrochloride The same procedures as in Example 32 were repeated using 5,6-dimethyl-2-(4-fluorophenylamino)-4-(5,8-dimethoxy-1-methyl-1,2,3,4-tetrahydroisoquinolin-2-yl) pyrimidine hydrochloride(0.6 g, 1.3 mmol) and borone tribromide(1M-dichloromethane solution, 5.2 ml, 5.2 mmol) to afford 124 mg of the titled compound.

Yield 48.1%; M.P.: 275–278° C.; $^1$H-NMR(DMSO-d6+ TFA): δ 1.6(d, 3H), 2.2(s, 3H), 2.4(s, 3H), 2.8(m, 2H), 3.6(m, 1H), 4.3(d, 1H), 5.6(s, 1H), 6.6(s, 2H), 7.2(t, 2H), 7.7(q, 2H).

EXAMPLE 44

6-methoxymethyl-5-methyl-2-(4-fluorophenylamino)-4-(1-methyl-6-methoxy-1,2,3,4-tetrahydroisoquinolin-2-yl)pyrimidine hydrochloride Step 1: 6-methoxymethyl-5-methyl-2-chloro-4-(1-methyl-6-methoxy-1,2,3,4-tetra-hydroisoquinolin-2-yl)pyrimidine After 1-methyl-6-methoxy-1,2,3,4-tetrahydroisoquinoline(1.2 g, 6.8 mmol) and triethylamine (0.96 ml, 6.9 mmol) were added to a suspension of 2,4-dichloro-6-methoxymethyl-5-methylpyrimidine(1.3 g, 6.3 mmol) in dimethylformamide, 2.0 g of the titled compound was obtained in accordance with the same procedure as in Step 1 of Example 35. (Yield: 73.6%)

Step 2: 6-methoxymethyl-5-methyl-2-(4-fluorophenylamino)-4-(1-methyl-6-methoxy-1,2, 3,4-tetrahydroisoquinolin-2-yl)pyrimidine hydrochloride After 4-fluoroaniline(0.32 ml, 3.3 mmol) and triethylamine(0.46 ml, 3.3 mmol) were added to a solution of 6-methoxymethyl-5-methyl-2-chloro-4-(1-methyl-6-methoxy-1,2,3,4-tetrahydroisoquinolin-2-yl)pyrimidine (1.0 g, 2.3 mmol) in dimethylformamide(5 ml), 0.56 g of the titled compound was obtained in accordance with the same procedure as in Step 2 of Example 25.

Yield 53.4%; $^1$H-NMR(CDCl3): 1.5(d, 3H), 2.2(s, 1H), 2.7(m, 1H), 3.1(m, 1H), 3.5(s, 3H), 3.8(s, 3H), 4.0(m, 1H), 4.4(s, 2H), 5.1(q, 1H), 6.6(m, 1H), 6.8(m, 1H), 6.9(m, 3H), 7.5(m, 2H).

EXAMPLE 45

6-hydroxymethyl-5-methyl-2-(4-fluorophenylamino)-4-(1-methyl-6-hydroxy-1,2,3,4-tetrahydroisoquinolin-2-yl)pyrimidine hydrochloride The same procedures as in Example 32 were repeated using 6-methoxymethyl-5-methyl-2-(4-fluorophenylamino)-4-(1-methyl 1–6-methoxy-1,2,3,4-tetrahydroisoquinolin-2-yl)pyrimidine hydrochloride(0.5 g, 1.1 mmol) and boron tribromide(1M-dichloromethane solution, 4.4 ml, 4.42 mmol) to afford 210 mg of the titled compound.

Yield 44.5%; M.P.: 181–184° C.; $^1$H-NMR(DMSO-d6): δ 1.5(d, 3H), 2.1(s, 3H), 2.6(d, 1H), 2.8–3.1(m, 1H), 3.0(m, 1H), 3.5(m, 1H), 3.9(m, 1H), 4.4(d, 2H), 4.9–5.1(m, 2H), 6.6(m, 2H), 6.8–7.1(m, 3H), 7.6–7.9(m, 2H), 9.2(s, 2H).

EXAMPLE 46

5-hydroxymethyl-6-methyl-4-(1-methyl-1,2,3,4-tetrahydroisoquinolin-2-yl)-2-(4-fluor ophenylamino)-pyrimidine Step 1:6-methyl-4-hydroxy-2-(4-fluorophenylamino) pyrimidine A mixture solution of ethyl acetoacetate(3.8 ml, 30.3 mmol), 4-fluorophenylguanidine carbonate(5 g, 26.3 mmol), and dimethylformamide(5 ml) was refluxed for 2 hours and cooled to a room temperature. Ethyl ether was added to the reaction mixture and the resulting solid was filtered, washed with ethyl ether, and concentrated under a reduced pressure to give 1.74 g of the titled compound. (Yield 30%)

Step 2:6-methyl-4-chloro-2-(4-fluorophenylamino) pyrimidine

A reaction mixture of 6-methyl-4-hydroxy-2-(4-fluorophenylamino)pyrimidine (1.74 g, 7.93 mmol) and phosphorus oxychloride was stirred for 1 hour at a room temperature and then dissolved in dichloromethane. Water was added dropwise to the reaction mixture and stirred for 30 minutes. The separated organic layer was washed with 2N NaOH solution, dried over anhydrous magnesium sulfate, and then concentrated under a reduced pressure to give 1.57 g of the titled compound. (Yield 83.5%)

NMR (CDCl3): 2.4(s, 3H), 6.6(s, 1H), 7.0(m, 3H), 7.6(m, 2H).

Step 3: 6-methyl-4-(1-methyl-1,2,3,4-tetrahydroisoquinolin)-2-(4-fluorophenylamino)pyrimidine A reaction mixture of 6-methyl-4-chloro-2-(4-fluorophenylamino)pyrimidine(1.4 g, 5.89 mmol), 1-methyl-1,2,3,4-tetrahydroisoquinolin(1.12 g, 7.66 mmol), triethylamine(1.06 ml, 7.66 mmol), and propylene glycol(19 ml) was stirred for 2 hours at 120° C., cooled to a room temperature, diluted with dichloromethane, and washed with water. The separated organic layer was dried over anhydrous sodium sulfate, concentrated under a reduced pressure and the residual oil was purified by a silica gel column chromatography (ethylacetate/n-hexane=1/1) to give 1.98 g of the titled compound. (Yield 96.4%)

NMR (CDCl3): 1.5(d, 3H), 2.3(s, 3H), 2.9(m, 2H), 3.5(m, 1H), 4.2(m, 1H), 5.4(br, 1H), 6.0(s, 1H), 6.8(s, 1H), 7.0(m, 2H), 7.2(m, 4H), 7.5(m, 2H).

Step 4: 5-hydroxymethyl-6-methyl-4-(1-methyl-1,2,3,4-tetrahydroisoquinolin-2-yl)-2-(4-fluorophenylamino) pyrimidine A mixture solution of 6-methyl-4-(1-methyl-1,2,3,4-tetrahydroisoquinolin)-2-(4-fluorophenylamino)pyrimidine (1.3 g, 3.73 mmol), formaline(37%, 30 ml) and p-formaldehyde (20 g) was stirred for 1 day at 80° C., extracted with dichloromethane, and then washed with aqueous 1N-NaOH solution and water. The separated organic layer was concentrated under a reduced pressure and the residual oil was purified by a silica gel column chromatography (ethylacetate/n-hexane =1/1) to give 0.17 g of the titled compound. (Yield 12%)

NMR (CDCl3): 1.6(d, 3H), 2.4(s, 3H), 2.8(m, 1H), 3.2(m, 1H), 3.6(m, 1H), 4.2(m, 1H), 4.6(q, 2H), 5.4(q, 1H), 6.9(m, 2H), 7.2(m, 4H), 7.5(m, 2H)

EXAMPLE 47

5,6-dimethyl-2-(4-fluorophenylamino)-4-(1-methoxymethyl-1,2,3,4-tetrahydroisoquinolin-2-yl)-pyrimidine Step 1: 5,6-dimethyl-2-chloro-4-(1-methoxymethyl-1,2,3,4-tetrahydroisoquinolin-2-yl)-pyrimidine After 1-methoxymethyl-1,2,3,4-tetrahydroisoquinolin (0.5 g, 2.82 mmol) and triethylamine(0.4 ml, 2.82 mmol) were added to a suspension of 5,6-dimethyl-2,4-dichloropyrimnidine(0.48 g, 2.68 mmol) in dimethylformamide (5 ml), 0.5 g of the titled compound was obtained in accordance with the same procedure as in Step 1 of Example 35.

Step 2: 5,6-dimethyl-2-(4-fluorophenylamino)-4-(1-methoxymethyl-1,2,3,4-tetra-hydroisoquinolin-2-yl)-pyrimidine After 4-fluoroaniline(0.15 ml, 1.57 mmol) and triethylamine(0.21 ml, 1.53 mmol) were added to a solution of 5,6-dimethyl-2-chloro-4-(1-methoxy-methyl-1,2,3,4-tetrahydroisoquinolin-2-yl)pyrimidine (0.5 g, 1.57 mmol) in dimethylfomiamide (5 ml), 0.4 g of the titled compound was obtained in accordance with the same procedure as in Step 2 of Example 25(Yield: 63.7%).

M.P.: 193–195° C.; NMR (DMSO-d6): 2.2(s, 3H), 2.3(s, 3H), 2.8–3.2(m, 2H), 3.4(s, 3H), 3.6–4.0(m, 3H), 4.3(bd, 1H), 5.5(bs, 1H), 7.0–7.5(m, 6H), 7.5–7.8(m, 2H), 9.6(s, 1H)

EXAMPLE 48

5,6-dimethyl-2-(4-fluorophenylamino)-4-(1-hydroxymethyl-1,2,3,4-tetrahydroisoquinolin-2-yl)-pyrimidine The same procedures as in Example 32 were repeated using 5,6-dimethyl-2-(4-fluorophenylamino)-4-(1-methoxymethyl-1,2,3,4-tetrahydroisoquinolin-2-yl)-pyrimidine(0.4 g, 1.0 mmol) and boron tribromide(1M-dichloromethane solution, 4.0 ml, 4.0 mmol) to afford 150 mg of the titled compound.

Yield: 36%; M.P.: 198–200° C.; $^1$H-NMR(DMSO-d6): δ 2.2(s, 3H), 2.4(s, 1H), 2.8–3.2(m, 2H), 3.6–4.0(m, 3H), 4.3(bd, 1H), 5.5(bs, 1H), 7.0–7.4(m, 6H), 7.4–7.7(m, 2H), 10.4(s, 1H).

EXAMPLE 49

5,6-dimethyl-4-(1-methyl-1,2,3,4-tetrahydroisoquinolin-2-yl)-2-(4-fluoro-2-hydroxyphenylamino)pyrimidine Step 1: 4-fluoro-2-methoxynitrobenzene Potassium carbonate(14.5 g, 105.1 mol) and iodomethane (7.1 ml, 114.6 mmol) were added to a solution of 2-nitro-5-fluorophenol(15 g, 95.5 mmol) in ethanol (100 ml), which was then refluxed for 12 hours. The resulting solid was filtered, washed with ethanol, and concentrated. The resulting oily residue was diluted with ethyl acetate and washed with water. The separated organic layer was concentrated and the residual oil was purified by column chromatography (ethylacetate/hexane=1/3) to give 1.65 g of the titled compound. (Yield 9.7%).

NMR (CDCl$_3$): 4.0 (s, 3H), 6.8 (m, 2H), 8.0 (m, 1H).

Step 2: 4-fluoro-2-methoxy-aniline

Paladium/carbon(Pd/C, 5%, 0.5 g) was added to a solution of 4-fluoro-2-methoxynitrobenzene (1.65 g, 9.6 mmol) in ethanol, which was then stirred for 1 hour under 30 psi of hydrogen pressure. The reaction mixture was filtered to remove paladium/carbon, and concentrated to give 1.35 g of the titled compound. (Yield 100%)

NMR (CDCl$_3$): 3.8 (s, 3H), 6.5 (m, 3H).

Step 3: 5,6-dimethyl-4-(1-methyl-1,2,3,4-tetrahydroisoquinolin-2-yl)-2-(4-fluoro-2-methoxyphenylamino)pyrimidine A reaction mixture of 4-fluoro-2-methoxy-aniline(0.155 g, 1.10 mmol), 5,6-dimethyl-2-chloro4-(1-methyl-1,2,3,4-tetrahydroisoquinolin-2-yl)pyrimidine(0.24 1g, 0.84 mmol), triethylamine(0.15 ml, 1.1 mmol) and propyleneglycol (2 ml) was heated to 140° C. for 5 hours, cooled to a room temperature, diluted with dichloromethane(10 ml), and then washed with water. The separated organic layer was concentrated and the residual oil was purified by column chromatography(ethylacetate/N-hexane=1/1) to give 0.247 g of the titled compound. (Yield 75.2%)

NMR (CDCl$_3$): 1.5 (d, 3H), 2.2 (s, 3H), 2.4 (s, 3H), 2.8 (m, 1H), 3.2 (m, 1H), 3.5 (m, 1H), 3.8 (s, 3H), 4.0 (m, 1H), 5.0 (q, 1H), 6.6 (m, 6H), 7.0(d, 1H).

Step 4: 5,6-dimethyl-4-(1-methyl-1,2,3,4-tetrahydroisoquinolin-2-yl)-2-(4-fluoro-2-hydroxyphenylamino) pyrimidine Boron tribromide (1M dichloromethane solution, 1.9 ml, 1.9 mmol) was added dropwise to a solution of 5,6-dimethyl-4-(1-methyl-1,2,3,4-tetrahydroisoquinolin-2-yl)-2-(4-fluoro-2-methoxyphenylamino)pyrimidine(0.247 g, 0.63 mmol) in dichloromethane(2 ml) at 0° C., stirred for 1 hour, and poured into ice water. The separated organic layer was concentrated and the residual oil was purified by column chromatography (dichloromethane/methanol=10/1) to give 57 mg of the titled compound. (Yield 24%) NMR (CDCl$_3$): 1.5 (d, 3H), 2.2 (s, 3H), 2.3 (s, 3H), 2.7 (m, 1H), 3.1 (m, 1H), 3.5 (m, 1H), 3.9 (m, 1H), 5.0 (q, 1H), 6.6 (m, 6H), 7.0 (d, 1H).

EXAMPLE 50

5-methyl-6-acetoxymethyl-2-(4-fluorophenylamino)-4-(1-methyl-1,2,3,4-tetrahydrois oquinolin-2-yl) pyrimidine Acetyl chloride (2.71 μl, 39.6 μmol) and triethylamine(20 μl, 142.6 μmol) were added to a suspension of 5-methyl-6-hydroxymethyl-2-(4-fluorophenylamino)-4-(1-methyl-1,2,3,4-tetrahydroisoquinolin-2-yl)pyrimidine (10 mg, 26.4 μmol) in dichloromethane(1 ml) and stirred for 1 day at a room temperature. The reaction mixture was purified with a silica gel column chromatography (ethylacetate/n-hexane= 1/1) to give 12 mg of the titled compound.

NMR(CDCl$_3$): 1.5(d, 3H), 2.2(s, 6H), 2.8(m, 1H), 3.2(m, 1H), 4.0(m, 1H), 5.0(s, 2H), 5.2(q, 1H), 6.9(m, 3H), 7.2(m, 4H), 7.5(m, 2H).

EXAMPLE 51–74

The same procedures as in Example 50 were repeated using 5-methyl-6-hydroxymethyl-2-(4-fluorophenylamino)-

4-(1-methyl-1,2,3,4-tetrahydroisoquinolin-2-yl)pyrimidine (10 mg, 26.4 μmol), correspondent acylchloride(39.6 μmol) and triethylamine(20 μl, 142.6 μmol) to give the following titled compound.

EXAMPLE 51

5-methyl-6-ethylcarbonyloxymethyl-2-(4-fluorophenylamino)-4-(1-methyl-1,2,3,4-tetrahydroisoquinolin-2-yl)pyrimidine NMR(CDCl$_3$): 1.2(t, 3H), 1.5(d, 3H), 2.2(s, 3H), 2.4(q, 2H), 2.8(m, 1H), 3.2(m, 1H), 3.6(m, 1H), 4.0(m, 1H), 5.0(s, 2H), 5.1(q, 1H), 6.8(s, 1H), 6.9(t, 2H), 7.2(m, 4H), 7.5(m, 2H).

EXAMPLE 52

5-methyl-6-isopropylcarbonyloxymethyl-2-(4-fluorophenylamino)-4-(1-methyl-1,2,3,4-tetrahydroisoquinolin-2-yl)pyrimidine NMR(CDCl$_3$): 1.1(d, 6H), 1.6(d, 3H), 2.2(s, 3H), 2.7(m, 2H), 3.2(m, 1H), 3.6(m, 1H), 4.0(m, 1H), 5.1(m, 2H), 7.0(m, 3H), 7.2(m, 4H), 7.5(m, 2H).

EXAMPLE 53

5-methyl-6-butylcarbonyloxymethyl-2-(4-fluorophenylamino)-4-(1-methyl-1,2,3,4-tetrahydroisoquinolin-2-yl)pyrimidine NMR(CDCl$_3$): 0.9(t, 3H), 1.4(m, 3H), 1.6(m, 4H), 2.2(s, 3H), 2.4(t, 2H), 2.8(m, 1H), 3.2(m, 2H), 3.6(m, 1H), 4.0(m, 1H), 5.1(m, 3H), 6.9(m, 3H), 7.2(m, 4H), 7.5(m, 2H).

EXAMPLE 54

5-methyl-6-cyclopropylcarbonyloxymethyl-2-(4-fluorophenylamino)-4-(1-methyl-1,2,3,4-tetrahydroisoquinolin-2-yl)pyrimidine NMR(CDCl$_3$): 0.9(m, 2H), 1.1(m, 2H), 1.5(d, 3H), 1.7(m, 1H), 2.2(s, 3H), 2.8(m, 1H), 3.2(m, 1H), 3.6(m, 1H), 4.0(m, 1H), 5.0(s, 3H), 5.1(q, 1H), 6.8(m, 1H), 6.9(t, 2H), 7.2(m, 4H), 7.5(m, 2H).

EXAMPLE 55

5-methyl-6-cyclobutylcarbonyloxymethyl-2-(4-fluorophenylamino)-4-(1-methyl-1,2,3,4-tetrahydroisoquinolin-2-yl)pyrimidine NMR(CDCl$_3$): 1.5(d, 3H), 2.1(m, 3H), 2.2(s, 3H), 2.3(m, 3H), 2.8(m, 1H), 3.2(m, 2H), 3.5(m, 1H), 3.9(m, 1H), 5.0(s, 2H), 5.1(q, 1H), 6.8(s, 1H), 6.9(m, 2H), 7.1(m, 4H), 7.5(m, 2H).

EXAMPLE 56

5-methyl-6-cyclohexylcarbonyloxymethyl-2-(4-fluorophenylamino)-4-(1-methyl-1,2,3,4-tetrahydroisoquinolin-2-yl)pyrimidine NMR(CDCl$_3$): 1.3(m, 2H), 1.4(m, 2H), 1.5(d, 3H), 1.6(m, 2H), 1.9(m, 2H), 2.2(s, 3H), 2.8(m, 1H), 3.2(m, 1H), 3.6(m, 1H), 4.0(m, 1H), 5.0(m, 2H), 5.1(q, 1H), 6.8(s, 1H), 6.9(m, 2H), 7.1(m, 4H), 7.5(m, 2H).

EXAMPLE 57

5-methyl-6-{(2-ethoxycarbonylethyl)carbonyloxymethyl}-2-(4-fluorophenylamino)-4-(1-methyl-1,2,3,4-tetrahydroisoquinolin-2-yl)pyrimidine NMR(CDCl$_3$): 1.2(t, 3H), 1.5(d, 3H), 2.2(s, 3H), 2.7(m, 5H), 3.2(m, 1H), 3.5(m, 1H), 4.0(m, 1H), 4.2(q, 2H), 5.1(m, 3H), 7.0(m, 3H), 7.2(m, 4H), 7.5(m, 2H)

EXAMPLE 58

5-methyl-6-benzoyloxymethyl-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.5(m, 1H), 4.0(m, 1H), 5.2(q, 1H), 5.3(s, 2H), 6.8(t, 2H), 7.1(m, 4H), 7.5(m, 6H), 2H).

EXAMPLE 59

5-methyl-6-(4-methylbenzoyloxymethyl)-2-(4-fluorophenylamino)-4-(1methyl-1,2,3,4-tetrahydroisoquinolin-2-yl)pyrimidine NMR(CDCl$_3$): 1.6(d, 3H), 2.2(s, 3H), 2.5(s, 3H), 2.8(m, 1H), 3.2(m, 1H), 3.6(m, 1H), 4.0(m, 1H), 5.2(q, 1H), 5.3(s, 2H), 6.8(t, 2H), 7.2(m, 5H), 2H), 8.0(m, 3H).

EXAMPLE 60

5-methyl-6-(4-propylbenzoyloxymethyl)-2-(4-fluorophenylamino)-4-(1-methyl-1,2,3,4-tetrahydroisoquinolin-2-yl)pyrimidine NMR(CDCl$_3$): 1.0(m, 3H), 1.6(d, 3H), 1.7(m, 2H), 2.2(s, 3H), 2.7(m, 2H), 2.8(m, 1H), 3.2(m, 1H), 3.5(m, 1H), 4.0(m, 1H), 5.2(q, 1H), 5.3(s, 2H), 6.8(t, 2H), 7.2(m, 6H), 7.5(m, 2H), 8.0(m, 3H).

EXAMPLE 61

5-methyl-6-(4-pentylbenzoyloxymethyl)-2-(4-fluorophenylamino)-4-(1-methyl-1,2,3,4-tetrahydroisoquinolin-2-yl)pyrimidine NMR(CDCl$_3$): 0.9(m, 5H), 1.3(m, 4H), 1.6(d, 3H), 2.2(s, 3H), 2.6(m, 3H), 3.2(m, 1H), 3.5(m, 1H), 4.0(m, 1H), 5.2(q, 1H), 5.3(s, 2H), 6.8(t, 2H), 7.2(m, 6H), 7.5(m, 2H), 8.0(m, 3H).

EXAMPLE 62

5-methyl-6-(3-fluorobenzoyloxymethyl)-2-(4-fluorophenylamino)-4-(1-methyl-1,2,3,4-tetrahydroisoquinolin-2-yl)pyrimidine NMR(CDCl$_3$): 1.6(d, 3H), 2.2(s, 3H), 2.8(m, 1H), 3.2(m, 1H), 3.6(m, 1H), 4.0(m, 1H), 5.2(q, 1H), 5.3(s, 2H), 6.8(t, 2H), 7.2(m, 6H), 7.5(m, 2H), 7.9(m, 2H).

EXAMPLE 63

5-methyl-6-(3-trifluoromethylbenzoyloxymethyl)-2-(4-fluorophenylamino)-4-(1-methyl-1,2,3,4-tetrahydroisoquinolin-2-yl)pyrimidine NMR(CDCl$_3$): 1.6(d, 3H), 2.2(s, 3H), 2.8(m, 1H), 3.2(m, 1H), 3.6(m, 1H), 4.0(m, 1H), 5.2(q, 1H), 5.4(s, 2H), 6.8(m, 3H), 7.2(m, 4H), 7.5(m, 2H), 7.6(t, 1H), 7.8(d, 1H), 8.4(m, 2H).

EXAMPLE 64

5-methyl-6-(2,3-difluorobenzoyloxymethyl)-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.6(m, 1H), 4.0(m, 1H), 5.1(q, 1H), 5.3(s, 2H), 6.8(s, 3H), 7.1(m, 5H), 7.4(m, 3H), 7.8(m. 1H).

EXAMPLE 65

5-methyl-6-(2-chlorobenzoyloxymethyl)-2-(4-fluorophenylamino)-4-(1-methyl-1,2,3,4-tetrahydroisoquinolin-2-yl)pyrimidine NMR(CDCl3): 1.5(d, 3H), 2.2(s, 3H), 2.8(m, 1H), 3.2(m, 1H), 3.6(m, 1H), 4.0(m, 1H), 5.1(q, 1H), 5.3(s, 2H), 6.8(m, 3H), 7.2(m, 5H), 7.6(m, 4H), 7.9(d, 1H)

EXAMPLE 66

5-methyl-6-(3-methoxyphenyl)acetoxymethyl-2-(4-fluorophenylamino)-4-(1-methyl-1, 2,3,4-tetrahydroisoquinolin-2-yl)pyrimidine NMR(CDCl$_3$): 1.5(d, 3H), 2.1(s, 3H), 2.8(m, 1H), 3.1(m, 1H), 3.6(m, 1H), 3.7(s, 2H), 3.8(s, 3H), 3.9(m, 1H), 5.1(m, 3H), 6.8(m, 7H), 7.2(m, 4H) 7.5(m, 2H).

EXAMPLE 67

5-methyl-6-(4-methoxyphenyl)acetoxymethyl-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.5(m, 1H), 3.6(s, 2H), 3.7(s, 3H), 3.9(m, 1H), 5.1(m, 3H), 5.3(s, 2H), 6.8(s, 1H), 6.9(m, 4H), 7.2(m, 6H), 7.5(m, 2H).

EXAMPLE 68

5-methyl-6-(4-nitrobenzoyloxymethyl)-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.6(m, 1H), 4.0(m, 1H), 5.1(q, 1H), 5.3(s, 2H), 6.9(m, 3H), 7.2(m, 4H), 7.5(m, 2H), 8.3(s 4H).

EXAMPLE 69

5-methyl-6-(3-cyanobenzoyloxymethyl)-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.6(m, 1H), 4.0(m, 1H), 5.1(q, 1H), 5.3(s, 2H), 6.8(m, 3H), 7.1(m, 4H), 7.4(m, 2H), 7.6(t, 2H), 7.9(d, 1H), 8.4(m, 2H).

EXAMPLE 70

5-methyl-6-(1-naphthoyloxymethyl)-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.6(m, 1H), 4.0(m, 1H), 5.1(q, 1H), 5.4(s, 2H), 6.8(m, 3H), 7.1(m, 4H), 7.5(m, 5H), 7.9(d, 1H), 8.0(d, 1H), 8.3(d, 1H), 9.0(d, 1H).

EXAMPLE 71

5-methyl-6-benzyloxyacetoxymethyl-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.5(m, 1H), 4.0(m, 1H), 4.2(s, 2H), 4.6(s, 2H), 5.1(m, 3H), 6.8(s, 1H), 7.0(t, 2H), 4H), 7.4(m, 7H).

EXAMPLE 72

5-methyl-6-cinnamoyloxymethyl-2-(4-fluorophenylamino)-4-(1-methyl-1,2,3,4-tetrahydroisoquinolin-2-yl)pyrimidine NMR(CDCl$_3$): 1.5(d, 3H), 2.2(s, 3H), 2.8(m, 1H), 3.2(m, 1H), 3.6(m, 1H), 4.0(m, 1H), 5.2(m, 3H), 6.6(d, 1H), 6.9(m, 3H), 7.1(m, 4H). 7.5(m, 7H), 7.8(d, 1H).

EXAMPLE 73

5-methyl-6-crotonyloxymethyl-2-(4-fluorophenylamino)-4-(1-methyl-1,2,3,4-tetrahydroisoquinolin-2-yl)pyrimidine NMR(CDCl$_3$): 1.5(d, 3H), 1.9(d, 3H), 2.2(s, 3H), 2.8(m, 1H), 3.2(m, 2H), 3.5(m, 1H), 4.0(m, 1H), 5.1(m, 3H), 6.0(m, 1H), 6.9(m, 3H), 7.1(m, 4H), 7.5(m, 2H).

EXAMPLE 74

5-methyl-6-(thiophen-2-yl-acetoxymethyl)-2-(4-fluorophenylamino)-4-(1-methyl-1,2,3,4-tetrahydroisoquinolin-2-yl)pyrimidine NMR(CDCl$_3$): 1.5(d, 3H), 2.1(s, 3H), 2.8(m, 1H), 3.1(m, 1H), 3.5(m, 1H), 3.9(m, 3H), 5.1(m, 3H), 6.7(s, 1H), 7.0(m, 4H), 7.2(m, 5H), 7.5(m, 2H).

EXAMPLE 75–113

The same procedures as in Example 50 were repeated using 5,6-dimethyl-2-(4-fluorophenylamino)-4-(1-methyl-6-hydroxy-1,2,3,4-tetrahydroisoq uinolin-2-yl)pyrimidine (10 mg, 26.4 µmol), correspondent acylchloride(39.6 µmol) and triethylamine(20 µl, 142.6 µmol) to give the following titled compound.

EXAMPLE 75

5,6-dimethyl-2-(4-fluorophenylamino)-4-(1-methyl-6-acetoxy-1,2,3,4-tetrahydroisoquinolin-2-yl)pyrimidine NMR(CDCl$_3$): 1.5(d, 3H), 2.1(s, 3H), 2.3(s, 3H), 2.4(s, 3H), 2.7(m, 1H), 3.1(m, 1H), 3.5(m, 1H), 3.9(m, 1H), 5.1(q, 1H), 7.0(m, 6H), 7.5(m, 2H).

EXAMPLE 76

5,6-dimethyl-2-(4-fluorophenylamino)-4-(1-methyl-6-ethylcarbonyloxy-1,2,3,4-tetrahydroisoquinolin-2-yl)pyrimidine NMR(CDCl$_3$): 1.2(t, 3H), 1.5(d, 3H), 2.1(s, 3H), 2.3(s, 3H), 2.6(q, 2H), 2.7(m, 1H), 3.1(m, 1H), 3.5(m, 1H), 3.9(m, 1H), 5.1(q, 1H), 6.9(m, 6H), 7.5(m, 2H).

EXAMPLE 77

5,6-dimethyl-2-(4-fluorophenylamino)-4-(1-methyl-6-isopropylcarbonyloxy-1,2,3,4-tetrahydroisoquinolin-2-yl)pyrimidine.

NMR(CDCl$_3$): 1.3(d, 6H), 1.5(d, 3H), 2.1(s, 3H), 2.3(s, 3H), 2.8(m, 2H), 3.1(m, 1H), 3.5(m, 1H), 3.9(m, 1H), 5.1(q, 1H), 7.0(m, 6H), 7.5(m, 2H).

EXAMPLE 78

5,6-dimethyl-2-(4-fluorophenylamnino)-4-(1-methyl-6-butylcarbonyloxy-1,2,3,4-tetrahydroisoquinolin-2-yl)pyrimidine NMR(CDCl$_3$): 0.9(m, 3H), 1.5(m, 5H), 1.7(m, 2H), 2.1(s, 3H), 2.3(s, 3H), 2.5(t, 2H), 2.7(m, 1H), 3.1(m, 1H), 3.5(m, 1H), 3.9(m, 1H), 5.1(q, 1H), 7.0(m, 6H), 7.5(m, 2H).

EXAMPLE 79

5,6-dimethyl-2-(4-fluorophenylamino)-4-(1-methyl-6-cyclopropylcarbonyloxy-1,2,3,4-tetrahydroisoquinolin-2-yl)pyrimidine NMR(CDCl$_3$): 1.0(m, 2H), 1.1(m, 2H), 1.5(d, 3H), 1.8(m, 1H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 2H).

EXAMPLE 80

5,6-dimethyl-2-(4-fluorophenylamino)-4-(1-methyl-6-cyclobutylcarbonyloxy-1,2,3,4-tetrahydroisoquinolin-2-yl)pyrimidine NMR(CDCl$_3$): 1.5(d, 3H), 20(m, 4H), 2.1(s, 3H), 2.3(s, 5H), 2.7(m, 1H), 3.1(m, 1H), 3.5(m, 2H), 3.9(m, 1H), 5.1(q, 1H), 6.9(m, 6H), 7.5(m, 2H).

EXAMPLE 81

5,6-dimethyl-2-(4-fluorophenylamino)-4-(1-methyl-6-cyclohexylcarbonyloxy-1,2,3,4-tetrahydroisoquinolin-2-yl)pyrimidine NMR(CDCl$_3$): 1.2(m, 9H), 1.5(d, 3H), 1.6(m, 1H), 2.1(s, 3H), 2.3(s, 3H), 2.5(m, 1H), 2.7(m, 1H), 3.1(m, 1H), 3.5(m, 1H), 3.9(m, 1H), 5.1(q, 1H), 6.9(m, 6H), 7.5(m, 2H).

EXAMPLE 82

5,6-dimethyl-2-(4-fluorophenylamino)-4-{1-methyl-6-(2-ethoxycarbonylethyl)carbonyloxy-1,2,3,4-tetrahydroisoquinolin-2-yl}pyrimidine NMR(CDCl$_3$): 1.3(t, 3H), 1.5(d, 3H), 2.1(s, 3H), 2.3(s, 3H), 2.7(m, 3H) 2H), 3.1(m, 1H), 3.5(m, 1H), 3.9(m, 1H), 4.1(q, 2H), 5.1(q, 1H), 7.0(m, 5H), 7.1(m, 1H), 7.5(m, 2H).

EXAMPLE 83

5,6-dimethyl-2-(4-fluorophenylamino)-4-(1-methyl-6-benzoyloxy-1,2,3,4-tetrahydroisoquinolin-2-yl)pyrimidine NMR(CDCl$_3$): 1.6(d, 3H), 2.1(s, 3H), 2.3(s, 3H), 2.8(m, 1H), 3.2(m, 1H), 3.6(m, 1H), 4.0(m, 1H), 5.2(q, 1H), 7.0(m, 4H), 7.2(m, 1H), 7.5(m, 5H), 8.0(s, 1H), 8.2(d, 2H).

EXAMPLE 84

5,6-dimethyl-2-(4-fluorophenylamino)-4-{1-methyl-6-(4-methylbenzoyioxy)-1,2,3,4-tetrahydroisoquinolin-2-yl}pyrimidine NMR(CDCl$_3$): 1.5(d, 3H), 2.1(s, 3H), 2.3(s, 3H), 2.4(s, 3H), 2.7(m, 1H), 3.1(m, 1H), 3.5(m, 1H), 3.9(m, 1H), 5.1(q, 1H), 7.0(m, 8H), 7.5(m, 2H), 8.1(d, 2H).

EXAMPLE 85

5,6-dimethyl-2-(4-fluorophenylamino)-4-{1-methyl-6-(4-ethylbenzoyloxy)-1,2,3,4-tetrahydroisoquinolin-2-yl}pyrimidine NMR(CDCl$_3$): 1.3(t, 3H), 1.5(d, 3H), 2.1(s, 3H), 2.3(s, 3H), 2.7(m, 3H), 3.1(m, 1H), 3.5(m, 1H), 3.9(m, 1H), 5.1(q, 1H), 7.0(m, 7H), 7.3(m, 1H), 7.5(m, 2H), 8.1(d, 2H).

EXAMPLE 86

5,6-dimethyl-2-(4-fluorophenylamino)-4-{1-methyl-6-(4-propylbenzoyloxy)-1,2,3,4-tetrahydroisoquinolin-2-yl}pyrimidine NMR(CDCl$_3$): 1.0(t, 3H), 1.5(d, 3H), 1.8(m, 2H), 2.1(s, 3H), 2.3(s, 3H), 2.7(m, 3H), 3.1(m, 1H), 3.5(m, 1H), 3.9(m, 1H), 5.1(q, 1H), 7.0(m, 6H), 7.3 (m, 1H), 7.5(m, 3H), 8.1(d, 2H).

EXAMPLE 87

5,6-dimethyl-2-(4-fluorophenylamino)-4-{1-methyl-6-(4-t-butylbenzoyloxy)-1,2,3,4-tetrahydroisoquinolin-2-yl}pyrimidine NMR(CDCl$_3$): 1.3(s, 9H), 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.5(m, 4H), 8.1(m, 2H).

EXAMPLE 88

5,6-dimethyl-2-(4-fluorophenylamino)-4-{1-methyl-6-(4-pentylbenzoyloxy)-1,2,3,4-tetrahydroisoquinolin-2-yl}pyrimidine NMR(CDCl$_3$): 0.9(m, 5H), 1.3(m, 4H), 1.5(d, 3H), 2.1(s, 3H), 2.3(s, 3H), 2.7(m, 3H), 3.1(m, 1H), 3.5(m, 1H), 3.9(m, 1H), 5.1(q, 1H), 7.0(m, 6H), 7.3(m, 2H), 7.5(m, 2H), 8.1(m, 2H).

EXAMPLE 89

5,6-dimethyl-2-(4-fluorophenylamino)-4-{1-methyl-6-(2-chlorobenzoyloxy)-1,2,3,4-ttrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.5(m, 5H), 8.1(d, 1H).

EXAMPLE 90

5,6-dimethyl-2-(4-fluorophenylamino)-4-{1-methyl-6-(4-chlorobenzoyloxy)-1,2,3,4-tetrahydroisoquinolin-2-yl}pyrinmidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 5H), 7.1(m, 1H), 7.5(m, 4H), 8.1(d, 2H).

EXAMPLE 91

5,6-dimethyl-2-(4-fluorophenylamino)-4-{1-methyl-6-(3-chlorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 3.1(m, 1H), 3.5(m, 1H), 3.9(m, 1H), 5.1(q, 1H), 7.0(m, 6H), 7.5(m, 4H), 8.1(m, 2H).

EXAMPLE 92

5,6-dimethyl-2-(4-fluorophenylamino)-4-{1-methyl-6-(2,4-dichloro-5-fluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.5(m, 2H), 7.6(d, 2H), 7.8(d, 2H).

EXAMPLE 93

5,6-dimethyl-2-(4-fluorophenylamino)-4-{1-methyl-6-(2,4,6-trichlorobenzoyloxy)- 1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 7H), 7.5(m, 3H).

EXAMPLE 94

5,6-dimethyl-2-(4-fluorophenylamino)-4-{1-methyl-6-(3-fluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 5H), 7.2(m, 1H), 7.3(m, 1H), 7.5(m, 3H), 8.0(m, 2H).

EXAMPLE 95

5,6-dimethyl-2-(4-fluorophenylamino)-4-{1-methyl-6-(2,3-difluorobenzoyloxy)-1,2,3,4-tetrahydroisoquinolin-2-yl}pyrimidine.

NMR (CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 7H), 7.6(m, 3H), 7.9(m, 1H).

EXAMPLE 96

5,6-dimethyl-2-(4-fluorophenylamino)-4-{1-methyl-6-(2,6-difluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 8H), 7.5(m, 3H).

EXAMPLE 97

5,6-dimethyl-2-(4-fluorophenylamino)-4-(1-methyl-6-(2,4-difluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 8H), 7.5(m, 2H), 8.1(m, 1H).

EXAMPLE 98

5,6-dimethyl-2-(4-fluorophenylamino)-{1-methyl-6 (2,3,4-trifluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 7H), 7.5(m, 2H), 7.9(m, 1H).

EXAMPLE 99

5,6-dimethyl-2-(4-fluorophenylamino)-4-{1-methyl-6-(2,3,6-trifluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 7H), 7.5(m, 3H).

EXAMPLE 100

5,6-dimethyl-2-(4-fluorophenylamino)-4-{1-methyl-6-(2,4,5-trifluorobenzoyloxy)-1,2,3,4-tetrahydroisoquinolin-2-yl)}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 7H), 7.5(m, 2H), 8.0(m, 1H).

EXAMPLE 101

5,6-dimethyl-2-(4-fluorophenylamino)-4-{1-methyl-6-(3-trifluoromethylbenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.5(m, 2H), 7.6(m, 1H), 7.9(m, 1H), 8.4(m, 2H).

EXAMPLE 102

5,6-dimethyl-2-(4-fluorophenylamino)-4-{1-methyl-(4-trifluoromethylbenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.3(m, 2H), 7.5(m, 2H), 8.2(m, 2H).

EXAMPLE 103

5,6-dimethyl-2-(4-fluorophenylamino)-4-{1-metiyl-6-(2,3,4,5-tetrafluorobenzoyloxy)-1,2, 3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 6H), 7.5(m, 2H), 7.7(m, 1H).

EXAMPLE 104

5,6-dimethyl-2-(4-fluorophenylamino)-4-{1-methyl-6-(3-methoxyphenyl)acetoxy-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 6H), 5.1(q, 1H), 7.0(m, 9H), 7.3(m, 1H), 7.5(m, 2H).

EXAMPLE 105

5,6-dimethyl-2-(4-fluorophenylamino)-4-{1-methyl-6-(4-methoxyphenyl)acetoxy-1,2,3,4-tetrahydroisoquinolin-2-yl}pyrimidine.

NMR(CDCl$_3$): 1.5(d, 3H), 2.1(s, 3H), 2.3(s, 3H), 2.7(m, 1H), 3.1(m, 1H), 3.5(m, 1H), 3.9(m, 6H), 5.1(q, 1H), 7.0(m, 9H), 7.3(m, 1H), 7.5(m, 2H).

EXAMPLE 106

5,6-dimethyl-2-(4-fluorophenylamino)-4-{1-methyl-6-(4-butoxybenzoyloxy)-1,2,3,4-tetrahydroisoquinolin-2-yl}pyrimidine NMR(CDCl$_3$): 1.0(m, 3H), 1.2(m, 2H), 1.5(d, 3H), 1.7(m, 2H), 2.1(s, 3H), 2.3(s, 3H), 2.7(m, 1H), 3.1(m, 1H), 3.5(m, 1H), 3.9(m, 1H), 4.1(t, 2H), 1H), 7.0(m, 8H), 7.5(m, 2H), 8.1(m, 2H).

EXAMPLE 107

5,6-diinethyl-2-(4-fluorophenylamino)-4-{1-methyl-6-(4-nitrobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 2H), 8.4(m, 4H).

EXAMPLE 108

5,6-dimethyl-2-(4-fluorophenylamino)-4-{1-methyl-6-(3-cyanobenzoyloxy)-1,2,3,4-tetrahydroisoquinolin-2-yl}pyrinidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 2H), 7.6(d, 1H), 7.9(d, 1H), 8.4(m, 2H).

EXAMPLE 109

5,6-dimethyl-2-(4-fluorophenylamino)-4-{1-methyl-6-(1-naphthoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 5H), 7.9(d, 1H), 8.1(d, 1H), 8.5(d, 1H), 9.0(d, 1H).

EXAMPLE 110

5,6dimethyl-2-(4-fluorophenylamino)-4-(1-methyl-6-cinnamoyloxy-1,2,3,4-tetrahydroisoquinolin-2-yl) pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.6(d, 1H), 6.9(m, 6H), 7.5(m, 6H), 7.8(d, 1H).

EXAMPLE 111

5,6-dimethyl-2-(4-fluorophenylamino)-4-(1-methyl-6-crotonyloxy-1,2,3,4-tetrahydroissoquinolin-2-yl)pyrimidine NMR(CDCl$_3$): 1.5(d, 3H), 2.0(d, 3H), 2.1(s, 3H), 2.3(s, 3H), 2.7(m, 1H), 3.1(m, 1H), 3.5(m, 1H), 3.9(m, 1H), 5.1(q, 1H), 6.0(d, 1H), 6.9(m, 5H), 7.2(m, 2H), 7.5(m, 2H).

EXAMPLE 112

5,6-dimethyl-2-(4-fluorophenylamino)-4-{1-methyl-6-(thiophen-2-yl-acetoxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 4.1(s, 2H), 5.1(q, 1H), 6.9(m, 9H), 7.5(m, 2H).

EXAMPLE 113

5,6-dimethy-2-(4-fluorophenylamino)-4-(1-methyl-6-benzyloxyacetoxy-1,2,3,4-tetrahydroisoquinolin-2-yl)pyrimidine NMR(CDCl$_3$): 1.5(d, 2H), 2.1(s, 3H), 2.3(s, 3H), 2.7(m, IH), 3.1(m, 1H), 3.5(m, 1H), 4.0(m, 1H), 4.3(s, 2H), 4.6(d, 1H), 4.7(s, 2H), 5.1(q, 1H), 6.9(m 4H), 7.1(m, 2H), 7.4(m, 7H).

EXAMPLE 114–138

The same procedures as in Example 50 were repeated using 5,6-dimethyl-2-(4-fluorophenylamino)-4-(1-methyl-7-hydroxy-1,2,3,4-tetrahydroisoquinolin-2-yl)pyrimidine (10 mg, 26.4 μmol), correspondent acylchloride(39.6 μmol) and triethylamine(20 μl, 142.6 μmol) to give the following titled compound.

EXAMPLE 114

5,6-dimethyl-2-(4-fluorophenylamino)-4-(1-methyl-7-acetoxy-1,2,3,4-tetrahydroisoquinolin-2-yl)pyrimidine NMR(CDCl$_3$): 1.5(d, 3H), 2.1(s, 3H), 2.3(s, 6H), 2.7(m, 1H), 3.1(m, 1H), 3.5(m, 1H), 3.9(m, 1H), 5.1(q, 1H), 6.9(m, 5H), 7.1(m, 1H), 7.5(m, 2H).

EXAMPLE 115

5,6-dimethyl-2-(4-fluorophenylatnino)-4-{1-methyl-7-ethylcarbonyloxy-1,2,3,4-tetrahydroisoquinolin-2-yl}pyrimidine NMR(CDCl$_3$): 1.2(t, 3H), 1.5(d, 3H), 2.1(s, 3H), 2.3(s, 3H), 2.6(m, 3H), 3.1(m, 1H), 3.5(m, 1H), 3.9(m, 1H), 5.1(q, 1H), 6.9(m, 6H), 7.5(m, 2H).

EXAMPLE 116

5,6-dimethyl-2-(4-fluorophenylamino)-4-(1-methyl-7-isopropylcarbonyloxy-1,2,3,4-tetrahydroisoquinolin-2-yl)pyrimidine NMR(CDCl$_3$): 1.3(m, 6H), 1.5(d, 3H), 2.1(s, 3H), 2.3(s, 3H), 2.7(m, 2H), 3.1(m, 1H), 3.5(m, 1H), 3.9(m, 1H), 5.1(q, 1H), 7.0(m, 6H), 7.5(m, 2H).

EXAMPLE 117

5,6-dimethyl-2-(4-fluorophenylamino)-4-(1-methyl-7-butylcarbonyloxy-1,2,3,4-tetrahydroisoquinolin-2-yl)pyrimidine NMR (CDCl$_3$): 1.0(m, 3H), 1.5(m, 5H), 1.7(m, 2H), 2.1(s, 3H), 2.3(s, 3H), 2.6(t, 2H), 2.7(m, 1H), 3.1(m, 1H), 3.5(m, 1H), 3.9(m, 1H), 5.1(q, 1H), 6.9(m 4H), 7.1(m, 1H), 7.5(m, 2H).

EXAMPLE 118

5,6-dimethy1-2-(4-fluorophenylamino)-4-(1-methyl-7-cyclopropylcarbonyloxy- 1,2,3,4-tetrahydroisoquinolin-2-yl)pyrimidine NMR(CDCl$_3$): 1.0(m, 2H), 1.2(m, 2H), 1.5(d, 3H), 1.8(m, 1H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 2H).

EXAMPLE 119

5,6dimethyl-2-(4-fluorophenylamino)-4-(1-methyl-7-cyclobutylcarbonyloxy-1,2,3,4-tetrahydroisoquinolin-2-yl)pyrimidine NMR(CDCl$_3$): 1.5(d, 3H), 2.0(m, 2H), 2.1(s, 3H), 2.3(m, 7H), 2.7(m, 1H), 3.1(m, 1H), 3.4(m, 2H), 3.9(m, 1H), 5.1(q, 1H), 6.9(m, 6H), 7.5(m, 2H).

EXAMPLE 120

5,6-dimethyl-2-(4-fluorophenylamino)-4-(1-methyl-7-cyclohexylcarbonyloxy-1,2,3,4-tetrahydroisoquinolin-2-yl)pyrimidine NMR(CDCl$_3$): 1.3(m, 6H), 1.5(d, 3H), 1.7(m, 4H), 2.1(s, 3H), 2.3(s, 3H), 2.6(m, 1H), 2.7(m, 1H), 3.1(m, 1H), 3.5(m, 1H), 3.9(m, 1H), 5.1(q, 1H), 7.0(m, 5H), 7.5(m, 2H), 7.8(s, 1H).

EXAMPLE 121

5,6-dimethyl-2-(4-fluorophenylamino)-4-{1-methyl-7-(2-ethoxycarbonyletbyl)carbonyloxy-1,2,3,4-tetrahydroisoquinolin-2-yl) pyrimidine NMR(CDCl$_3$): 1.2(t, 3H), 1.5(d, 3H), 2.1(s, 3H), 2.3(s, 3H), 2.7(m, 3H), 2.9(m, 2H), 3.1(m, 1H), 3.5(m, 1H), 3.9(m, 1H), 4.2(q, 2H), 5.1(q, 1H), 6.9(m, 6H), 7.5(m, 2H).

EXAMPLE 122

5,6-dimethyl-2-(4-fluorophenylamino)-4-(1-methyl-7-benzoyloxy-1,2,3,4-tetrahydroisoquinolin-2-yl)pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 5H), 7.2(d, 1H), 7.5(m, 5H), 8.2(d, 2H).

EXAMPLE 123

5,6-dimethyl-2-(4-fluorophenylamino)-4-{ 1-methyl-7-(4-methylbenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.5(s, 3H), 2.7(m, 1H), 3.1(m, 1H), 3.5(m, 1H), 3.9(m, 1H), 5.1(q, 1H), 6.9(m, 6H), 7.1(m, 1H), 7.3(m, 1H), 7.4(m, 2H), 8.1(m, 2H).

EXAMPLE 124

5,6-dimethyl-2-(4-fluorophenylamino)-4-{1-methyl-7-(4-propylbenzoyloxy)-1,2,3,4-tetrahydroisoquinolin-2-yl}pyrimidine NMR(CDCl$_3$): 1.0(t, 3H), 1.5(d, 3H), 1.7(m, 2H), 2.1(s, 3H), 2.3(s, 3H), 2.7(m, 3H), 3.1(m, 1H), 3.5(m, 1H), 3.9(m, 1H), 5.1(q, 1H), 6.9(m, 5H), 7.1(m, 1H), 7.3(m, 2H), 7.5(m, 2H), 8.1(m, 2H).

EXAMPLE 125

5,6-dimethyl-2-(4-fluorophenylamino)-4-{1-methyl-7-(4-pentylbenzoyloxy)-1,2,3,4-tetrahydroisoquinolin-2-yl}pyrimidine NMR(CDCl$_3$): 0.9(t, 3H), 1.3(m, 6H), 1.5(d, 3H), 2.1(s, 3H), 2.3(s, 3H), 2.7(m, 3H), 3.1(m, 1H), 3.5(m, 1H), 3.9(m, 1H), 5.1(q, 1H), 6.9(m, 6H), 7.2(m, 1H), 7.3(m, 1H), 7.5(m, 2H), 8.1(m, 2H).

EXAMPLE 126

5,6dimethyl-2-(4-fluorophenylamino)-4-{1-methyl-7-(2-chlorobenzoyioxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 5H), 8.0(d, 1H).

EXAMPLE 127

5,6-dimethyl-2-(4-fluorophenylamino)-4-{1-methyl-7-(3-fluorobenzoyloxy)-1,2,3,4-tetrahydroisoquinolin-2-yl)pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 4H), 7.9(d, 1H), 8.0(d, 1H).

EXAMPLE 128

5,6dimethyl-2-(4-fluorophenylamino)-4-{ 1-methyl-7-(3-trifluoromethylbenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 7.0(m, 5H), 7.2(t, 1H), 7.5(m, 2H), 7.7(t, 1H), 7.9(d, 1H), 8.4(d, 1H), 8.5(s, 1H).

EXAMPLE 129

5,6dimethyl-2-(4-fluorophenylamino)-4-{1-methyl-7-(2,3-difluorobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 4H), 7.9(t, 1H).

EXAMPLE 130

5,6dimethyl-2-(4-fluorophenylamino)-4-(1-methyl-7-(3-methoxyphenyl)acetoxy-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.8(m, 6H), 5.1(q, 1H), 6.9(m, 10H), 7.5(m, 2H).

EXAMPLE 131

5,6dimethyl-2-(4-fluorophenylamino)-4-{1-methyl-7-(4-methoxyphenyl)acetoxy-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.8(m, 6H), 5.1(q, 1H), 6.9(m, 10H), 7.5(m, 2H).

EXAMPLE 132

5,6dimethyl-2-(4-fluorophenylamino)-4-{1-methyl-7-(4-nitrobenzoyloxy)-1,2,3,4-tetrahydroisoquinolin-2-yl}pyrimidine NMR(CDCl3): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 6H), 7.5(m, 2H), 8.4(s, 4H).

EXAMPLE 133

5,6dimethyl-2-(4-fluorophenylamino)-4-{1-methyl-7-(3-cyanobenzoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.9(m, 5H), 7.2(d, 2H), 7.4(m, 2H), 7.7(t, 1H), 7.9(d, 1H), 8.4(m, 2H).

EXAMPLE 134

5,6dimethyl-2-(4-fluorophenylamino)-4-{1-methyl-7-(1-naphthoyloxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q 1H), 6.9(m, 6H), 7.5(m, 5H), 7.9(d, 1H), 8.1(d, 1H), 8.5(d, 1H), 9.0(d, 1H).

EXAMPLE 135

5,6dimethyl-2-(4-fluorophenylamino)-4-{1-methyl-7-cinnamoyloxy-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 5.1(q, 1H), 6.6(d, 1H), 6:9(m, 5H), 7.1(d, 1H), 7.4(m, 4H), 7.6(m, 211), 7.9(d, 1H).

EXAMPLE 136

5,6-dimethyl-2-(4-fluorophenylamino)-4-{1-methyl-7-crotonyloxy-1,2,3,4-tetrahydroissoquinolin-2-yl}pyrimidine NMR(CDCl$_3$): 1.5(d, 3H), 2.0(d, 3H), 2.1(s, 3H), 2.3(s, 3H), 2.7(m, 1H), 3.1(m, 1H), 3.5(m, 1H), 3.9(m, 1H), 5.1(q, 1H), 6.0(d, 1H), 6.9(m, 4H), 2H), 7.5(m, 2H).

EXAMPLE 137

5,6-dimethyl-2-(4-fluorophenylamino)-4-{1-methyl-7-(thiophen-2-yl-acetoxy)-1,2,3,4-tetrahydroisoquinolin-2-yl}pyrimidine NMR(CDCl$_3$): 1.5(d, 3H), 2.1(s, 3H), 2.3(s, 3H), 2.7(m, 1H), 3.1(m, 1H), 3.5(m, 1H), 3.9(m, 1H), 4.1(s, 2H), 5.1(q, 1H), 6.9(m, 9H), 7.5(m, 2H).

EXAMPLE 138

5,6-dimethyl-2-(4-fluorophenylamino)-4-{1-methyl-7-benzyloxyacetoxy-1,2,3,4-tetrahydroisoquinolin-2-yl}pyrimidine NMR(CDCl$_3$): 1.5(d, 2H), 2.1(s, 3H), 2.3(s, 3H), 2.7(m, 1H), 3.1(m, 1H), 3.5(m, 1H), 3.9(m, 1H), 4.4(s, 2H), 4.6(d, 1H), 4.7(s, 2H), 5.1(q, 1H), 6.9(m, 2H), 7.1(m, 3H), 7.4(m, 8H).

EXAMPLE 139

5-methyl-6-(N-t-butoxycarbonyl-glycyloxymetyl)-2-(4-fluorophenylamino)-4-(1-methyl-1,2,3,4-tetrahydroisoquinolin-2-yl)pyrimidine 1-hydroxybenzotriazole(26.8 mg, 0.198 mmol), 1-ethyl-3-(3-dimethylaminopropyl)carbodiimide(32.9 mg, 0.171 mmol), N-t-butoxycarbonylglycine(27.8 mg, 0.158 mmol) and triethylamine(23.9 μl 0.171 mmol) were added to a suspension of 5-methyl-6-hydroxymethyl-2-(4-fluorophenylamino)-4-(1-methyl-1,2,3,4-tetrahydroisoquinolin-2-yl)pyrimidine(50 mg, 0.132 mmol) in anhydrous methylene chloride(1 ml). The reaction mixture was stirred for 1 day at room temperature, washed with water. The separated organic layer was concentrated and the residual oil was purified by a silica gel column chromatography (dichloromethane/methanol 20/1) to give the titled compound.

NMR(CDCl$_3$): 1.4(s, 9H), 1.5(d, 3H), 2.2(s, 3H), 2.8(m, 1H), 3.1(m, 1H), 3.5(m, 1H), 4.0(m, 3H), 5.1(s, 2H), 5.2(q, 1H), 6.9(m, 2H), 7.1(m, 5H), (m, 2H).

EXAMPLE 140–146

The same procedures as in Example 139 were repeated using 5-methyl-6-hydroxymethyl-2-(4-fluorophenylamino)-4-(1-methyl-1,2,3,4-tetrahydroisoquinolin-2-yl)pyrimidine (50 mg, 0.132 mmol), 1-hydroxybenzotriazole (26.8 mg, 0.198 mmol), 1-ethyl-3-(3-dimethylaminopropyl) carbodiimide(32.9 mg, 0.171 mmol), correspondent N-t-butoxycarbonylamino acid (0.158 mmol) and triethylamine (23.9 μl, 0.171 mmol) to obtain the following titled compound.

EXAMPLE 140

5-methyl-6-(N-t-butoxycarbonyl-valyloxymethyl)-2-(4-fluorophenylamino)-4-(1-methyl-1,2,3,4-tetrahydroisoquinolin-2-yl)pyrimidine NMR(CDCl$_3$): 0.9(d, 3H), 1.0(d, 3H), 1.4(s, 9H), 1.5(d, 3H), 2.2(s, 3H), 2.3(m, 1H), 2.8(m, 1H), 3.1(m, 1H), 3.5(m, 1H), 4.0(m, 1H), 4.2(m, 1H), 5.1(m, 3H), 6.9(m, 2H), 7.1(m, 5H), 7.4(m, 2H).

EXAMPLE 141

5-methyl-6-(N-t-butoxycarbonyl-O-benzylseryloxymethyl)-2-(4-fluorophenylamino)-4-(1-methyl-1,2,3,4-tetrahydroisoquinolin-2-yl)pyrimidine NMR(CDCl$_3$): 1.4(s, 9H), 1.5(d, 3H), 2.2(s, 3H), 2.8(m, 1H), 3.1(m, 1H), 3.5(m, 1H), 4.0(m, 2H), 4.5(s, 2H), 4.6(m, 1H), 5.1(s, 3H), 5.5(d, 1H), 2H), 7.1(m, 5H), 7.2(m, 5H), 7.4(m, 2H).

EXAMPLE 142

5-methyl-6-(N-t-butoxycarbonyl-methionyloxymethyl)-2-(4-fluorophenylamino)-4-(1-methyl-1,2,3,4-tetrahydroisoquinolin-2-yl)pyrimidine NMR(CDCl$_3$): 1.4(s, 9H), 1.5(d, 3H), 2.1(s, 3H), 2.2(s, 3H), 2.8(m, 3H), 3.1(m, 1H), 3.5(m, 1H), 4.0(m, 1H), 4.6(m, 1H), 5.1(m, 3H), 6.9(m, 2H), 7.1(m, 5H), 7.4(m, 2H).

EXAMPLE 143

5-methyl-6-(N-t-butoxycarbonyl-O-benzyl-aspartyloxymethyl)-2-(4-fluorophenylamino)-4-(1-methyl-1,2,3,4-tetrahydroisoquinolin-2-yl)pyrimidine NMR(CDCl$_3$): 1.4(s, 9H), 1.5(d, 3H), 2.2(s, 3H), 2.8(m, 1H), 3.1(m, 3H), 3.5(m, 1H), 4.0(m, 1H), 4.8(m, 1H), 5.1(s, 5H), 5.6(d, 1H), 6.9(m, 2H), 7.1(m, 5H), 7.3(m, 5H), 7.4(m, 2H).

EXAMPLE 144

5-methyl-6-(N-t-butoxycarbonyl-Im-benzyl-histidyloxymethyl)-2-(4-fluorophenylamino)-4-(1-methyl-1,2,3,4-tetrahydroisoquinolin-2-yl)pyrimidine NMR(CDCl$_3$): 1.4(s, 9H), 1.5(d, 3H), 2.2(s, 3H), 2.8(m, 1H), 3.1(m, 3H), 3.5(m, 1H), 4.0(m, 1H), 4.7(m, 1H), 4.9(s, 2H), 5.1(m, 3H), 6.0(d, 1H), 6.6(s, 1H), 6.9(m, 2H), 7.1(m, 5H), 7.3(m, 5H), 7.4(s, 1H), 7.5(m, 2H).

EXAMPLE 145

5-methyl-6-(N-t-butoxycarbonyl-phenylalanyloxymethyl)-2-(4-fluorophenyl amino)-4-(1-methyl-1,2,3,4-tetrahydroisoquinolin-2-yl)pyrimidine NMR(CDCl$_3$): 1.4(s, 9H), 1.5(d, 3H), 2.1(s, 3H), 2.8(m, 1H), 3.1(m, 3H), 3.5(m, 1H), 4.0(m, 1H), 4.7(m, 1H), 5.1(m, 3H), 6.9(m, 2H), 7.2(m, 10H), 7.5(m, 2H).

EXAMPLE 146

5-methyl-6-(N-t-butoxycarbonyl-prolyloxymethyl)-2-(4-fluorophenylatnino)-4-(1-methyl-1,2,3,4-tetrahydroisoquinolin-2-yl)pyrimidine NMR(CDCl$_3$): 1.4(m, 11H), 1.5(d, 3H), 2.0(m, 2H), 2.2 (d, 3H), 2.8(m, 1H), 3.1(m, 1H), 3.5(m, 3H), 4.0(m, 1H), 4.4(m, 1H), 5.1(m, 3H), 6.8(s, 1H), 6.9(m, 2H), 7.1(m, 5H), 7.5(m, 2H).

EXAMPLE 147–156

The same procedures as in Example 139 were repeated using 5,6-dimethyl-2-(4-fluorophenylamino)-4-(1-methyl1–6-hydroxy-1,2,3,4-tetrahydroisoquinolin-2-yl}pyrimidine(50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), correspondent N-t-butoxycarbonylamino acid(0.158 mmol) and triethylamine (23.9 μl, 0.171 mmol) to obtain the following titled compound.

EXAMPLE 147

5,6dimethyl-2-(4-fluorophenylamino)-4-{1-methyl-6-(N-t-butoxycarbonylglycyloxy)-1,2,3,4-tetrahydroisoquinolin-2-yl}pyrimidine NMR(CDCl$_3$): 1.5 (m, 12H), 2.1 (s, 3H), 2.3 (s, 3H), 2.7 (m, 1H), 3.1 (m, 1H), 3.5 (m, 1H), 3.9 (m, 1H), 4.1 (d, 2H), 5.1 (m, 2H), 6.9 (m, 4H), 7.1 (d, 1H), 7.4 (m, 2H).

EXAMPLE 148

5,6dimethyl-2-(4-fluorophenylamino)-4-{1-methyl-6-(N-t-butoxycarbonyl-valyloxy)-1,2, 3,4-tetrahydroisoquinolin-2-yl}pyrimidine NMR(CDCl$_3$): 1.0 (m, 6H), 1.5 (m, 12H), 2.1 (s, 3H), 2.3 (s, 3H), 2.7 (m, 1H), 3.1 (m, 1H), 3.5 (m, 1H), 3.9 (m, 1H), 4.4 (m, 1H), 5.1 (m, 2H), 6.9 (m, 4H), 7.1 (d, 11H), 7.5 (m, 2H).

EXAMPLE 149

5,6dimethyl-2-(4-fluorophenylamino)-4-{1-methyl-6-(N-t-butoxycarbonyl-O-benzyl-seryloxy)-1,2,3,4-tetrahydroisoquinolin-2-yl}pyrimidine NMR(CDCl$_3$): 1.5 (m, 12H), 2.1 (s, 3H), 2.3 (s, 3H), 2.7 (m, 1H), 3.1 (m, 1H), 3.5 (m, 1H), 3.8 (m, 1H), 4.0 (m, 2H), 4.6 (m, 2H), 5.1 (q, 1H), 5.5 (d, 1H), 6.9 (m, 4H), 7.1 (d, 1H), 7.3 (m, 5H), 7.4 (m, 2H).

EXAMPLE 150

5,6dimethyl-2-(4-fluorophenylamino)-4-{1-methyl-6-(N-t-butoxycarbonyl-methionyloxy)-1,2,3,4-tetrahydroisoquinolin-2-yl}pyrimidine NMR(CDCl$_3$): 1.5 (m, 12H), 2.1 (m, 6H), 2.3 (s, 3H), 2.6 (m, 3H), 3.1 (m, 1H), 3.5 (m, 1H), 3.9 (m, 1H), 4.6 (m, 1H), 5.1 (m, 2H), 6.9 (m, 4H), 7.1 (d, 1H), 7.4 (m, 2H).

EXAMPLE 151

5,6dimethyl-2-(4-fluorophenylamino)-4-{1 1-methyl-6-(N-t-butoxycarbonyl-O-benzyl-aspartyloxy)-1,2,3,4-tetrahydroisoquinolin-2-yl}pyrimidine NMR(CDCl$_3$): 1.5 (m, 12H), 2.1 (s, 3H), 2.3 (s, 3H), 2.7 (m, 1H), 3.1 (m, 3H), 3.5 (m, 1H), 3.9 (m, 1H), 4.8 (m, 1H), 5.1 (m, 3H), 5.6 (d, 1H), 6.9 (m, 4H), 7.1 (d, 1H), 7.3 (m, 5H), 7.5 (m, 2H).

EXAMPLE 152

5,6dimethyl-2-(4-fluorophenylamino)-4-{ 1-methyl-6-(N-t-butoxycarbonyt-asparaginyloxy)-1,2,3,4-tetrahydroisoquinolin-2-yl}pyrimidine NMR(CDCl$_3$): 1.5 (m, 12H), 2.1 (s, 3H), 2.3 (s, 3H), 2.7 (m, 1H), 3.0 (m, 3H), 3.5 (m, 1H), 4.1 (m, 1H), 4.3 (m, 1H), 5.1 (q, 1H), 6.0 (d, 1H), 6.6 (s, 1H), 6.7 (m, 1H), 6.9 (m, 3H), 7.4 (m, 2H).

EXAMPLE 153

5,6dimethyl-2-(4-fluorophenylamino)-4-{1-methyl-6-(N-t-butoxycarbonyl-glutaminyloxy)-1,2,3,4-tetrahydroisoquinolin-2-yl}pyrimidine NMR(CDCl$_3$): 1.5 (m, 12H), 2.1 (m, 5H), 2.3 (s, 3H), 2.6 (m, 3H), 3.0 (m, 1H), 3.5 (m, 11H), 3.9 (m, 1H), 4.3 (m, 1H), 5.0 (q, 1H), 6.6 (m, 2H), 6.9 (m, 3H), 7.4 (m, 2H).

EXAMPLE 154

5,6dimethyl-2-(4-fluorophenylamino)-4-{1-(-methyl-6-(N-t-butoxyc arbonyi-Im-benzyl-histidyloxy)-1,2,3,4-tetrahydroisoquinolin-2-yl}pyrimidine NMR(CDCl$_3$): 1.5(m, 12H), 2.1(s, 3H), 2.3(s, 3H), 2.7(m, 1H), 3.1(m, 3H), 3.5(m, 1H), 3.9(m, 1H), 4.8(m, 1H), 5.0(m, 3H), 6.2(m, 1H), 6.8(m, 2H), 6.9(m, 4H), 7.1 (m, 1H), 7.3(m, 3H), 7.4(m, 3H).

EXAMPLE 155

5,6dimethyl-2-(4-fluorophenylamino)-4-{1-methyl-6-(N-t-butoxycarbonyl-phenylalanyloxy)-1,2,3,4-tetrahydroisoquinolin-2-yl}pyrimidine NMR(CDCl$_3$): 1.4(s, 9H), 1.5(m, 3H), 2.1(s, 3H), 2.3(s, 3H), 2.7(m, 1H), 3.1(m, 3H), 3.5(m, 1H), 3.$^9$(m, 1H), 4.8(m, 1H), 5.1(m, 2H), 6.8(m, 2H), 7.0(m, 2H), 7.2(m, 6H), 7.5(m, 2H).

EXAMPLE 156

5,6dimethyl-2-(4-fluorophenylarnino)-4-{1-methyl-6-(N-t-butoxycarbonyl-prolyloxy)-1,2,3,4-tetrahydroisoquinolin-2-yl}pyrimidine NMR(CDCl$_3$): 1.5(m, 12H), 2.0(m, 4H), 2.1(s, 3H), 2.3(s, 3H), 2.7(m, 1H), 3.1(m, 1H), 3.5(m, 3H), 3.9(m, 1H), 4.5(m, 1H), 5.1(q, 1H), 6.9(m, 4H), 7.1(m, 1H), 7.5(m, 2H).

EXAMPLE 157–166

The same procedures as in Example 139 were repeated using 5,6-dimethyl-2-(4-fluorophenylamino)-4-(1-methyl-7-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl) carbodiimide (32.9 mg, 0.171 mmol), correspondent N-t-butoxycarbonylamino acid(0.158 mmol), and triethylamine (23.9 μl, 0.171 mmol) to obtain the following titled compound.

EXAMPLE 157

5,6dimethyl-2-(4-fluorophenylamino)-4-{1-methyl-7-(N-t-butoxycarbonylglycyloxy)-1,2,3,4-tetrahydroisoquinolin-2-yl}pyrimidine NMR(CDCl$_3$): 1.5(m, 12H), 2.1(s, 3H), 2.3(s, 3H), 2.7(m, 1H), 3.1(m, 1H), 3.5(m, 1H), 3.9(m, 1H), 4.2(d, 2H), 5.1(q, 1H), 5.2(t, 1H), 6.9(m, 4H), 7.1(d 1H), 7.4(m, 2H).

EXAMPLE 158

5,6dimethyl-2-(4-fluorophenylamino)-4-{1-methyl-7-(N-t-butoxycarbonyl-valyloxy)-1,2,3,4-tetrahydroisoquinolin-2-yl}pyrimidine NMR(CDCl$_3$): 1.1(m, 6H), 1.5(m, 12H), 2.1(s, 3H), 2.3(s, 3H), 2.7(m, 1H), 3.1(m, 1H), 3.5(m, 1H), 3.9(m, 1H), 4.5(m, 1H), 5.1(q, 1H), 5.2(t, 1H), 6.9(m, 4H), 7.1(d, 1H), 7.5(m, 2H).

EXAMPLE 159

5,6dimethyl-2-(4-fluorophenylamino)-4-{1-methyl-7-(N-t-butoxycarbonyl-O-benzyl-seryloxy)-1,2,3,4-tetrahydroisoquinolin-2-yl}pyrimidine NMR(CDCl$_3$): 1.5(m, 12H), 2.1(s, 3H), 2.3(s, 3H), 2.7(m, 1H), 3.1(m, 1H), 3.5(m, 1H), 3.8(m, 2H), 4.1(m, 1H), 4.6(m, 2H), 4.7(m, 1H), 5.0(q, 1H), 5.5(d, 1H), 6.9(m, 5H), 7.3(m, 5H), 7.4(m, 2H).

EXAMPLE 160

5,6dimethyl-2-(4-fluorophenylarnino)-4-{1-methyl-7-(N-t-butoxycarbonyl-methionyloxy)-1,2,3,4-tetrahydroisoquinolin-2-yl}pyrimidine NMR(CDCl$_3$): 1.5 (m, 12H), 2.1(m, 6H), 2.3(s, 3H), 2.6 (m, 3H), 3.1(m, 1H), 3.5(m, 1H), 3.9(m, 1H), 4.6(m, 1H), 5.1(m, 2H), 6.9(m, 4H), 7.1(d, 1H), 7.4(m, 2H).

EXAMPLE 161

5,6-dimethyl-2-(4-fluorophenylamino)-4-{1-methyl-7-(N-t-butoxycarbonyl-O-benzyl-aspartyloxy)-1,2,3, 4-tetrahydroisoquinolin-2-yl}pyrimidine NMR(CDCl$_3$): 1.5(m, 12H), 2.1(s, 3H), 2.3(s, 3H), 2.7(m, 1H), 3.1(m, 3H), 3.5(m, 1H), 3.9(m, 1H), 4.8(m, 1H), 5.1(m, 3H), 5.6(d, 1H), 6.9(m, 5H), 7.3(m, 5H), 7.5(m, 2H).

EXAMPLE 162

5,6dimethyl-2-(4-fluorophenylamino)-4-{1-methyl-7-(N-t-butoxycarbonyl-asparaginyloxy)-1,2,3,4-tetrahydroisoquinolin-2-yl}pyrimidine NMR(CDCl$_3$): 1.5(m, 12H), 2.1(s, 3H), 2.3(s, 3H), 2.6(m, 1H), 3.0(m, 3H), 3.5(m, 1H), 4.1(m, 1H), 4.3(m, 1H), 5.1(q, 1H), 6.0(d, 1H), 6.6(s, 1H), 6.7(m 1H), 6.9(m, 3H), 7.4(m, 2H).

EXAMPLE 163

5,6dimethyl-2-(4-fluorophenylamino)-4-{1-methyl-7-(N-t-butoxycarbonyl-glutamninyloxy)-1,2,3,4-tetrahydroisoquinolin-2-yl}pyrimidine NMR(CDCl3): 1.5(m, 12H), 2.1(m, 5H), 2.3(s, 3H), 2.6(m, 3H), 3.0(m, 1H), 3.5(m, 1H), 4.1(m, 2H), 5.1(q, 1H), 6.6(s, 1H), 6.7(d, 1H), 6.9(m, 3H), 2H).

EXAMPLE 164

5,6dimethyl-2-(4-fluorophenylamino)-4-{1-methyl-7-(N-t-butoxycarbonyl-Im-benzyl-histidyloxy)-1,2,3,4-tetrahydroisoquinolin-2-yl)pyrimidine NMR(CDCl$_3$): 1.5(m, 12H), 2.1(s, 3H), 2.3(s, 3H), 2.7(m, 1H), 3.1(m, 3H), 3.5(m, 1H), 3.9(m, 1H), 4.8(m, 1H), 5.0(m, 3H), 6.9(m, 8H), 7.3(m, 3H), 7.4(m, 3H).

EXAMPLE 165

5,6dimethyl-2-(4-fluorophenylamino)-4-{1-methyl-7-(N-t-butoxycarbonyl-phenylalanyloxy)-1,2,3,4-tetrahydroisoquinolin-2-yl}pyrimidine NMR(CDCl$_3$): 1.4(s, 9H), 1.5(m, 3H), 2.1(s, 3H), 2.3(s, 3H), 2.7(m, 1H), 3.1(m, 1H), 3.2(m, 2H), 3.5(m, 1H), 3.9(m, 1H), 4.8(m, 1H), 5.1(m, 2H), 6.6(m, 2H), 6.9(m, 2H), 7.2(m, 6H), 7.5(m, 2H).

EXAMPLE 166

5,6dimethyl-2-(4-fluorophenylamino)-4-{1-methyl-7-(N-t-butoxycarbonyl-prolyloxy)-1,2,3,4-tetrahydroisoquinolin-2-yl}pyrimidine NMR(CDCl$_3$): 1.5(m, 12H), 2.0(m, 4H), 2.1(s, 3H), 2.3(s, 3H), 2.7(m, 1H), 3.1(m, 1H), 3.5(m, 3H), 3.9(m, 1H), 4.5(m, 1H), 5.1(q, 1H), 6.6(m, 1H), 6.9(m, 4H), 7.4(m, 2H).

EXAMPLE 167

5,6dimethyl-2-(4-fluoropheniylamino)-4-(1-methyl-6-valyloxy-1,2,3,4-tetrahydroisoquinolin-2-yl)pyrimidine dihydrochloride 1-hydroxybenzotriazole(26.8 mg, 0.198 mmol), 1-ethyl-3-(3-dimethylarnino-propyl) carbodiimide (32.9 mg, 0.171 mmol), N-t-butyloxycarbonyl-valine (34.4 mg, 0.158 mmol), and triethylamine (23.9 µl, 0.171 mmol) were added to a suspension of 5,6-dimethyl-2-(4-fluorophenylamino)-4-(1-methyl-6-hydroxy-1,2,3,4-tetrahydroisoquinolin-2-yl}pyrimidine(50 mg, 0.132 mmol) in anhydrous methylene chloride (1 ml). The reaction mixture was stirred for 1 day at room temperature and washed with water. The separated organic layer was concentrated and the residual oil was purified by a silica gel column chromatography (dichloromethane/methanol 20/1). After evaporating of the solvent, the residual oil was dissolved in 3M hydrochloride-ethylacetate solution, stirred for 2 hours at room temperature and concentrated. The resulting white solid was suspended in ethyl ether and filtered to give the titled compound.

NMR(DMSO-d6): 1.0(m, 6H), 1.6(d, 3H), 2.2(s, 3H), 2.4(m, 4H), 2.9(m, 1H), 3.1(m, 1H), 3.6(m, 1H), 4.2(m, 2H), 5.4(m, 1H), 7.0(m, 2H), 7.3(m, 3H), 7.6(m, 2H), 8.8(m, 2H), 10.2(s, 1H).

EXAMPLE 168

5,6dimethyl-2-(4-fluorophenylamino)-4-(1-methyl-6-phenylalanyloxy-1,2,3,4-tetrahydroisoquinolin-2-yl)pyrimidine dihydrochloride The same procedures as in Example 167 were repeated using 5,6-dimethyl-2-(4-fluorophenylamino)-4-(1-methyl-6-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl) carbodiimide (32.9 mg, 0.171 mmol), N-t-butyloxycarbonyl-phenylalanine(42.0 mg, 0.158 mmol), and triethylamine(23.9 µl, 0.171 mmol) to afford the titled compound.

NMR(DMSO-d6): 1.6(d, 3H), 2.2(s, 3H), 2.4(s, 3H), 2.8(m, 1H), 3.1(m, 1H), 3.2(d, 2H), 3.6(m, 1H), 4.2(m, 1H), 4.5(m, 1H), 5.4(m, 1H), 6.8(m, 2H), 7.3(m, 8H), 7.6(m, 2H), 9.0(m, 2H), 10.2(s, 1H).

EXAMPLE. 169

5,6dimethyl-2-(4-fluorophenylamino)-4-(1-methyl-7-valyloxy-1,2,3,4-tetrahydroisoquinolin-2-yl)pyrimidine dihydrochloride The same procedures as in Example 167 were repeated using 5,6-dimethyl-2-(4-fluorophenylamino)-4-(1-methyl-7-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl) carbodiimide(32.9 mg, 0.171 mmol), N-t-butyloxycarbonyl-valine (34.4 mg, 0.158 mmol), and triethylamine (23.9 µl, 0.171 mmol) to afford the titled compound.

NMR(DMSO-d6): 1.0(m, 6H), 1.6(d, 3H), 2.2(s, 3H), 2.4(m, 4H), 2.9(m, 1H), 3.1(m, 1H), 3.6(m, 1H), 4.2(m, 2H), 5.4(m, 1H), 7.0(m, 2H), 7.3(m, 3H), 7.6(m, 2H), 8.9(m, 2H), 10.3(s, 1H).

EXAMPLE 170

5,6dimethyl-2-(4-fluorophenylamino)-4-(1-methyl-7-phenylalanyloxy-1,2,3,4-tetrahydroisoquinolin-2-yl)pyrimidine dihydrochloride The same procedures as in Example 167 were repeated using 5,6-dimethyl-2-(4-fluorophenylamino)-4-(1-methyl-7-hydroxy-1,2,3,4-tetrahydroisoquinolin-2-yl pyrimidine (SOmg, 0.132mmol), 1-hydroxybenzotriazole(26.8 mg, 0.198 mmol), 1-ethyl-3-(3-dimethylaminopropyl) carbodiimide (32.9 mg, 0.171 mmol), N-t-butyloxycarbonyl-phenylalanine (42.0 mg, 0.158 mmol), and triethylamine(23.9 µl, 0.171 mmol) to afford the titled compound.

NMR(DMSO-d6): 1.5(d, 3H), 2.2(s, 3H), 2.4(s, 3H), 2.8(m, 1H), 3.1(m, 1H), 3.2(d, 2H), 3.6(m, 1H), 4.2(m, 1H), 4.5(m, 1H), 5.3(m, 1H), 6.8(m, 2H), 7.3(m, 8H), 7.6(m, 2H), 9.0(m, 2H), 10.2(s, 1H).

EXAMPLE 171

5-methyl-6-valyloxymethyl-2-(4-fluorophenylamino)-4-(1-methyl-1,2,3,4-tetrahydroisoquinolin-2-yl)pyrimidine dibydrochloride The same procedures as in Example 167 were repeated using 5-methyl-6-hydroxymethyl-2-(4-fluorophenylamino)-4-(1-methyl-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl) carbodiimide (32.9 mg, 0.171 mmol), N-t-butyloxycarbonyl-valine (34.4 mg, 0.158 mmol), and triethylamine(23.9 µl, 0.171 mmol) to afford the titled compound.

NMR(DMSO-d6): 1.0(d, 6H), 1.6(d, 3H), 2.2(s, 3H), 2.3(m, 1H), 2.8(m, 1H), 3.2(m, 1H), 3.6(m, 1H), 4.2(m, 2H), 5.4(m, 3H), 7.2(m, 6H), 7.6(m, 2H), 8.8(m, 2H), 10.8(bs, 1H).

EXAMPLE 172

5-methyl-6-(phenylalanyloxymethyl)-2-(4-fluorophenylamino)-4-(1-methyl-1,2,3,4-tetrahydroisoquinolin-2-yl)pyrimidine dihydrochloride The same procedures as in Example 167 were repeated using 5-methyl-6-hydroxymethyl-2-(4-fluorophenylamino)-4-(1-methyl-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl)carbodiimide (32.9 mg, 0.171 mmol), N-t-butyloxycarbonyl-phenylalanine (42.0 mg, 0.158 mmol), and triethyl-amine (23.9 μl, 0.171 mmol) to afford the titled compound.

NMR(DMSO-d6): 1.6(d, 3H), 2.2(s, 3H), 2.8(m, 1H), 3.2(m, 1H), 3.3(d, 2H) 3.6(m, 1H), 4.2(m, 1H), 4.6(m, 1H), 5.4(m, 3H), 7.2(m, 1H), 7.6(m, 2H), 8.8(m, 211), 10.8(bs, 1H).

EXAMPLE 173

5-acetoxymethyl-6-methyl-2-(4-fluorophenylamino)-4-(1-methyl-1,2,3,4-tetrahydroisoquinolin-2-yl)pyrimidine dihydrochloride Acetylchloride (2.71 μl, 39.6 μmol) and triethylamine (20 μl, 142.6 μmol) were added to a suspension of 5-hydroxymethyl-6-methyl-4-(1-methyl-1,2,3,4-tetrahydroisoquinolin-2-yl)-2-(4-fluorophenylamino)pyrimidine (10 mg, 26.4 μmol) in dichloromethane(1 ml) and stirred for 1 day at a room temperature. The reaction mixture was purified by a silica gel column chromatography (ethylacetate/n-hexane=1/1) to give the titled compound.

NMR (CDCl$_3$): 1.6(d, 3H), 2.2 (s, 3H), 2.4(s, 3H), 2.8(m, 1H), 3.2(m, 1H), 3.6(m, 1H), 4.2(m, 1H), 4.6 (q, 2H), 5.4(q, 1H), 6.9(m, 3H), 7.2(m, 4H), 7.5(m, 2H).

EXAMPLE 174

5-valyloxymethyl-6-methyl-2-(4-fluorophenylamino)-4-(1-methyl-1,2,3,4-tetrahydroisoquinolin-2-yl)pyrimidine dihydrochloride The same procudures as in Example 167 were repeated using 5-hydroxymethyl-6-methyl-4-(1-methyl-1,2,3,4-tetrahydroisoquinolin-2-yl)-2-(4-fluorophenylamino)pyrimidine (50 mg, 0.1 32 mmol), 1-hydroxybenzotriazole (26.8 mg, 0.1 98 mmol), 1-ethyl-3-(3-dimethylaminopropyl)carbodiimide (32.9 mg, 0.171 mmol), N-t-butyloxycarbonyl-valine (34.4 mg, 0.158 mmol), and triethylamine(23.9 μl, 0.171 mmol) to afford the titled compound.

NMR (DMSO-d$_6$): 1.0 (d, 6H), 1.6 (d, 3H), 2.4 (s, 3H), 2.3 (m, 1H), 2.8 (m, 1H), 3.2 (m, 1H), 3.6 (m, 1H), 4.2 (m, 2H), 5.4 (m, 3H), 7.2 (m, 6H), 7.6 (m, 2H), 8.8 (m, 2H), 10.8(br, 1H).

EXAMPLE 175

5-methyl-6-(4-morpholineacetoxymethyl)-2-(4-fluorophenylamino)-4-(t1-methyl-1,2,3,4tetrahydroisoquinolin-2-yl)pyrimidine dihydrochloride The same procudures as in Example 167 were repeated using 5-methyl-6-hydroxymethyl-2-(4-fluorophenylamino)-4-(1-methyl-1,2,3,4-tetrahydroisoquinolin-2-yl)pyrinidine (50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), 4-morpholineacetic acid hydrochloride(28.8 mg, 0.158 mmol), and triethylamine(46 μl, 0.330 mmol) to afford the titled compound.

NMR(CDCl$_3$): 1.6(d, 3H), 2.2(s, 3H), 2.8(m, 1H), 3.2(m, 5H), 3.5(m, 1H), 3.8(s, 4H), 4.1(s, 2H), 4.2(m, 1H), 5.2(m, 3H), 7.0(m, 6H), 7.5(m, 2H), 11.0(s, 31H).

EXAMPLE 176

5,6dimethyl-2-(4-fluorophenylamino)-4-{1-methyl-6-(4-morpholineacetoxy)-1,2,3,4-tetrahydroisoquinolin-2-yl}pyrimidine dihydrochloride The same procudures as in Example 167 were repeated using 5,6-dimethyl-2-(4-fluorophenylamino)-4-(1-methyl-6-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), 4-morpholineacetic acid hydrochloride (28.8 mg, 0.158 mmol), and triethylamine (46 μl, 0.330 mmol) to afford the titled compound.

NMR(CDCl$_3$): 1.6(d, 3H), 2.2(s, 3H), 2.4(s, 3H), 2.7(m, 4H), 2.8(m, 1H) 3.2(m, 1H), 3.5(m, 3H), 3.8(m, 4H), 4.2(m, 1H), 5.3(m, 1H), 7.0(m, 5H), 7.5(m, 2H), 10.6(s, 1H), 14(bs, 1H).

EXAMPLE 177

5,6dimethyl-2-(4-fluorophenylamino)-4-{1-methyl-7-(4-morpholineacetoxy)-1,2,3,4-tetrahydroisoquinolin-2-yl}pyrimidine dihydrochloride The same procudures as in Example 167 were repeated using 5,6-dimethyl-2-(4-fluorophenylamino)-4-(1-methyl-7-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), 4-morpholineacetic acid hydrochloride(28.8 mg, 0.158 mmol), and triethylamine(46 μl, 0.330 mmol) to afford the titled compound.

NMR(CDCl$_3$): 1.6(d, 3H), 2.2(s, 3H), 2.4(s, 3H), 2.8(m, 1H), 3.0(s, 4H), 3.2(m, 1H), 3.5(m, 1H), 3.7(m, 4H), 3.9(m, 4H), 4.2(m, 1H), 5.3(m, 1H), 7.0(m, 5H), 7.5(m, 2H), 10.2(s, 1H).

EXAMPLE 178

5-methyl-6-(4-benzylpiperazine)acetoxymethyl-2-(4-fluorophenylamino)-4-(1-methyl-1,2,3,4-tetrahydroisoquinolin-2-yl)pyrimidine trihydrochloride The same procudures as in Example 167 were repeated using 5-methyl-6-hydroxymethyl-2-(4-fluorophenylamino)-4-(1-methyl-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), 4-benzylpiperazineacetic acid dihydrochloride (48.7 mg, 0.158 mmol), and triethylamine(64 μl, 0.462 mmol) to afford the titled compound.

NMR(CDCl$_3$): 1.6(d, 3H), 2.2(s, 3H), 2.8(m, 1H), 3.2(m, 1H), 3.3(m, 8H) 3.5(m, 1H), 4.0(s, 2H), 4.2(m, 3H), 5.2(m, 3H), 7.0(m, 7H), 7.5(m, 6H) 11.0(d, 1H).

EXAMPLE 179

5,6dimethyl-2-(4-fluorophenylamino)-4-{1-methyl-6-(4-benzylpiperazine)acetoxy- 1,2,3,4tetrahydroisoquinolin-2-yl}pyrimnidine trihydrochioride The same procudures as in Example 167 were repeated using 5,6-dimethyl-2-(4-fluorophenylamino)-4-(1-methyl-6-hydroxy 1,2,3,4-tetrahydroisoquinolin-2-ylppyrimidine (50 mg, 0.132 mmol ), 1-hydroxybenzotriazole(26.8 mg, 0.1 98 mmol), -ethyl-3-(3-dimethylaminopropyl)carbodiimide (32.9 mg, 0.171 mol), 4-benzylpiperazinoacetic acid dihydrochyoride (48.7 mg, 0.158mmol), and triethylamine(64 µl, 0.462mmol) to afford the titled compound.

NMR(CDCl $_3$): 1.6(d, 3H), 2.2(s, 3H), 2.4(s, 3H), 2.7(m, 9H), 3.1(m, 1H), 3.5(m, 3H), 3.6(s, 2H), 4.0(m, 1H), 5.2(m, 1H), 6.9(m, 5H), 7.3(m, 5H) 7.5(m, 2H), 8.9(bs, 1H).

EXAMPLE 180

5,6dimethyl-2-(4-fluorophenylamino)-4-{(1-methyl-7-(4-benzylpiperazine)acetoxy 1,2,3,4-tetrahydroisoquinolin-2-yl}pyrimidine trihydrochioride The same procudures as in Example 167 were repeated using 5,6-dimethyl-2-(4-fluorophenylamino)-4{(1-methyl-7-hydroxy-1,2,3,4-tetrahydroisoquinolin-2-yl}pyrimidine (50 mg, 0.132 mmol), 1-hydroxybenzotriazole(26.8 mg, 0.198 mmol), 1-ethyl-3-(3-dimethylaminopropyl) carbodiimide(32.9 mg, 0.171 mmol), 4-benzyd piperazinoacetic acid dihydrochtoride (48.7 mg, 0.158 mmol), and triethylamine(64 µl, 0.462 mmol) to afford the titled compound.

NMR(CDCl$_3$): 1.6(d, 3H), 2.2(s, 3H), 2.4(s, 3H), 2.8(m, 9H), 3.1(m, 1H) 3.5(m, 3H), 3.8(s, 2H), 4.2(m, 1H), 5.2(m, 1H), 6.9(m, 5H), 7.4(m, 7H), 10.1(bs, 1H).

EXAMPLE 181

5-rethyl-6-(1-piperidineacetoxymethyl)-2-(4-fluorophenylamino)-4-(1-methyl-1,2,3,4-tetrahydroisoquinolin-2-yl)pyrimidine dihydrochloride The same procudures as in Example 167 were repeated using 5-methyl-6-hydroxymethyl-2-(4-fluorophenylamino)-4-(1-methyl-1,2,3,4-tetrahydroisoquinoli-2-yl)pyrimiidine (50 mg, 0.132 mmol), 1-hydroxybenzotriazole(26.8 mg, 0.198 mmol), 1-ethyl-3-(3-dimethylaminopropyl) carbodiimnide(32.9 mg, 0.171 mmol), piperidineacetic acid hydrochloride (28.5 mg, 0.158 mmol), and triethylamne(46 µl, 0.330 mmol) to afford the titled compound.

NMR(CDCl$_3$): 1.6(d, 3H), 1.9(m, 6H), 2.2(s, 3H), 2.8(m, 1H), 3.1(m, 1H), 3.2(m, 4H), 3.5(m, 1H), 4.2(m, 3H), 5.2(m, 3H), 6.9(m, 2H), 7.2(m, 4H), 7.5(m, 2H), 10.2(bs, 1H).

EXAMPLE 182

5,6dimethyl-2-(4-fluorophenylamino)-4-{1-methyl-6-(1-piperidineacetoxy)-1,2,3,4-tetrahydroisoquinolin-2-yl}pyrimidine dihydrochloride The same procudures as in Example 167 were repeated using 5,6-dimethyl-2-(4-fluorophenylamino)-4-(1-methyl-6-hydroxy-1,2,3,4-tetrahydroisoquinolin-2-yl)pyrimidine (50 mg, 0.132 mmol), 1-hydroxybenzotriazole(26.8 mg, 0.198 mmol), 1-ethyl-3-(3-dimethylaminopropyl) carbodiimide(32.9 mg, 0.171 mmol), 1-piperidineacetic acid hydrochloride (28.5 mg, 0.158 mmol), and triethylamine(46 µl, 0.330 mmol) to afford the titled compound.

NMR(CDCl$_3$): 1.5(m, 9H), 2.2(s, 3H), 2.4(s, 3H), 2.6(m, 4H), 2.8(m, 1H) 3.1(m, 1H), 3.5(m, 3H), 4.0(m, 1H), 5.2(m, 1H), 7.0(m, 5H), 7.5(m, 2H), 8.5(bs, 1H).

EXAMPLE 183

5,6dimethyl-2-(4-fluorophenylamino)-4-{1-methyl-7-(1-piperidinoacetoxy)-1,2,3,4-tetrahydroisoquinolin-2-yl}pyrimidine dihydrochloride The same procudures as in Example 167 were repeated using 5,6-dimethyl-2-(4-fluorophenylamino)-4(1-methyl-7-hydroxy-1,2,3,4-tetrahydroisoquinolin- 2-yl)pyrimidine(50 mg, 0.1 32 mmol), 1-hydroxybenzotriazole(26.8 mg, 0.198 mmol) 1-ethyl-3-(3-dimethylaminopropyl)carbodiimide (32.9 mg, 0.17 mmol), 1-piperidineacetic acid hydrochloride (28.5 mg, 0.15 8 mmol), and triethylamine(46 µl, 0.330 mmol) to afford the titled compound.

NMR(CDCl$_3$): 1.5(m, 9H), 2.2(s, 3H), 2.4(s, 3H), 2.6(m, 4H), 2.8(m, 1H), 3.1(m, 1H), 3.5(m, 3H), 4.1(m, 1H), 5.2(m, 1H), 7.0(m, 5H), 7.5(m, 2H), 9.9(bs, 1H).

EXAMPLE 184

5,6dimethyl-2-(4-fluoro-2-valyfoxyphenylamino)-4-1-methyl-1,2,3,4-tetrahydroisoquinolin-2-yl) pyrimidine dihydrochloride The same procudures as in Example 167 were repeated using 5,6-dimethyl-4-(1-methyl-1,2,3,4-tetrahydroisoquinolin-2-yl)-2-(4-fluoro-2-hydroxyphenylamino)pyrimidine (50 mg, 0.132 mmol), 1-hydroxybenzotriazole(26.8 mg, 0.198 mmol), 1-ethyl-3-(3-dimethylaminopropyl)carbodiimide(32.9 mg, 0.171 mmol), N-t-butyloxycarbonyl-valine(34.4 mg, 0.158mmol), and triethylamine(23.9 µl, 0.171 mmol) to afford the titled compound.

NMR (DMSO-d$_6$): 1.0 (m, 6H), 1.6 (d, 3H), 2.2 (s, 3H), 2.4 (m, 4H), 2.9 (m, 1H), 3.1 (m, 1H), 3.6 (m, 1H), 4.2 (m, 1H), 4.6 (m, 1H), 5.4 (m, 1H), 7.2 (m, 5H), 7.6 (m, 2H), 8.9 (m, 2H).

EXAMPLE 185

5,6dimethyl-2-(4-fluoro-2-phenylalanyloxyphenylamino)-4-(1-methyl-1,2,3,4-tetrahydroisoquinolin-2-yl)pyrimidine dihydrochloride The same procedures as in Example 167 were repeated using 5,6-dimethyl-4-(1-methyl-1,2,3,4-tetrahydroisoquinolin-2-yl)-2-(4-fluoro-2-hydroxyphenylamino)pyrimidine (50 mg, 0.132 mmol), 1-hydroxybenzotriazole(26.8 mg, 0.198 mmol), 1-ethyl-3-(3-dimethylamninopropyl)carbodiimide(32.9 mg, 0.171 mmol), N-t-butyloxycarbonyl-phenylalanine(42.0 mg, 0.158 mmol), and triethylamine(23.9 µl, 0.171 mmol) to afford the titled compound.

NMR (DMSO-d$_6$): 1.5 (d, 3H), 2.2 (s, 3H), 2.4 (s, 3H), 2.8 (m, 1H), 3.1 (m, 3H), 3.6 (m, 1H), 4.2 (m, 1H), 5.0 (m, 1H), 5.4 (m, 1H), 6.8 (m, 2H), 7.2 (m, 10H), 9.0 (m, 2H).

EXAMPLE 186

2-(4-Fluorophenylamino)-5-methoxymethyl-6-methyl-4-(1-methyl-1,2,3,4-tetrahydroisoquinoline-2-yl)pyrimidine hydrochloride 2-(4-Fluorophenylamino)-6-methyl-4-(1-methyl-1,2,3,4-tetrahydroisoquino-line-2-yl)pyrimidine (0.9 g, 2.58 mmol) was added to chloromethyl methyl ether (3 ml) in a sealed tube. The mixture was stirred at 80° C. for 1 day. After cooling to room temperature, ethyl ether was added to mixture. Resulting solid was removed by filtration. Filtrate was washed with aqueous 2N NaOH solution, dried over sodium sulfate, and concentrated under reduced pressure. Crude product was purified with a silica gel column chromatography (eluent: ethyl acttate:hexane=1:3). Purified compound was treated with HCl solution in ethyl ether. Precipitated solid was isolated by filtration, washed with ethyl ether, and dried in vacuum. It gave 0.6 mg of the titled compound.

Yield: 0.05%; NMR (CDCl3): δ 1.6(d, 3H), 2.4(s, 3H), 2.8(m, 1H), 3.2(m, 1H), 3.5(s, 3H), 3.6(m, 1H), 4.2(m, 3H), 5.4(q, 1H), 6.9(m, 2H), 7.1(m, 4H), 7.5(m, 2H).

Test 1: Inhibition of proton pump ($H^+/K^+$-ATPase activity)

A proton pump enzyme was prepared by the same method as in the Experiment 1-1 of WO 94/14795. Further, the inhibitory effect of proton pump activity was measured by the same method as in Experiment 1-2 of WO 94/14795.

Namely, the proton pump activity stimulated by $Mg^{++}$ was used as a negative comparative group, and the activity stimulated by $Mg^{++}$ and $K^+$ was used as a positive comparative group. The comparative compound was omeprazole.

Test tubes were divided into 4 groups: Group 1 as negative comparative group(n=3), Group 2 as positive comparative group(n=3), Group 3(n=5×2) to be administered with the compound of the present invention and Group 4(n=5×2) to be administered with the comparative compound.

The inhibitory effects of Groups 3 and 4 on proton pump activity were measured by employing the compound prepared in Examples and omeprazole, respectively, each of which was dissolved in dimethylsulfoxide at 5 different concentrations.

To each of Groups 1, 2, 3 and 4 were added 100 μl of magnesium chloride(40 mM) dissolved in 40 mM Tris-HCI buffer(ph 6.0) and 100 μg of the enzyme source. The 50 μl of potassium chloride(50 mM) and 50 μl of ammonium chloride(6 mM) dissolved in 40 mM Tris-HCl buffer(pH 6.0) were added to all groups except for group 1.

10 μl of dimethylsulfoxide was added to each of Groups 1 and 2; and to Group 3 was added 10 μl of dimethylsulfoxide solution prepared by dissolving compound of EXAMPLE at 5 different concentration(n=5×2). To Group 4, 10 μl of the solution prepared by dissolving omeprazole in dimethylsulfoxide at 5 different concentration(37.6, 21.4, 12.2, 7.0 and 4.0 μM) was added(n=5×2). 40 mM Tris-HCI buffer(pH=6.0) was added thereto so as to make the total volume 400 μl.

Thereafter, the test tube of each Group were placed at 37° C. for 30 minutes for the preincubation. 100 μl ATP solution (6.6 mM) was added until the reaction volume became 500 μl. After the reaction was carried out at 37° C. for 30 minutes, 25% cold trichloroacetic acid was added to terminate the enzyme reaction. The released inorganic phosphate was measured by an automatic analyzer(Express 550, coming).

The difference between Group 1 and Group 2 represents the proton pump activity activated by $K^+$ only. The $IC_{50}$s of Group 3 and 4 were calculated from Litchfield-wilcoxon equation[see, e.g., *J. Pharrnacol. Exp. Ther.*, 96, 99(1949)]. The concentrations of the test compounds inhibiting 50% of the proton pump activity are represented as $IC_{50}$ in Table 1.

TABLE 1

| Test compound | IC50 (μM) | Effect ratio |
|---|---|---|
| Example 2 | 7.85 | 1.4 |
| Example 5 | 6.91 | 1.6 |
| Example 14 | 2.15 | 5.2 |
| Example 22 | 6.69 | 1.7 |
| Example 23 | 0.43 | 25.8 |
| Example 25 | 1.85 | 6.0 |
| Example 26 | 2.60 | 4.3 |
| Example 27 | 1.55 | 7.2 |
| Example 28 | 1.74 | 6.4 |
| Example 29 | 2.55 | 4.4 |
| Example 31 | 2.56 | 4.3 |
| Example 32 | 1.34 | 8.3 |
| Example 34 | 0.43 | 25.8 |
| Example 36 | 0.31 | 35.8 |
| Example 43 | 0.18 | 61.7 |
| Omeprazole | 11.10 | — |

As shown in Table 1, the compounds of the present invention have an excellent proton pump inhibitory activity over omeprazole.

Test 2: Inhibition of gastric secretion

In accordance with the method disclosed in Shay, H., et al., Gastroenterology 5 43–61(1945), Test 2 was carried out.

Sprague-Dawly rats having a body weight of 170±10 g were divided into 3 groups(n=5) and deprived of food for 24 hours before the experiment with free access to water. Under ether anesthesia, the abdomen was incised, and the pylorus was ligated. As a comparative group, Group 1 was administered intraduodenally in a volume of 0.5 ml/200 g of 30% aqueous polyethylene glycol 400 solution. Groups 2 and 3 were administered intraduodenally with the compound of Example and omeprazole, respectively, each of which was suspended in 30% aqueous polyethylene glycol 400 solution at a concentration of 20 mg/kg. After closing the abdominal cavity, the rats were placed for 5 hours and then killed by cervical dislocation. The stomach was extracted to obtain gastric juice.

Tne gastric juice was centrifuged at 1,000 g to remove precipitates. The amount and acidity of the gastric juice were measured. Relative volumes, relative acid concentrations and relative acid outputs of the test compounds were calculated from equations(I), (II) and (III) and the results are shown in Table 2.

Relative volume=(the average amount of gastric juice of Group 1—the average amount of gastric juice of Group 2)/(the average amount of gastric juice of Group 1–the average amount of gastric juice of Group 3)—(I)

Relative acid concerntration=(the average acidity of Group 1—the average acidity of Group 2)/(the average acidity of Group 1—the average acidity of Group 3)—(II)

Relative acid output (the total amount of acid output of Group 1—the total amount of acid output of Group 2)/(the total amount of acid output of Group 1—the total amount of acid output of Group 3)—(m)

The results are shown in Table 2.

TABLE 2

| Test compound | Relative volume | Relative conc. | Relative Acid Output |
|---|---|---|---|
| Example 2 | 0.69 | 0.57 | 0.70 |
| Example 5 | 0.45 | 0.18 | 0.43 |
| Example 14 | 0.93 | 0.41 | 0.79 |
| Example 22 | 0.59 | 0.46 | 0.62 |
| Example 23 | 1.58 | 1.34 | 1.23 |
| Example 25 | 1.00 | 0.52 | 0.86 |
| Example 26 | 0.67 | 0.64 | 0.74 |
| Example 27 | 0.99 | 0.68 | 0.90 |
| Example 28 | 0.78 | 0.60 | 0.78 |
| Example 29 | 0.78 | 0.81 | 0.88 |
| Example 31 | 1.06 | 0.97 | 1.01 |
| Example 32 | 0.84 | 0.47 | 0.77 |
| Example 34 | 0.81 | 0.45 | 0.78 |
| Example 36 | 1.05 | 1.08 | 1.15 |
| Example 50 | 1.01 | 0.77 | 0.98 |
| Example 51 | 1.09 | 1.02 | 1.06 |
| Example 52 | 0.86 | 0.88 | 0.96 |
| Example 54 | 0.79 | 0.79 | 0.95 |
| Example 74 | 1.57 | 1.02 | 1.25 |
| Example 107 | 0.62 | 0.56 | 0.73 |
| Example 139 | 1.01 | 0.75 | 1.01 |
| Example 144 | 0.90 | 0.80 | 0.94 |
| Example 171 | 1.46 | 1.42 | 1.33 |
| Example 172 | 1.48 | 1.33 | 1.34 |
| Example 175 | 0.87 | 0.30 | 0.79 |
| Example 181 | 0.99 | 0.16 | 0.80 |

What is claimed is:

1. Pyrimidine derivative of the following formula (I):

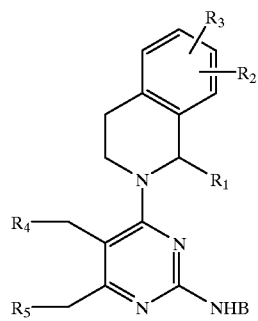

(I)

wherein

B is $C_3$–$C_7$ cycloalkyl; $C_1$–$C_3$ alkoxyethyl; 1-naphthylmethyl, 4-methylthiazol-2-yl or 4-phenylthiazol-2-yl or a group of formula (II):

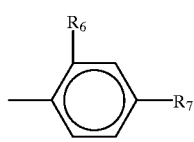

(II)

wherein $R_6$ is hydrogen, methyl, hydroxy, methoxy, or a group of formula (III):

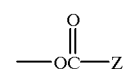

(III)

wherein Z is $C_1$–$C_4$ alkyl; $C_2$–$C_4$ alkenyl optionally substituted by phenyl; cycloalkyl; benzyloxyalkyl; alkoxycarbonylalkyl; morpholinomethyl; piperidinomethyl; 4-benzylpiperazinomethyl; phenyl optionally mono- or polysubstituted by nitro, halogen, $C_1$–$C_5$ alkyl, $C_1$–$C_4$ alkoxy, cyano or trifluoromethyl; naphthyl; benzyl optionally substituted by alkoxy; thiophen-2-yl-methyl; 1-alkoxycarbonyl-pyrrolidin-2-yl or —$CHR_8NHR9$, wherein $R_8$ is hydrogen, methyl, isopropyl, benzyl, benzyloxymethyl, methylthioethyl, benzyloxycarbonylmethyl, carbamoylmethyl, carbamoylethyl, or 1-benzylimidazol-4-ylmethyl and $R_9$ is hydrogen or t-butoxycarbonyl; and $R_7$ is hydrogen or halogen; $R_1$ is hydrogen, methyl, hydroxymethyl or $C_1$–$C_3$ alkoxymethyl, and $R_2$, $R_3$, $R_4$ and $R_5$ are respectively hydrogen, methyl, hydroxy, methoxy, or the group of formula (III) wherein Z is the same as defined above;

provided that when B is $C_3$–$C_7$ cycloalkyl, $C_1$–$C_3$ alkoxyethyl, 1-naphthylmethyl, 4-methylthiazol-2-yl or 4-phenylthiazol-2-yl, then $R_1$ is hydrogen or methyl, and $R_2$, $R_3$, $R_4$, and $R_5$ are hydrogen;

when B is a group of formula (II) and $R_1$ is hydroxymethyl or $C_1$–$C_3$ alkoxymethyl, then $R_2$, $R_3$, $R_4$, $R_5$ and $R_6$ are hydrogen; and when B is a group of formula (II) and $R_1$ is hydrogen or methyl, then one or two of $R_2$, $R_3$, $R_4$, $R_5$ and $R_6$ are hydroxy, methoxy, or a group of formula (III) and the others are hydrogen or methyl, or pharmaceutically acceptable salts thereof.

2. The compound of claim 1, wherein B is $C_3$–$C_7$ cycloalkyl, $C_1$–$C_3$ alkoxyethyl, 1-naphthylmethyl, 4-methylthiazol-2-yl or 4-phenylthiazol-2-yl.

3. The compound of claim 1, wherein B is a group of formula (II); $R_1$ is hydrogen or methyl; and one or two of $R_2$, $R_3$, $R_4$, $R_5$ and $R_6$ are hydroxy or methoxy.

4. The compound of claim 1, wherein B is a group of formula (II); $R_1$ is hydrogen or methyl; and one or two of $R_2$, $R_3$, $R_4$, $R_5$ and $R_6$ are a group of formula (III).

5. The compound of claim 1, wherein B is a group of formula (II) and $R_1$ is hydroxymethyl or $C_1$–$C_3$ alkoxymethyl.

6. A pharmaceutical composition for treating peptic ulcer which comprises a therapeutically effective amount of the pyrimidine derivative or pharmaceutically acceptable salt thereof defined in claim 1 together with a conventionally pharmaceutically acceptable carrier.

7. A method for treating peptic ulcer comprising administering to a subject in need of such treatment a pyrimidine derivative or pharmaceutically acceptable salt thereof as defined in claim 1 in an amount effective for treating peptic ulcer.

8. A method for treating peptic ulcer comprising administering to a subject in need of such treatment a pyrimidine derivative or pharmaceutically acceptable salt thereof as defined in claim 2 in an amount effective for treating peptic ulcer.

9. A method for treating peptic ulcer comprising administering to a subject in need of such treatment a pyrimidine derivative or pharmaceutically acceptable salt thereof as defined in claim 3 in an amount effective for treating peptic ulcer.

10. A method for treating peptic ulcer comprising administering to a subject in need of such treatment a pyrimidine derivative or pharmaceutically acceptable salt thereof as defined in claim 4 in an amount effective for treating peptic ulcer.

11. A method for treating peptic ulcer comprising administering to a subject in need of such treatment a pyrimidine derivative or pharmaceutically acceptable salt thereof as defined in claim 5 in an amount effective for treating peptic ulcer.

12. The compound of claim 1, wherein the pharmaceutically acceptable salt is an inorganic acid salt.

13. The compound of claim 12, wherein the inorganic acid salt is selected from the group consisting of hydrochloride, sulfate, phosphate and nitrate salts.

14. The compound of claim 1, wherein the pharmaceutically acceptable salt is an organic acid salt.

15. The compound of claim 14, wherein the organic acid salt is selected from the group consisting of tartrate, fumarate, citrate, mesylate and acetate salts.

16. 5,6-dimethyl-2-(2-methoxyethylamino)-4-(1-methyl-1,2,3,4-tetrahydroisoquinolin-2-yl)pyrimidine or a pharmaceutically acceptable salt thereof.

17. 6-hydroxymethyl- 5-methyl-2-(4-fluorophenylamino)-4-(1-methyl-1,2, 3,4-tetrahydroisoquinolin-2-yl)pyrimidine or a pharmaceutically acceptable salt thereof.

18. 5,6-dimethyl-2-(4-fluorophenylamino)-4-(1-methyl-6-hydroxy-1,2,3,4-tetrahydroisoquinolin-2-yl)pyrimidine or a pharmaceutically acceptable salt thereof.

19. 5-hydroxymethyl-6-methyl-4-(1-methyl-1,2,3,4-tetrahydroisoquinolin-2-yl)-2-(4-fluorophenylamino) pyrimidine or a pharmaceutically acceptable salt thereof.

20. 5-hydroxymethyl-6-methyl-2-(4-fluorophenylamino)-4-(1-methyl-6-hydroxy-1,2,3,4-tetrahydroisoquinolin-2-yl) pyrimidine or a pharmaceutically acceptable salt thereof.

21. 5-methyl-6-(thiophen-2-yl-acetoxymethyl)-2-(4-fluorophenylamino)-4-(1-methyl-1,2,3,4-tetrahydroisoquinolin-2-yl)pyrimidine or a pharmaceutically acceptable salt thereof.

22. 5-methyl-6-valyloxymethyl-2-(4-fluorophenylamino)-4-(1-methyl-1,2,3,4-tetrahydroisoquinolin-2-yl)pyrimidine or a pharmaceutically acceptable salt thereof.

23. 5-methyl-6-(phenylalanyloxymethyl)-2-(4-fluorophenylamino)-4-(1-methyl-1,2,3,4-tetrahydroisoquinolin-2-yl)pyrimidine or a pharmaceutically acceptable salt thereof.

24. 5,6-dimethyl-2-(4-methylthiazol-2-yl)amino-4-(1,2,3,4-tetrahydroisoquinolin-2-yl)pyrimidine or a pharmaceutically acceptable salt thereof.

* * * * *